United States Patent
Kang

(10) Patent No.: US 11,439,640 B2
(45) Date of Patent: Sep. 13, 2022

(54) PHARMACEUTICAL COMPOSITION COMPRISING SUBSTANCE INHIBITING ENZYMATIC ACTIVITY OF PEROXIREDOXIN 2 AS EFFECTIVE INGREDIENT FOR TREATMENT OF COLORECTAL CANCER

(71) Applicant: EWHA UNIVERSITY-INDUSTRY COLLABORATION FOUNDATION, Seoul (KR)

(72) Inventor: Sang Won Kang, Seoul (KR)

(73) Assignee: EWHA UNIVERSITY—INDUSTRY COLLABORATION FOUNDATION, Seoul (KR)

(*) Notice: Subject to any disclaimer, the term of this patent is extended or adjusted under 35 U.S.C. 154(b) by 160 days.

(21) Appl. No.: 16/728,100

(22) Filed: Dec. 27, 2019

(65) Prior Publication Data

US 2020/0129508 A1    Apr. 30, 2020

Related U.S. Application Data

(63) Continuation-in-part of application No. PCT/KR2018/007316, filed on Jun. 27, 2018.

(30) Foreign Application Priority Data

Jun. 27, 2017  (KR) ......................... 10-2017-0081491
Jun. 27, 2018  (KR) ......................... 10-2018-0074375

(51) Int. Cl.
*A61K 31/502* (2006.01)
*A61P 35/00* (2006.01)

(52) U.S. Cl.
CPC ............ *A61K 31/502* (2013.01); *A61P 35/00* (2018.01)

(58) Field of Classification Search
CPC ................................ A61K 31/502; A61P 35/00
See application file for complete search history.

(56) References Cited

PUBLICATIONS

ColorectalCancerPrevention, 2021, https://www.cancer.org/cancer/colon-rectal-cancer/causes-risks-prevention/prevention.html.*
Xu et al., Bioscience Reports, 2017, 37, 1-9.*
Hurst et al., 1954, caplus an 1954:4690.*
Jeralyn D.Haraldsen et al., "Identification of Conoidin A as a Covalent Inhibitor of Petoxiredoxin II", Organic & Biomolecular Chemistry, Aug. 7, 2009, pp. 3040-3048, vol. 7, No. 15.
Gu Liu et al., "Optimisation of Conoidin A, a Peroxiredoxin Inhibitor", ChemMedChem, 2010, pp. 41-45, vol. 5.
Jennifer B.Nguyen et al., "Peroxiredoxin-1 from the Human Hookworm Ancylostoma Ceylanicum Forms a Stable Oxidized Decamer and Is Covalently Inhibited by Conoidin A", Chemistry & Biology, Aug. 22, 2013, pp. 991-1001, vol. 20, No. 8.
Linglong Peng et al., "Peroxiredoxin 2 is associated with colorectal cancer progression and poor survival of patients", Oncotarget, Jan. 24, 2017, pp. 15057-15070, vol. 8, No. 9.
Weidong Lu et al., "Peroxiredoxin 2 is upregulated in colorectal cancer and contributes to colorectal cancer cells' survival by protecting ceils from oxidative stress", Molecular and Cellular Biochemistry, 2014, pp. 261-270, vol. 387.
International Search Report for PCT/KR2018/007316, dated Oct. 29, 2018.

* cited by examiner

*Primary Examiner* — Sun Jae Yoo
(74) *Attorney, Agent, or Firm* — Sughrue Mion, PLLC

(57) ABSTRACT

The present invention relates to a pharmaceutical composition for treating colorectal cancer including a material inhibiting the enzyme activity of peroxiredoxin 2 as an active ingredient, and more specifically, to a pharmaceutical composition for treating colorectal cancer, which exhibits the effect of reducing colon polyps via increase of active β-catenin degradation by inhibiting the activity of peroxiredoxin 2, based on the mechanism that promotes colorectal tumor by the interaction between peroxiredoxin 2 (PrxII) and tankyrase (TNKS) in an APC-mutant cell.

7 Claims, 63 Drawing Sheets
(37 of 63 Drawing Sheet(s) Filed in Color)

Specification includes a Sequence Listing.

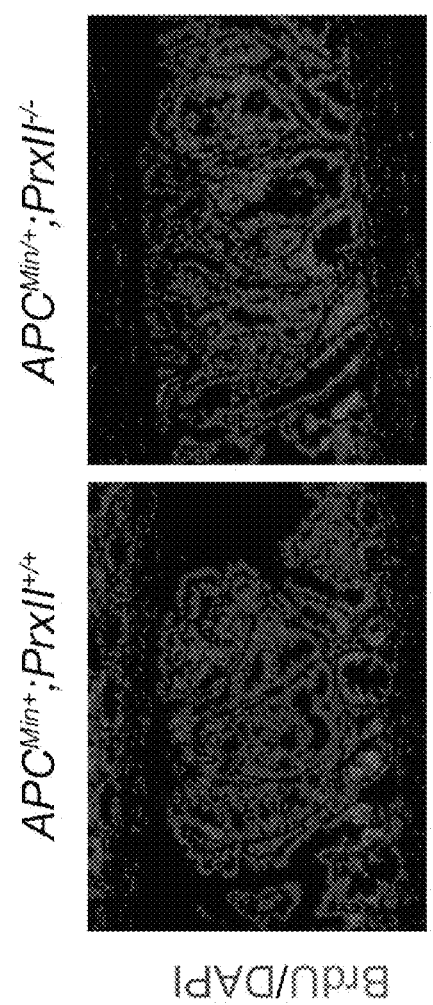
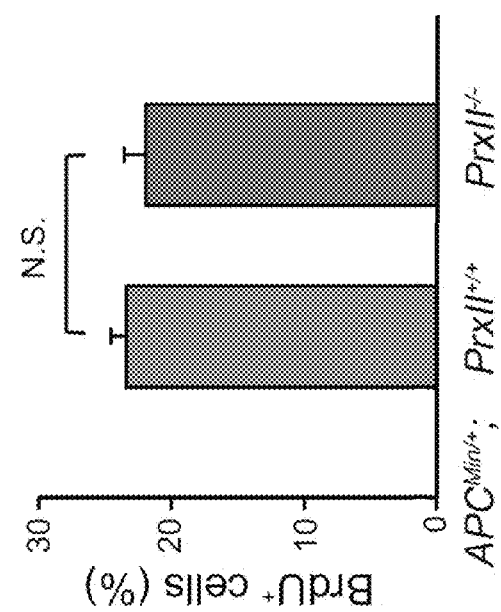
[Fig. 12]

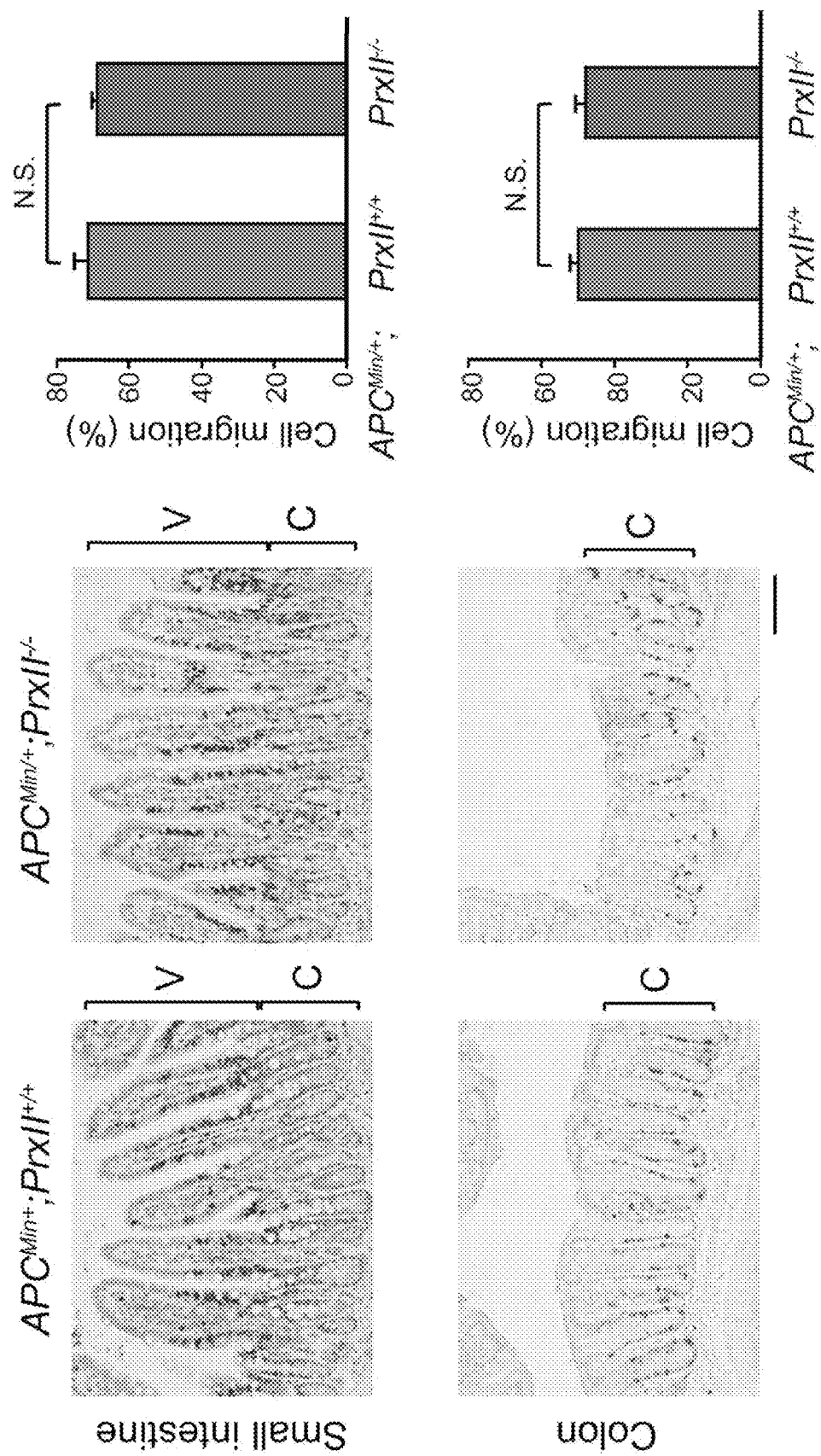

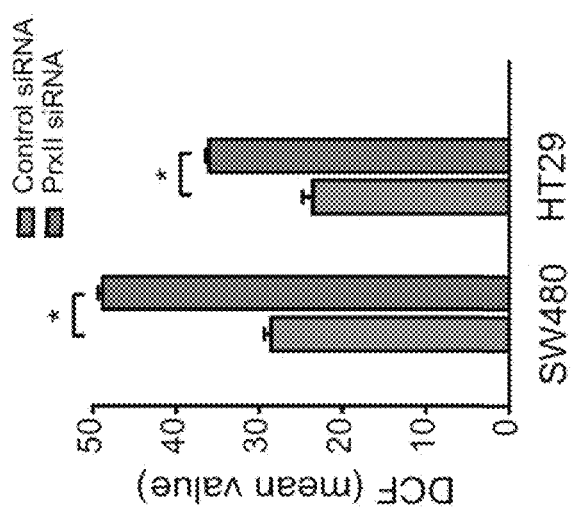
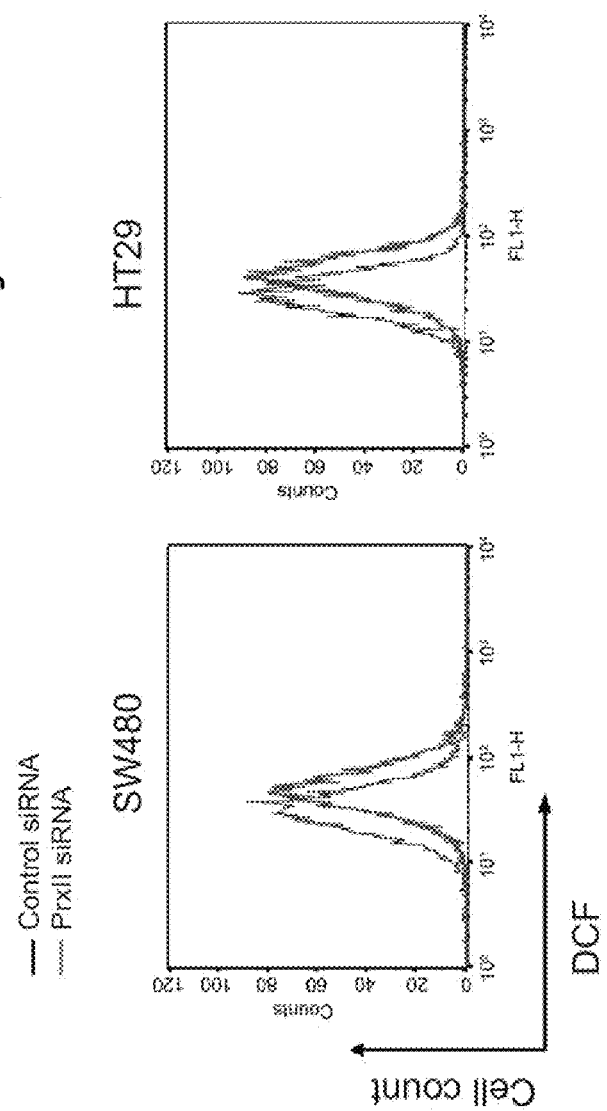
Fig. 20

[Fig. 74B]
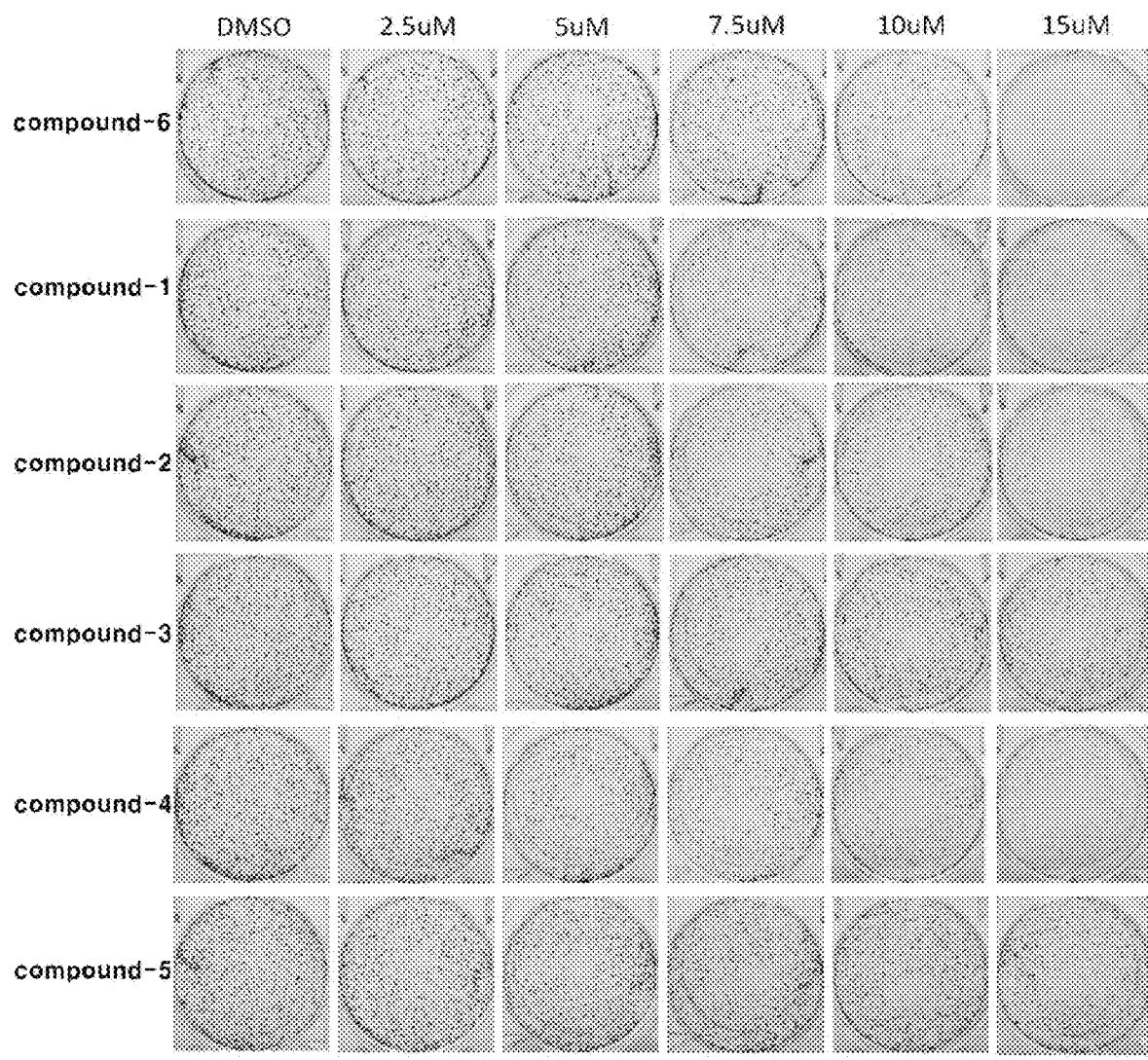

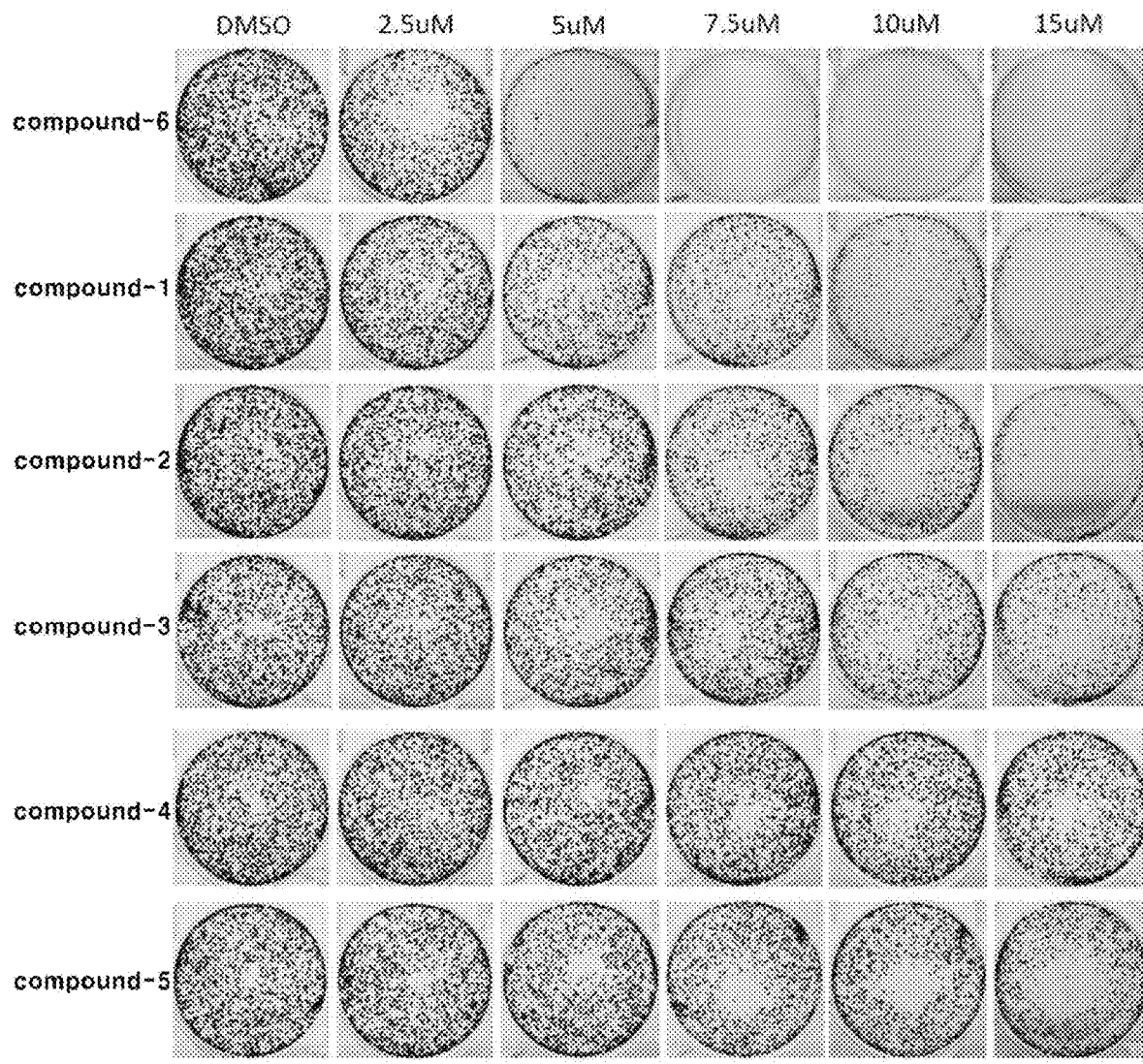
[Fig. 75B]

PHARMACEUTICAL COMPOSITION COMPRISING SUBSTANCE INHIBITING ENZYMATIC ACTIVITY OF PEROXIREDOXIN 2 AS EFFECTIVE INGREDIENT FOR TREATMENT OF COLORECTAL CANCER

CROSS REFERENCE TO RELATED APPLICATIONS

This application is a Continuation in Part of International Application No. PCT/KR2018/007316 filed Jun. 27, 2018, claiming priority based on Korean Patent Application No. 10-2017-0081491 filed Jun. 27, 2017 and Korean Patent Application No. 10-2018-0074375 filed Jun. 27, 2018, the contents of all of which are incorporated herein by reference in their entirety.

TECHNICAL FIELD

The present invention relates to a pharmaceutical composition for treating colorectal cancer comprising a material inhibiting the enzyme activity of peroxiredoxin 2 as an active ingredient.

BACKGROUND ART

Cancer is one of the most intractable diseases and is constantly being studied for the cure of cancer patients. In addition, in hospitals, techniques such as drug treatment, radiation therapy, gene therapy, etc. are being used to treat cancer.

Colorectal cancer (CRC) is a common cancer worldwide. In Korea, colorectal cancer is the most frequently occurring cancer in men following gastric cancer, lung cancer, and liver cancer, and is the most frequently occurring cancer in women following breast cancer and gastric cancer. In recent years, as the diet of Koreans becomes westernized, the incidence has increased more rapidly. The mortality rate from colorectal cancer has increased by about 80% over the last 10 years and it continues to increase.

About 40-50% of CRC patients develop relapses and metastasis. The main cause of death in patients with malignant tumors, including CRC, is due to the metastasis of a malignant tumor rather than the malignant tumor itself. Most cancer metastasis are multiple and systemic.

According to mass sequencing analysis data, more than 80% of CRC patients have a mutation in the adenomatous polyposis coli (APC) gene. The APC protein is an important skeletal protein of the β-catenin destruction complex. Because of this, it is known that active β-catenin accumulates Wnt-independently in cells with APC gene mutation and it initiates the formation of intestinal tumor.

According to recent studies, the intestinal tumor formation triggered by the APC gene mutation is promoted by the acquisition or inheritance of a mutation in DNA glycosylase, which plays an important role in repair of bases in nucleic acids at the time of oxidative DNA damage. This shows that elevation in the levels of reactive oxygen species (ROS) is involved in the APC mutation-inducible intestinal tumor formation.

Peroxiredoxin (Prx) are known as peroxidases of hydrogen peroxide and alkyl hydroperoxide in vivo (Chae, H. Z. et al., *Proc. Nat. Acad Sci.* 91: 7017-7021, 1994). Peroxiredoxin are classified as types I to VI of Prx isozymes in mammals and are found in various parts of tissues (Rhee, S G et al., *IUBMB Life* 52: 35-41, 2001).

Peroxiredoxin (Prx) are known to exhibit a strong antioxidant activity in cells. Most of the peroxiredoxin isoenzymes, except for Prx type VI, use thioredoxin as an electron donor, and thus, they are known as a thioredoxin peroxidase.

Prx family consists of six isozymes divided into 2-Cys (cysteine) and 1-Cys (cysteine) subfamilies. The 2-Cys subfamily enzymes are thioredoxin-dependent peroxidases that are widely conserved from bacteria to humans. Among the 2-Cys Prx, cytoplasmic PrxI and PrxII isozymes are known to be overexpressed in various types of cancer and play an important regulatory role in membrane receptor-mediated signal transduction.

Mammalian 2-Cys Prx enzymes receive electrons from an electron-conveying system, which consists of thioredoxin-thioredoxin reductase, and reduce hydrogen peroxide ($H_2O_2$) to water in the presence of nicotinamide adenine dinucleotide phosphate (NADPH).

Hydrogen peroxide regulates the reversible oxidation of signal transduction proteins, including protein kinases and protein tyrosine phosphatase. Therefore, hydrogen peroxide functions as a potential secondary messenger in proliferating cancer cells. PrxII is known to regulate hydrogen peroxide locally. Therefore, PrxII, a 2-Cys Prx enzyme, is thought to play a multifaceted role in intracellular ROS detoxification and signal transduction.

Tankyrase (hereinafter, TNKS) is a type of poly(ADP-ribose) polymerase. In CRC cells, the activity of tankyrase induces abnormal cell proliferation by inhibiting β-catenin degradation. Therefore, inhibition of TNKS has been highlighted as a target for treating CRC, but there is a concern that direct inhibition of TNKS may cause pleiotropic effects or side effects due to the presence of a wide range of substrates. In addition, the specific details of the mechanism that regulates the activity of TNKS in CRC tumor formation are not yet known.

The axis inhibitor protein (Axin1), tumor suppressor, is another skeletal protein that constitutes the β-catenin destruction complex. The regulatory mechanism of Axin1 protein by TNKS in APC-mutant cells has not been elucidated. In addition, the treatment of CRC, which regulates the activity of TNKS through the control of the redox system in vivo, has not been attempted until now.

SUMMARY OF THE PRESENT INVENTION

To solve the above-described problems in related art, an object of the present invention is to the mechanism on how peroxiredoxin 2 (PrxII) (which plays a multifaceted role in redox system and signal transduction in APC-mutant cells) regulates the activity of TNKS, and provides a novel pharmaceutical composition for treating CRC that can inhibit CRC by inhibiting the enzyme activity of PrxII by such a mechanism.

To solve the above-described problems in related art, in an embodiment of the present invention provides a pharmaceutical composition for treating CRC comprising a material inhibiting the enzyme activity of PrxII as an active ingredient.

In the pharmaceutical composition for treating CRC by the present invention, the material that inhibits the enzyme activity of PrxII is represented by the following Formula 1.

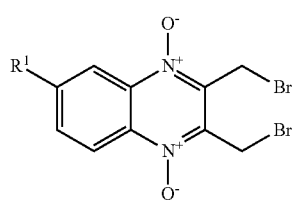

[Formula 1]

In Formula 1 above, $R^1$ is —O—$R^2$, a cyclic compound, or a compound consisting of H; and $R^2$ is at least one selected from the group consisting of a $C_1$ to $C_8$, a branched or unbranched alkyl, alkenyl or alkynyl, and an aromatic or non-aromatic cyclic compound which is substituted or unsubstituted.

In the pharmaceutical composition for treating CRC by the present invention, the material inhibiting the enzyme activity of PrxII may include at least one compound selected from the group consisting of Compound-1 to Compound-6 shown below.

Compound-1

Compound-2

Compound-3

Compound-4

Compound-5

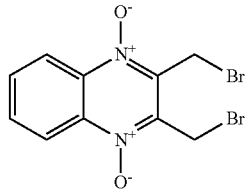

Compound-6

In the pharmaceutical composition for treating CRC by the present invention, the material inhibiting the enzyme activity of PrxII is characterized in that it increases the degradation of β-catenin.

In the pharmaceutical composition for treating CRC by the present invention, the material inhibiting the enzyme activity of PrxII is characterized in that it decreases the degradation of Axin1 by TNKS.

In the pharmaceutical composition for treating CRC by the present invention, the material inhibiting the enzyme activity of PrxII is characterized in that it increases the oxidative inactivation of TNKS.

In the pharmaceutical composition for treating CRC by the present invention, the oxidative inactivation of TNKS occurs in the cytoplasm of an APC-mutant cell.

In the pharmaceutical composition for treating CRC by the present invention, the material inhibiting the enzyme activity of PrxII is characterized in that it decreases the interaction between PrxII and TNKS.

The pharmaceutical composition for treating CRC by the present invention is characterized in that it contains the material inhibiting the enzyme activity of PrxI in a pharmaceutically effective amount. As used herein, the term "pharmaceutically effective amount" refers to an amount which is sufficient to achieve the efficacy or activity of the material inhibiting the enzyme activity of PrxII.

The pharmaceutically acceptable carriers that can be included in the pharmaceutical composition are those commonly used in the preparation of formulations, and these pharmaceutically acceptable carriers may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate, mineral oil, etc. but are not limited thereto.

The pharmaceutical composition may further include lubricants, wetting agents, sweeteners, flavoring agents, emulsifiers, suspending agents, preservatives, etc. in addition to the above components. Suitable pharmaceutically acceptable carriers and formulations are described in detail in Remington's Pharmaceutical Sciences (19th ed., 1995).

The pharmaceutical composition may be prepared in unit-dose form or formulated through incorporation into a multi-dose container by formulating using a pharmaceutically acceptable carrier and/or excipient, in accordance with methods readily available to one of ordinary skill in the art to which this invention pertains. In particular, the formulations may be in the form of solutions, suspensions, syrups, or emulsions in oils or aqueous media, or in the form of extracts, powders, granules, tablets or capsules, and may further include dispersants or stabilizers.

The features, forms, and advantages of one embodiment of the present invention are set forth in the description below, and in part can be apparent from the description or can be learned by practice of such exemplary embodiments.

Other features, forms, and advantages will be apparent to those skilled in the art from the following description and claims, or may be learned by practicing the embodiments described below.

ADVANTAGEOUS EFFECTS

According to an embodiment of the present invention, a composition, which can reduce colorectal polyps via regulation the redox system of CRC cells by inhibiting the enzyme activity of PrxII and can treat or prevent CRC, can be provided. According to an embodiment of the present invention, a pharmaceutical composition, which can reduce colorectal polyps by reducing the interaction between PrxII and TNKS in the cytoplasm of an APC-mutant cell and can treat or prevent CRC, can be provided. According to an embodiment of the present invention, a method for treating CRC which can inhibit the activity of TNKS by regulation of the intracellular redox system can be provided.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 12 shows images and a graph illustrating the results of the proliferating cells analysis by the fluorescence staining, with anti-bromo uridine (anti-BrdU) antibody in the polyp tissue of a double-mutant mouse prepared according to an embodiment of the present invention.

FIG. 13 shows images and graphs illustrating the results of the proliferating cell analysis by the fluorescence staining, with anti-bromo uridine (anti-BrdU) antibody in the polyp tissue of a double-mutant mouse prepared according to an embodiment of the present invention.

FIG. 20 shows graphs illustrating the results of the PrxII-dependent $H_2O_2$ levels in APC-mutant CRC cells, according to an embodiment of the present invention.

FIGS. 74A and 74B show the results of RKO cell colony culture experiments in Conoidin A and Compound-1 to Compound-5 according to an embodiment of the present invention.

FIGS. 75A and 75B show the results of HT29 cell colony culture experiments in Conoidin A and Compound-1 to Compound-5 according to an embodiment of the present invention.

MODE FOR CARRYING OUT THE INVENTION

Figure 1:
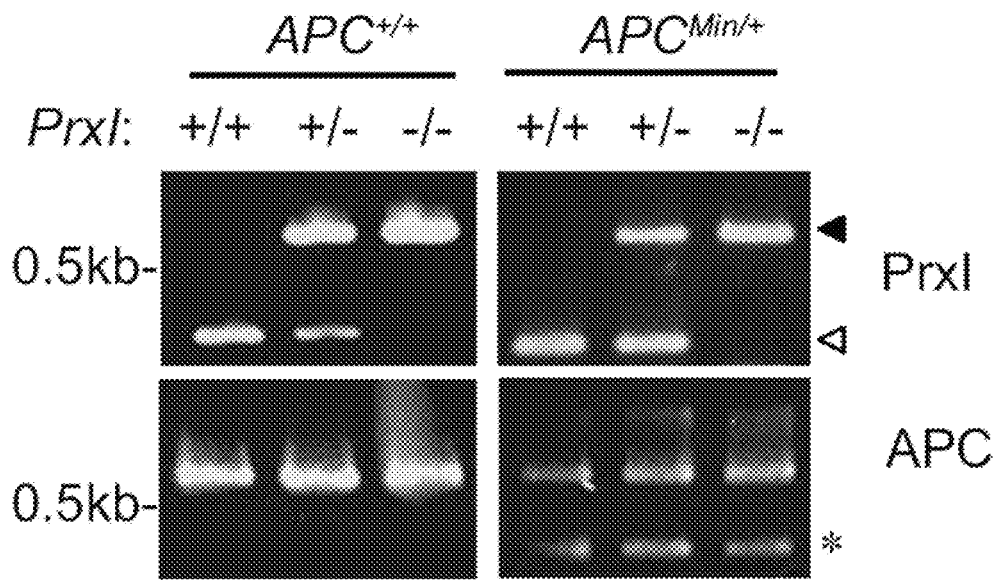
FIGS. 1 and 2 show images illustrating the results of confirming the genotype of a double-mutant mouse prepared according to an embodiment of the present invention.

The advantages and features of the present invention, and a method of achieving the same will be apparent with reference to the following Examples to be described hereinbelow in conjunction with the accompanying drawings. However, these Examples are intended to illustrate the present invention in more detail, and the scope of the present invention is not limited by the following Examples.

Throughout the specification, when a part includes a certain component, this means that it may further include other components rather than excluding other components, unless otherwise specified.

As used herein, the terms Compound-1 to Compound-6 refer to the materials shown in Table 1 below.

| Compound-1 | 2,3-bis(bromomethyl)-6-methoxyquinoxaline 1,4-dioxide | |
|---|---|---|
| Compound-2 | 2,3-bis(bromomethyl)-6-ethoxyquinoxaline 1,4-dioxide | |
| Compound-3 | 2,3-bis(bromomethyl)-6-isopropoxyquinoxaline 1,4-dioxide | |
| Compound-4 | 6-(alloyloxy)-2,3-bis(bromomethyl)quinoxaline 1,4-dioxide | |
| Compound-5 | 2,3-bis(bromomethyl)-6-(prop-2-ynyloxy)quinoxaline 1,4-dioxide | |

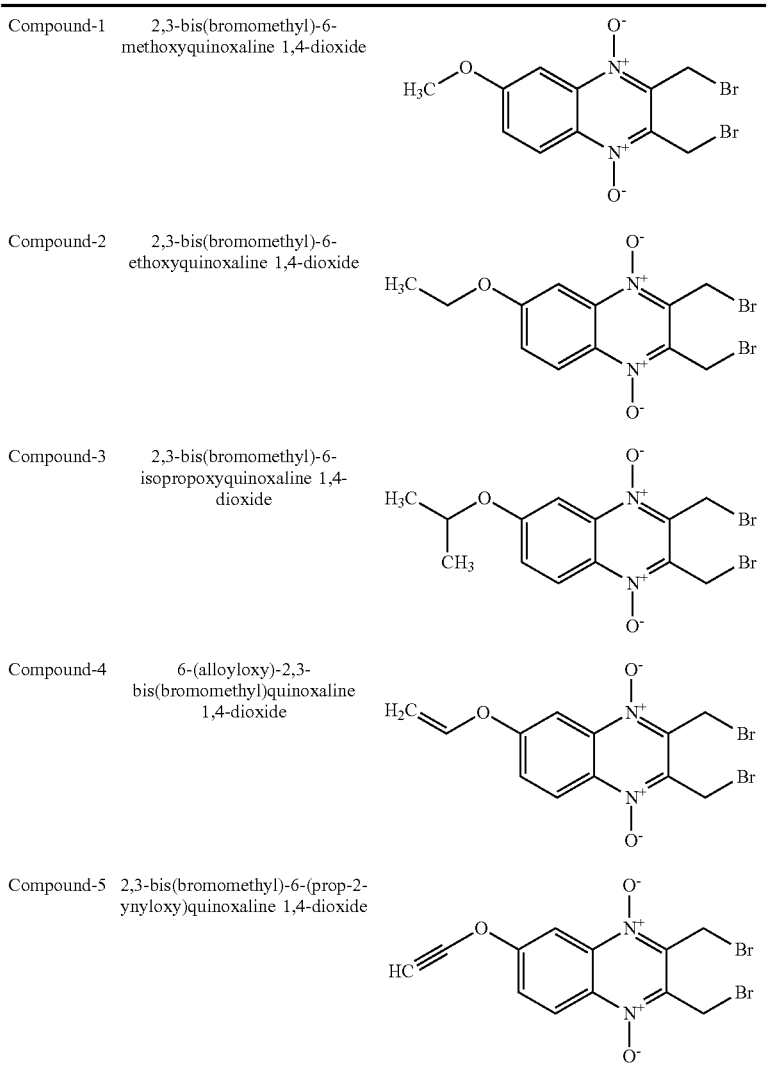

| Compound-6 | 2,3-bis(bromomethyl)quinoxaline 1,4-dioxide | 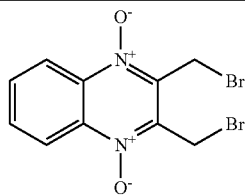 |
|---|---|---|

<Example 1> Cell Culture

All CRC and HEK293 cells were provided by the American Type Culture Collection (Manassas, Va., USA). SW480, DLD1, CoLo205, Colo741, and SW620 cells were subcultured in RPMI 1840 medium supplemented with 10% fetal bovine serum.

HEK293 and RKO cells were cultured in Dulbecco's Modified Eagle's Medium with 10% FBS. HT29 cells were cultured in McCoy's 5A medium with 10% FBS. Mycoplasma contamination was periodically tested in cell culture supernatants using the mycoplasma detection kit (Biotool, USA).

<Example 2> Preparation of Double-Mutant Mice

To test the CRC-specific function of PrxII in wivo, double-mutant mice were prepared by crossing $PrxI^{+/-}$ and $PrxII^{+/-}$ mice with $APC^{Min/+}$ mice.

$PrxI^{+/-}$ and $PrxII^{+/-}$ C57BL/6 mice were crossed with $APC^{Min/+}$ mice according to the C57B/6 background (Jackson Laboratory, Bar Harbor, USA), bred and maintained in aseptic facilities, and thereby complex mutants representing the genotypes of $APC^{Min/+};PrxI^{-/-}$, $APC^{Min/+};PrxI^{+/-}$, $APC^{Min/+};PrxI^{-/-}$, $APC^{Min/+};PrxII^{+/-}$, $APC^{Min/+};PrxII^{-/-}$, and $APC^{Min/+};PrxII^{-/-}$ were prepared.

The genotypes of the littermates were confirmed by performing genomic PCR for mouse tail DNA using specific primers therefor. The littermates refers to babies born from the same mother.

All mouse experiments were approved by the Institutional Animal Care and Use Committee (IACUC) of Ewha Womans University and performed in compliance with the ARRIVE guidelines. Animal experiments were performed by a double-blind test after separation of animal breeding and tissue analysis.

In the case of a tumor xenograft model, the mice were anesthetized by the inhalation of isoflurane gas ($N_2O:O_2$/70%:30%) and subcutaneously injected with HT29-luc2 cells ($2.5 \times 10^5$ cells) suspended in 200 μL of PBS. Compound 1 to Compound 6 (286 μM in DMSO) were intraperitoneal administered starting from 6 days after the cell injection and repeated every 3 days.

Bioluminescent imaging was performed with IVIS Lumina Series III (Perkin Elmer). For each image photographing session, luciferin suspended in PBS (150 mg of luciferin/kg body weight) was administered intraperitoneally according to the manufacturer's protocol.

Up to four animals were maintained in the integral anesthetic manifold equipment and they were imaged 10 minutes after luciferin injection. The IVIS imaging system collects the photographic images of mice and quantitative bioluminescent signals therefrom and then allows them to overlap with each another.

<Example 3> Genotyping of Double-Mutant Mice

Figure 2:
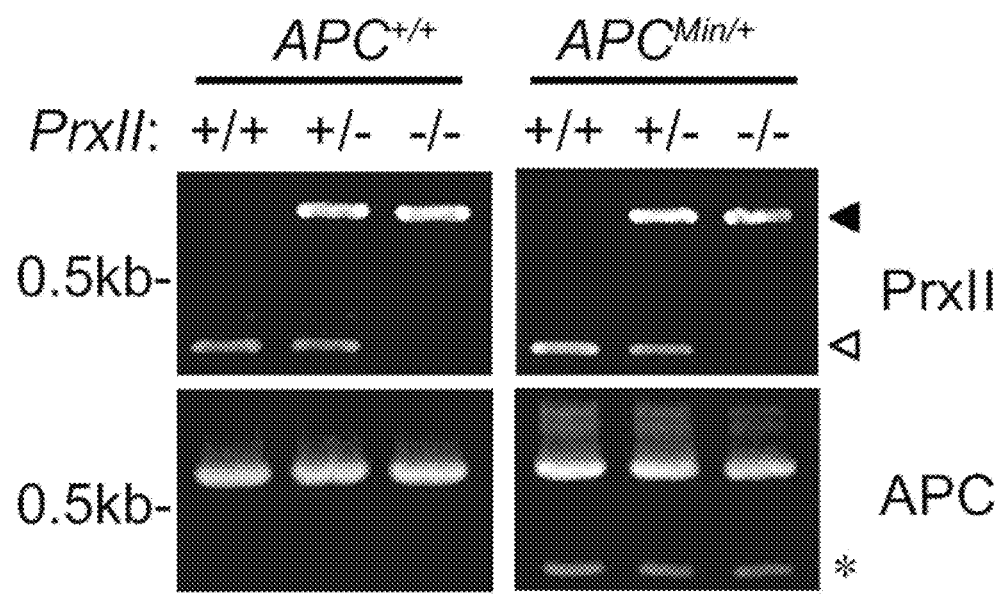

The genotypes of the mice, to which a double mutation was induced, prepared in Examples above were determined by performing genomic PCR at Week 4, and the resulting genotypes of the double-mutant mice prepared in Examples above are shown in FIGS. 1 and 2.

Figure 3:
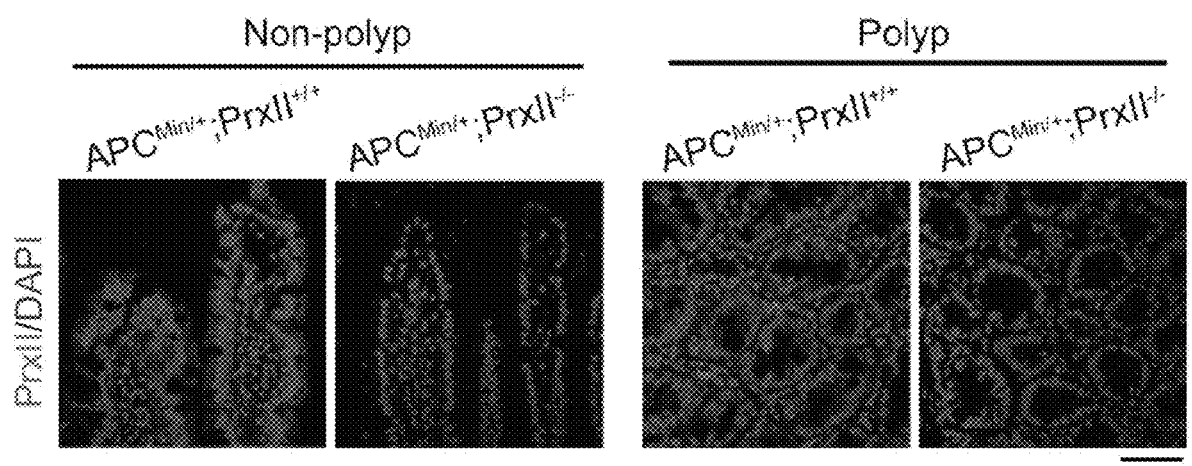
FIG. 3 shows images illustrating the results of PrxII protein expression by immunofluorescence staining in non-polyp segments and polyps of the small intestine according to an embodiment of the present invention.

In FIGS. 1 to 3, it confirmed that the double mutant mice prepared in Examples above can develop multiple intestinal neoplasia (Min) by a truncation mutation of adenomatous polyposis coli (APC). The products of the truncated APC gene in FIGS. 1 and 2 are indicated by asterisks.

Although APC mutations are heterozygous, intestinal adenomatous polyposis is known to be caused by loss of residual APC wild type (WT), and the resulting adenomatous polyposis is known to include a truncated APC wild type (WT) copy similar to that of human CRC tumor.

The primers used to determine genotypes are as follows.

```
APC^Min
(wild type)
                                    (SEQ ID NO: 1)
5'-GCCATCCCTTCACGTTAG-3'

(mutant)
                                    (SEQ ID NO: 2)
5'-TTCTGAGAAAGACAGAAGTTA-3'

(common)
                                    (SEQ ID NO: 3)
5'-TTCCACTTTGGCATAAGGC-3'

PrxI
forward
                                    (SEQ ID NO. 4)
5'-CTGGAAACCTGGCAGTGATA-3' reverse,
                                    (SEQ ID NO: 5)
5'-CTGTGACTGATAGAAGATTGGT-3'

PrxII
forward,
                                    (SEQ ID NO. 6)
5'-GATGATCTCCGTGGGGCAAACAAA-3' reverse,
                                    (SEQ ID NO: 7)
5'-ATGGCCTCCGGCAACGCGCAAATC-3'

Neo cassette
forward,
                                    (SEQ ID NO. 8)
5'-GCTTGGGTGGAGAGGCTATTCG-3' reverse,
                                    (SEQ ID NO: 9)
5'-GTAAAGCACGAGGAAGCGGTCAGC-3'
```

<Example 4> Observation of Adenomatous Polyps in Double-Mutant Mice

Figure 4:
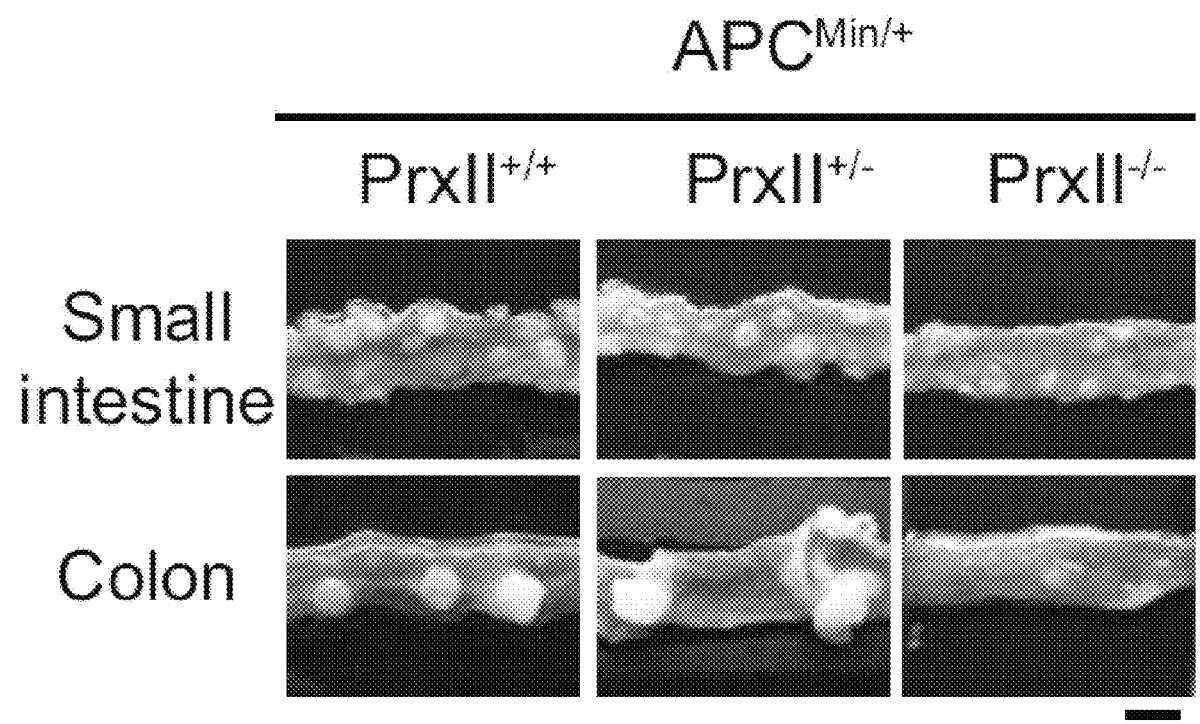
FIG. 4 shows microscopic images illustrating the intestinal tissue of a double-mutant mouse prepared according to an embodiment of the present invention.

The small intestine and colon were excised from the mouse, the adenomatous polyps of the intestine were separated and observed using a stereomicroscope, and the results are shown in FIG. 4.

Figure 5:
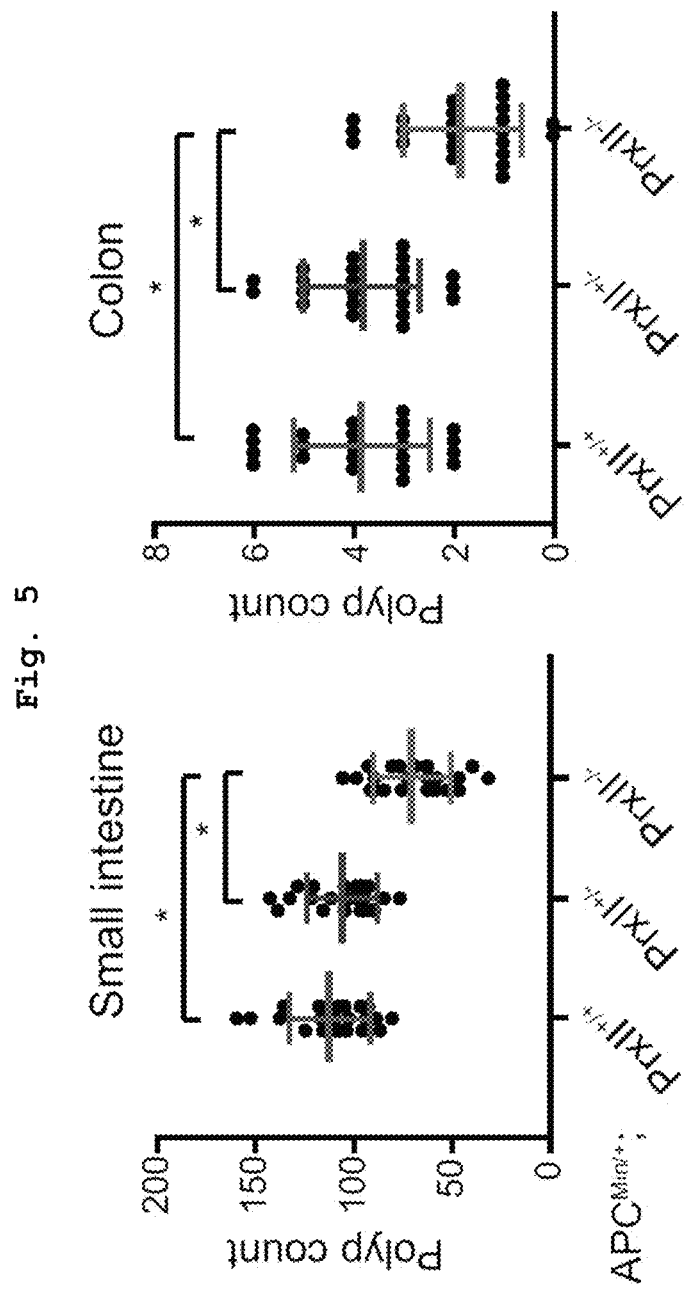
FIG. 5 shows graphs illustrating the number of polyps in the intestinal tissue of a double-mutant mouse prepared according to an embodiment of the present invention.

The number of polyps whose diameter exceeds 0.3 mm in the small intestine and colon of the mice was measured and the results are shown in FIG. 5. As shown in FIG. 5, the average number of polyps greater than 0.3 mm in diameter shown in the small intestine and colon of the APCN$^{Min/+}$; PrxII$^{-/-}$ mouse was decreased by about 50% compared to those shown in the APC$^{Min/+}$;PrxII$^{-/-}$ mouse and the APC$^{Min/+}$;PrxII$^{+/-}$ mouse.

The APC$^{Min/+}$;PrxII$^{-/-}$ mouse (average days of survival=241 days) survived much longer than the APC$^{Min/+}$; PrxII$^{+/+}$ mouse (average days of survival=146 days) and the APC$^{Min/+}$;PrxII$^{+/+}$ mouse (average days of survival=152 days).

Figure 6:
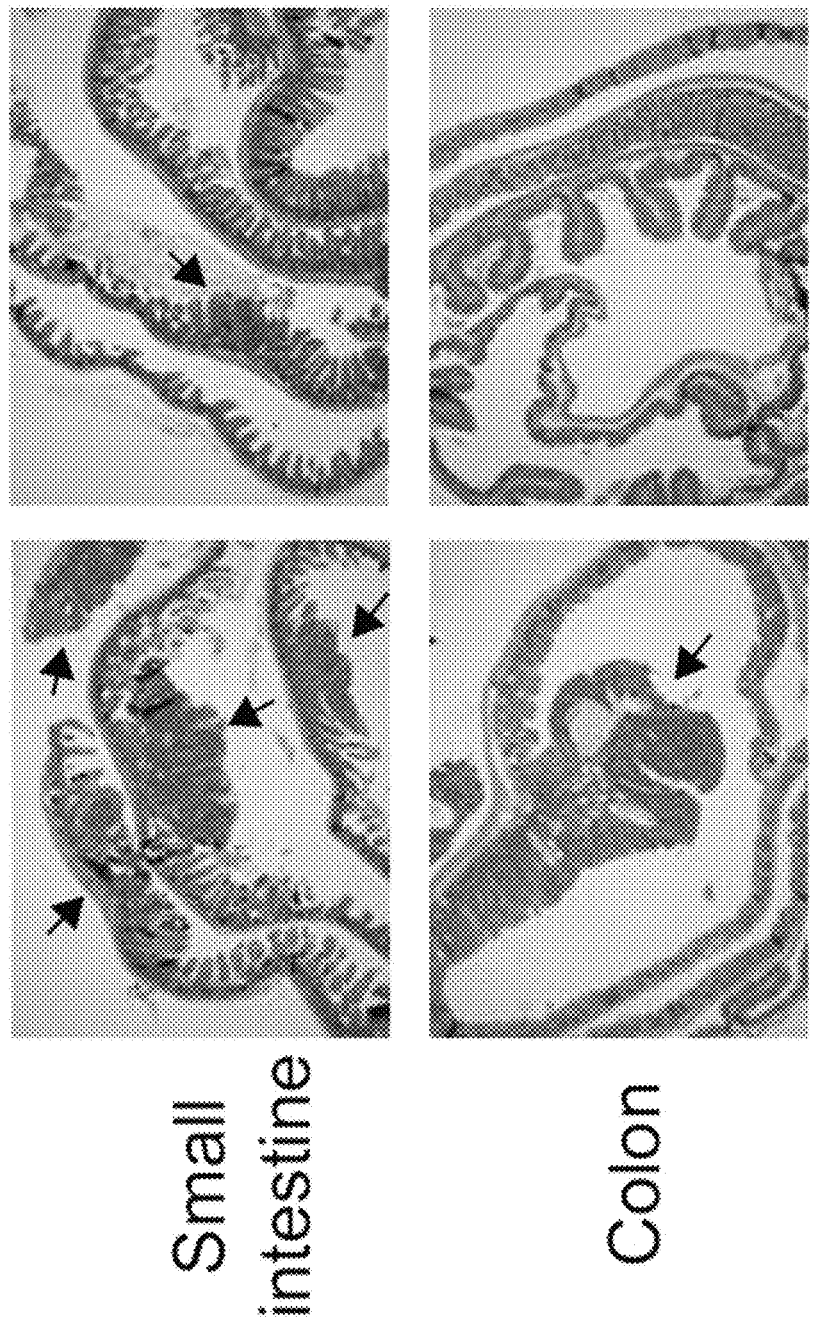
FIG. 6 shows images illustrating the results of staining the cross-sections of the small intestine and colon of a double-mutant mouse prepared according to an embodiment of the present invention with hematoxylin and eosin.

Histological examination of the small and large intestines of the mice was performed and the results are shown in FIG. 6. As shown in FIG. 6, PrxII deficiency did not change the villi structure but decreased the frequency and size of the adenomatous polyps.

Figure 7:
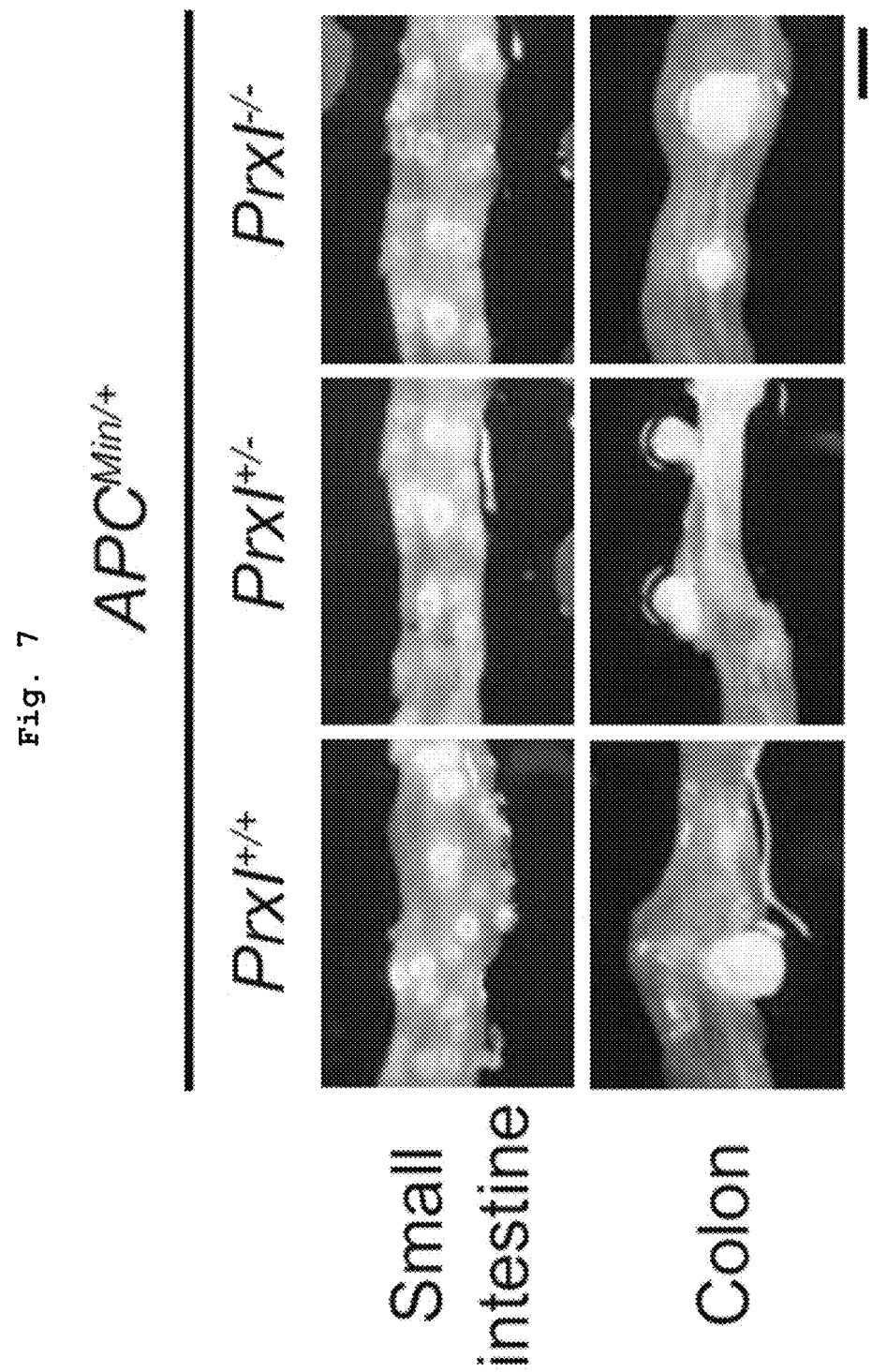
FIG. 7 shows microscopic images illustrating the intestinal tissue of a double-mutant mouse prepared according to an embodiment of the present invention.
Figure 8:
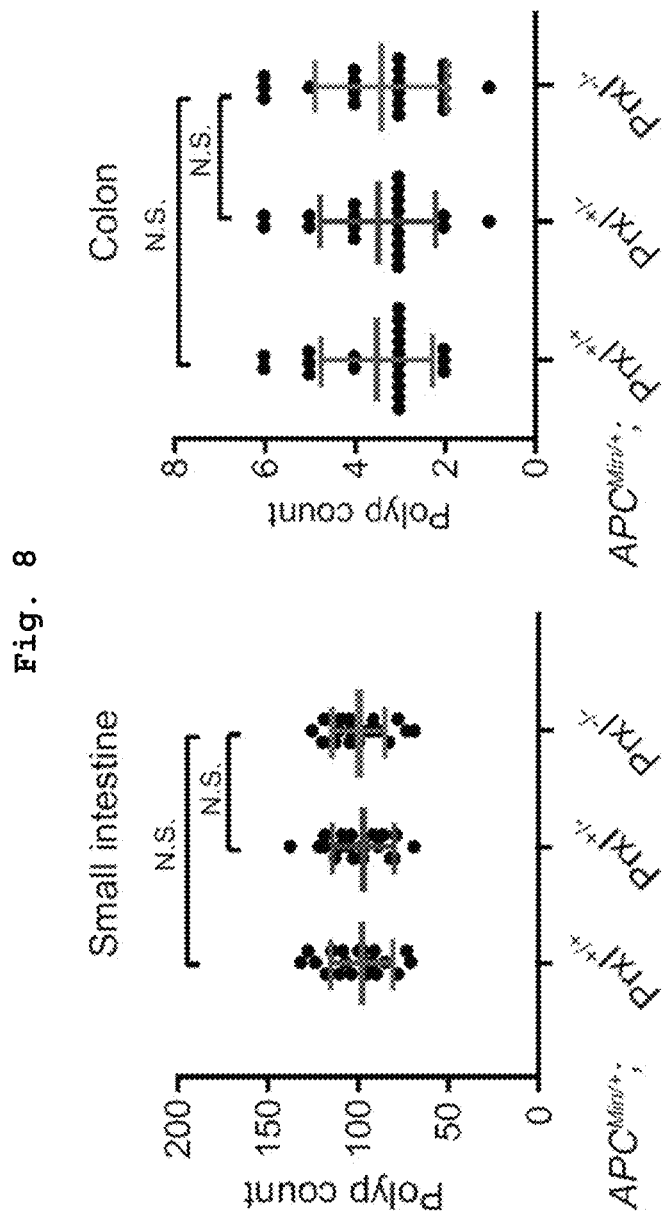
FIG. 8 shows graphs illustrating the number of polyps in the intestinal tissue of a double-mutant mouse prepared according to an embodiment of the present invention.

The intestinal adenomatous polyps of PrxI-deficient mice were observed using a stereomicroscope and the numbers thereof were counted and are shown in FIGS. 7 and 8. The average number of intestinal polyps of the APC$^{Min/+}$;PrxI$^{-/-}$ mouse was the same as those of APC$^{Min/+}$;PrxI$^{+/+}$ mouse and the APC$^{Min/+}$;PrxI$^{+/-}$ mouse.

From the above results, it confirmed that while PrxII promotes intestinal tumor formation induced by an APC mutation in vivo, PrxI is independent of intestinal tumor induced by an APC mutation.

<Example 5> Measurement of β-Catenin Expression

Figure 9:
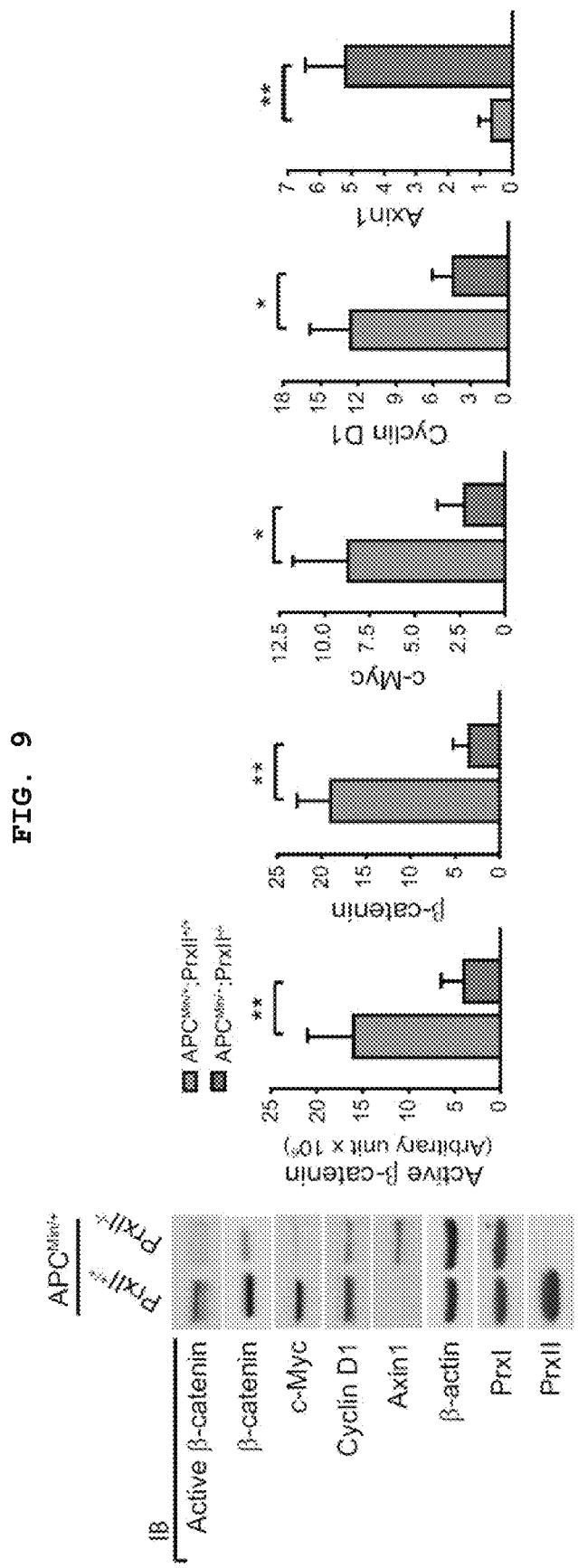
FIG. 9 shows images illustrating the results of immunoblotting performed using an intestinal tissue extract of a double-mutant mouse prepared according to an embodiment of the present invention. Graphs show quantified data of immune-reactive bands.

The expression levels of β-catenin and its gene in the polyps separated from the APC$^{Min/+}$;PrxII$^{+/+}$ mouse and the APC$^{Min/+}$;PrxII$^{-/-}$ mouse were measured by immunoblotting and the results are shown in FIG. 9.

As shown in FIG. 9, the expression levels of β-catenin and its transcription targets (i.e., c-Myc and cyclin D1) in the APC$^{Min/+}$;PrxII$^{-/-}$ tumor were significantly reduced compared to those in the APC$^{Min/+}$;PrxII$^{+/+}$ tumor. However, the expression level of Axin1, an important scaffold protein in the β-catenin destruction complex, increased in APC$^{Min/+}$; PrxII$^{-/-}$ mouse in inverse proportion to tumors.

Figure 10:
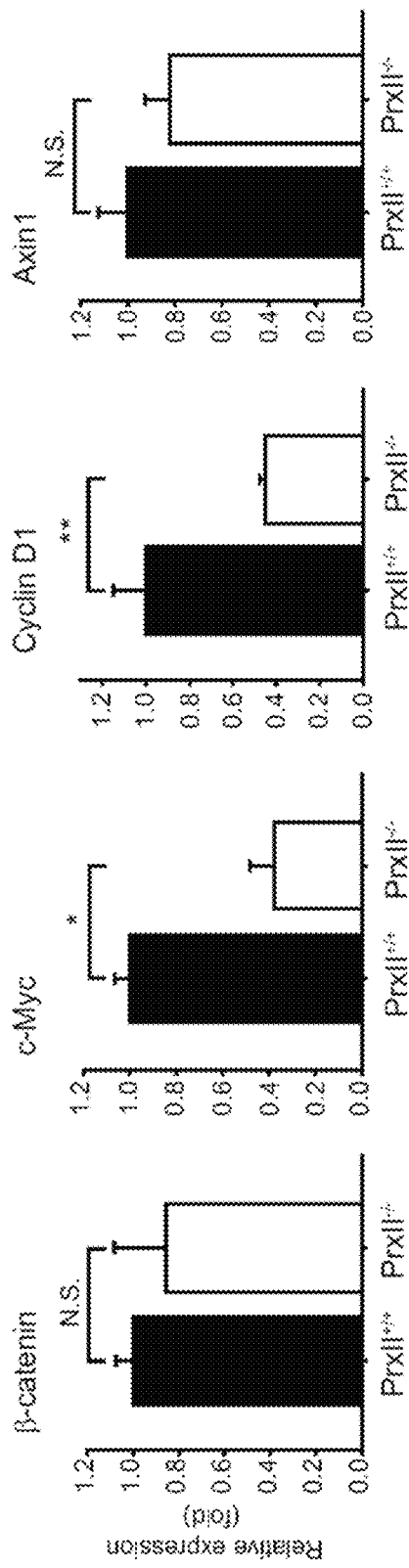
FIG. 10 shows graphs illustrating the results of the expression levels of Axin1, (3-catenin, and β-catenin target genes in the polyp tissue of a double-mutant mouse prepared according to an embodiment of the present invention.

As shown in FIG. 10, since the expression levels of β-catenin and Axin1 mRNA did not change between APC$^{Min/+}$;PrxII$^{+/+}$ and APC$^{Min/+}$;PrxII$^{-/-}$, it confirmed that PrxII regulates the expression of Axin1 and β-catenin at the protein level in vivo.

<Example 6> Determination on Whether β-Catenin Target Genes are Involved in Proliferation and Survival of CRC Cells The number of proliferating cell and dead cells were counted to determine whether β-catenin target genes are involved in the proliferation and survival of CRC cells.

Figure 11:
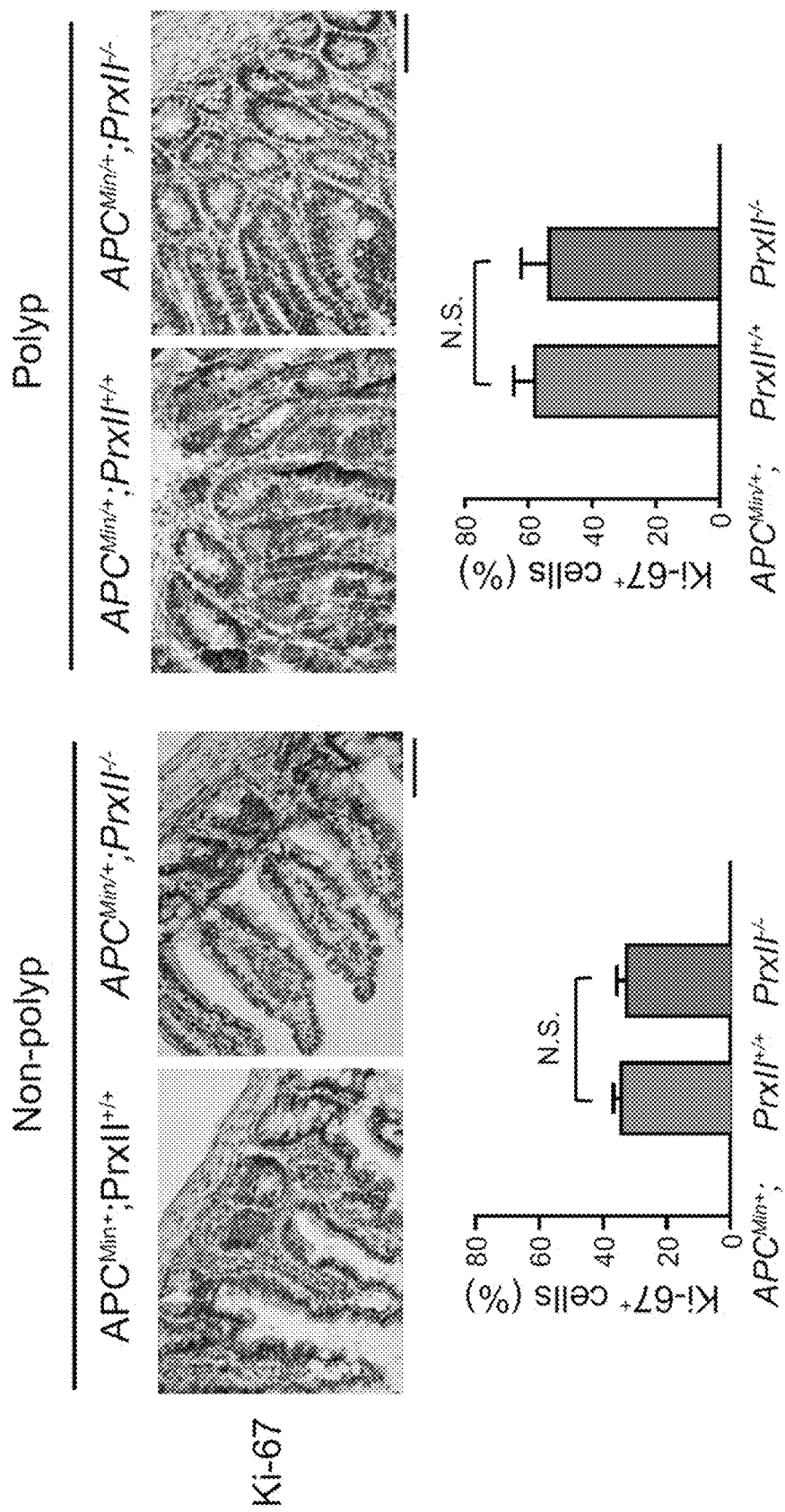
FIG. 11 shows images and graphs illustrating the results of immunohistochemistry image analysis for Ki-67 in the polyp tissue of a double-mutant mouse prepared according to an embodiment of the present invention.

As shown in Ki-67 expression and BrdU incorporation assays in FIGS. 11 and 12, the proportion of proliferating cells was similar in the polyps of APC$^{Min/+}$;PrxII$^{+/+}$ and APC$^{Min/+}$;PrxII$^{-/-}$.

In addition, in FIG. 13, the BrdU incorporation assays showed that PrxII deficiency had no effect at all on the proliferation and migration of intestinal epithelial cells of the scrotum.

Figure 14:
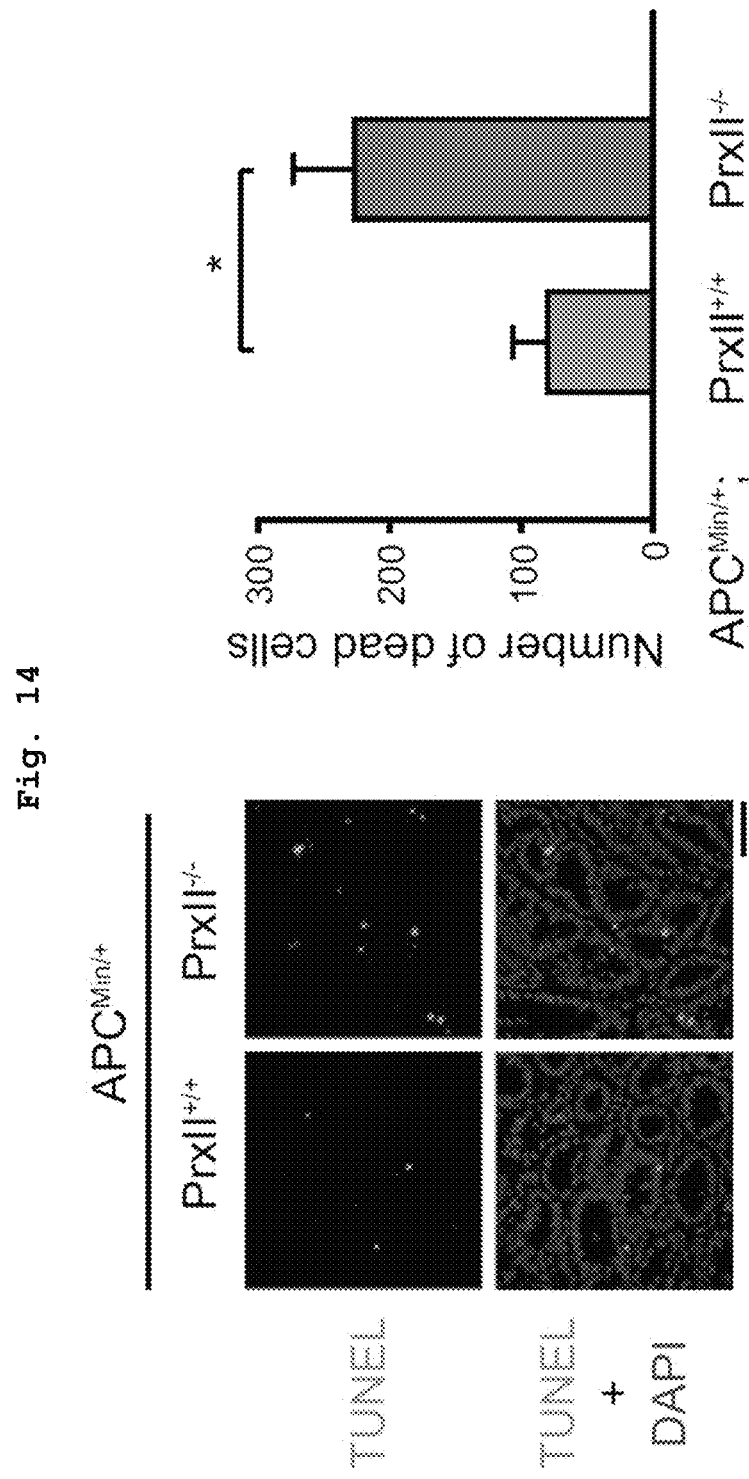
FIG. 14 shows images and a graph illustrating the results of tunnel (TUNEL) staining of the apoptosis in the polyp tissue of a double-mutant mouse prepared according to an embodiment of the present invention.

In contrast, in FIG. 14, the number of dead cells measured by TUNEL staining in the polyp of the APC$^{Min/+}$;PrxII$^{-/-}$ was significantly higher than the number of dead cells measured by TUNEL staining in the polyp of the APC$^{Min/+}$; PrxII$^{+/+}$. These results suggest that PrxII promotes survival of tumor cells in intestinal adenomatous polyps induced by APC mutations.

<Example 7> Analysis of Regulation Mechanism β-Catenin Expression by PrxII

The mechanism of regulating β-catenin expression by PrxII in human CRC cells overexpressing PrxII was analyzed.

Figure 15:
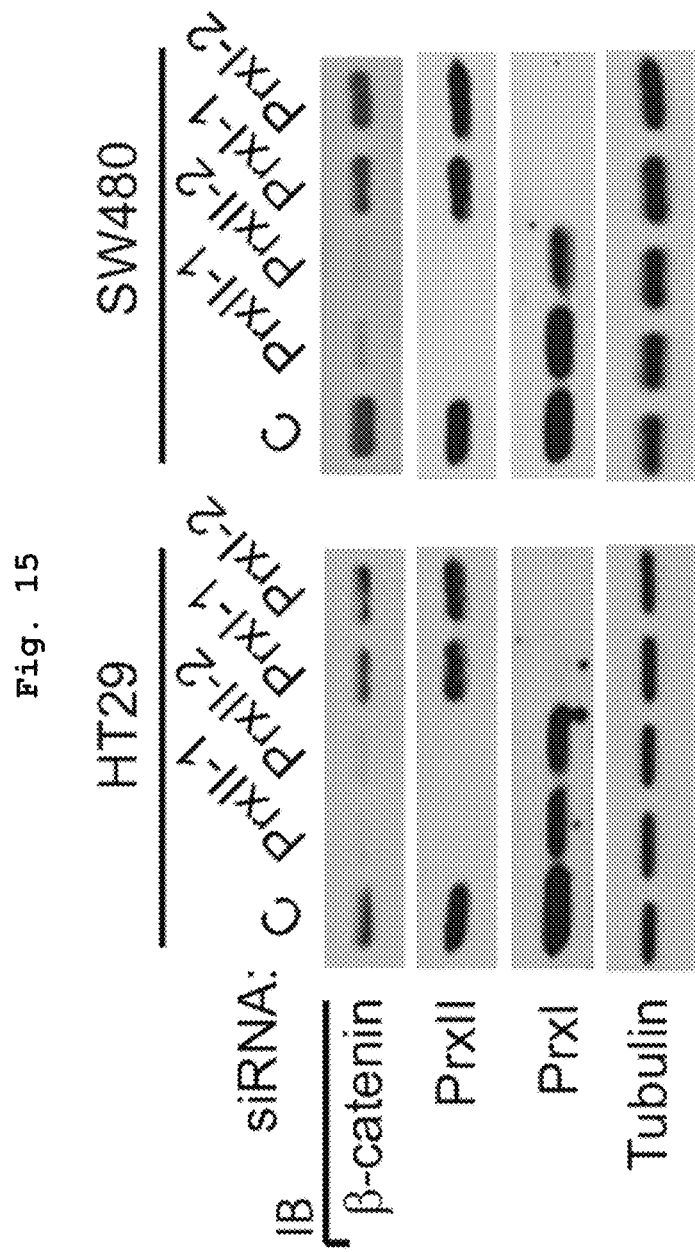
FIG. 15 shows images illustrating the results, in which cells were transfected with a set of siRNAs specific for PrxI and PrxII for 48 hours and immunoblotted against β-catenin, according to an embodiment of the present invention.

As shown in FIG. 15, the siRNA analysis in both APC-mutant CRC cells (i.e., SW480 and HT29 cells) showed that the decrease of PrxII expression resulted in a significant decrease in the expression levels of endogenous β-catenin and expression of a truncated mutant form of APC protein. However, PrxI deficiency did not change the β-catenin expression in both SW480 and HT29 cells.

Figure 16:
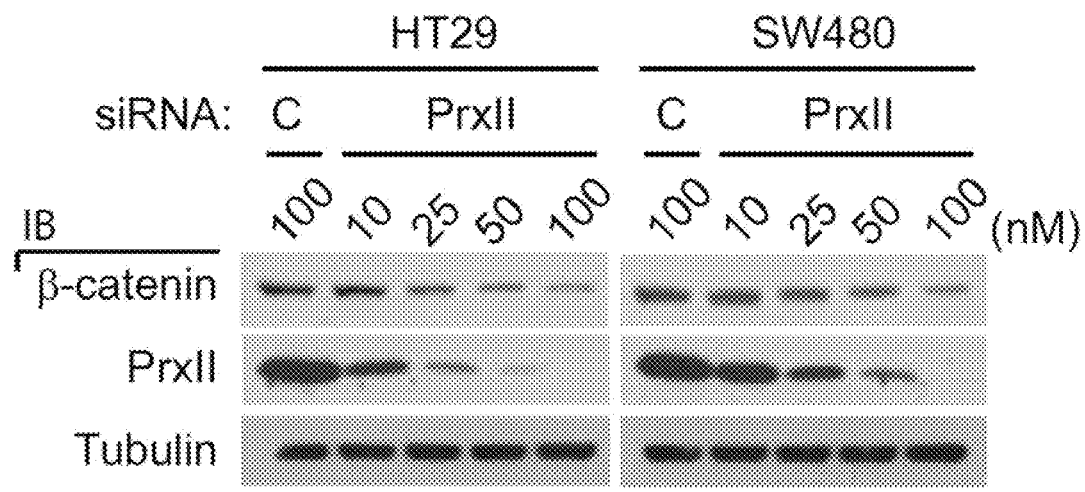
FIG. 16 shows images illustrating the results, in which cells were transfected with PrxII-1 siRNA at various concentrations for 48 hours and immunoblotted against β-catenin, according to an embodiment of the present invention.

In addition, as shown in FIG. 16, the decrease of R-catenin expression is proportional to the degree of PrxII deficiency, and from this result, it was indicated that a strict knockdown of PrxII is important for reducing β-catenin expression level.

Figure 17:
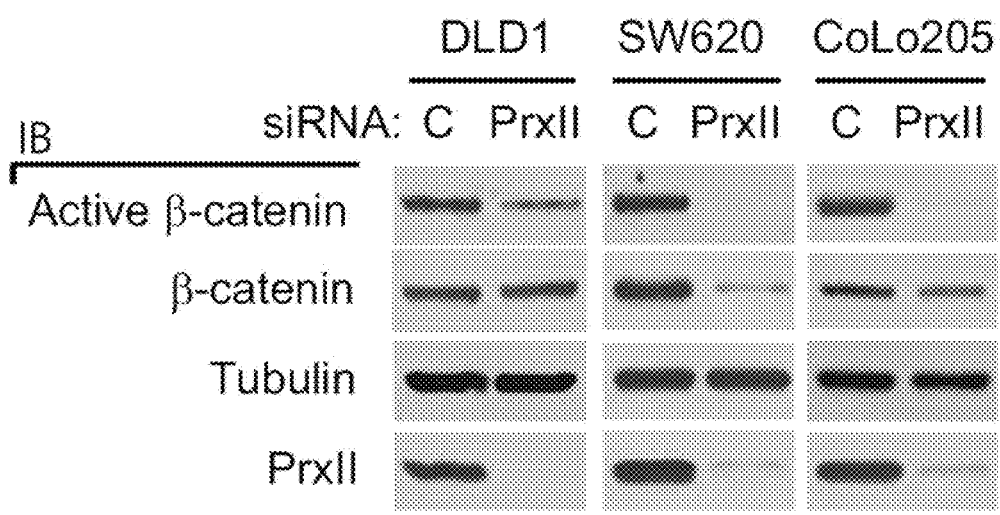
FIG. 17 shows images illustrating the results, in which various APC-mutant colorectal cancer cell (CRC) lines were transfected with PrxII-1 siRNA for 48 hours and immunoblotted against β-catenin and active β-catenin, according to an embodiment of the present invention.

As shown in FIG. 17, PrxII deficiency also reduced the expression levels of total β-catenin and active β-catenin (non-phosphorylated form) in other APC-mutant CRC cells (i.e., SW620, DLD-1, and CoLo205).

To exclude off-target effects of PrxII siRNA, PrxI was expressed by transfecting HT29 cells with PrxII, which is in an siRNA-resistant form.

Figure 18:
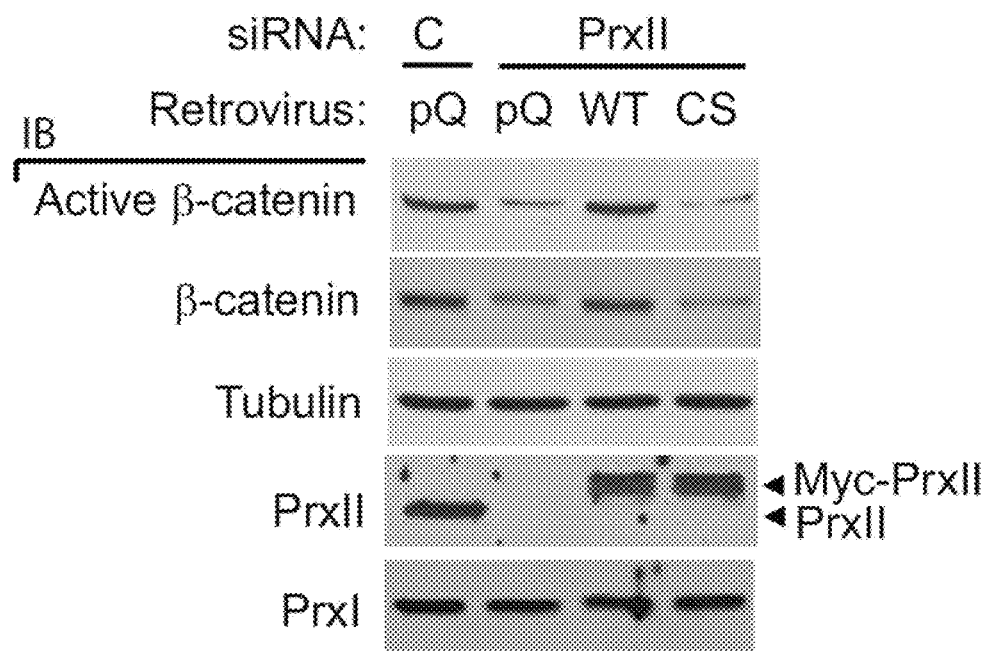
FIGS. 18 and 19 show images illustrating the results, in which various APC-mutant colorectal cancer cell (CRC) lines were transfected with PrxII-1 siRNA for 48 hours, infected again with retroviruses expressing the active (WT) or inactive (CS or C172S) forms of PrxII, and immunoblotted against β-catenin and active β-catenin, according to an embodiment of the present invention.
Figure 19:
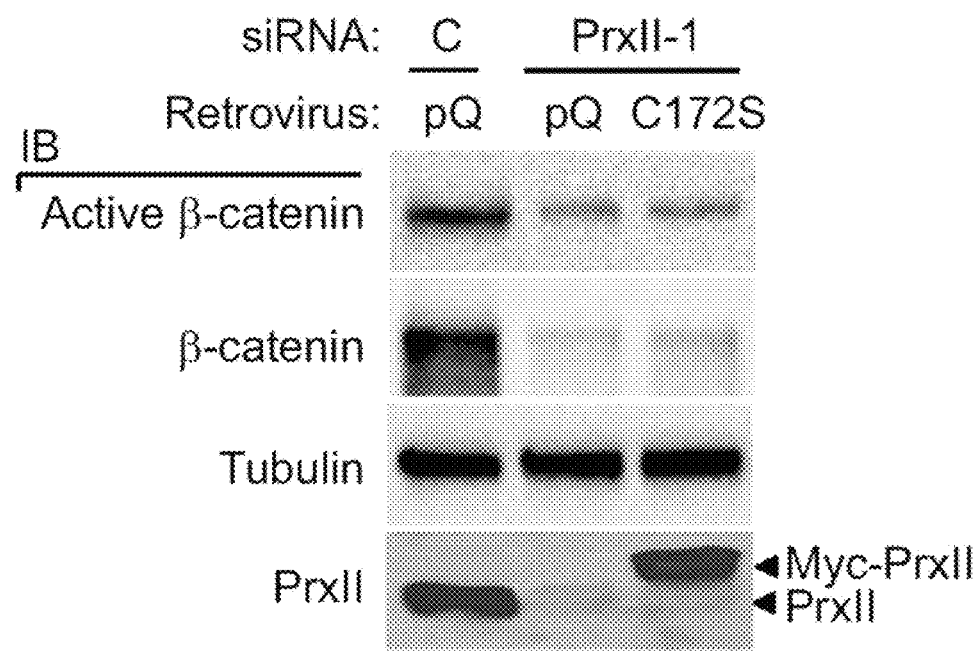

As shown in FIGS. 18 and 19, it confirmed that PrxII wild type (WT) plays a specific role of PrxII that regulates β-catenin expression by fully restoring total β-catenin and active β-catenin expression levels, compared to siRNA-transfected control cells.

In contrast, it confirmed that the expression of PrxII in peroxidase-inactive mutants (i.e., C172S and C51/172S) cannot restore β-catenin expression levels, thus suggesting that peroxidase activity of PrxII is necessary to maintain active β-catenin levels in CRC cells. In FIG. 20, it confirmed that the PrxII deficiency increases the amount of intracellular hydrogen peroxide levels in HT29 and SW480 cells.

Since it was confirmed that PrxII deficiency did not change β-catenin mRNA levels, the degradation of β-catenin protein by a canonical destruction complex, which shows a sequential phosphorylation of β-catenin by casein kinase-1 and glycogen synthase kinase-3β (GSK-3β), was measured.

Since phosphorylated β-catenin is known to be ubiquitonated by an enzyme, which is called β-transducin repeats-containing proteins (β-TrCP) or ubiquitin E3 ligase, and degraded by a porotesome, it was tested whether the β-catenin canonical destruction complex is involved in PrxII-dependent regulation of β-catenin expression.

Figure 21:
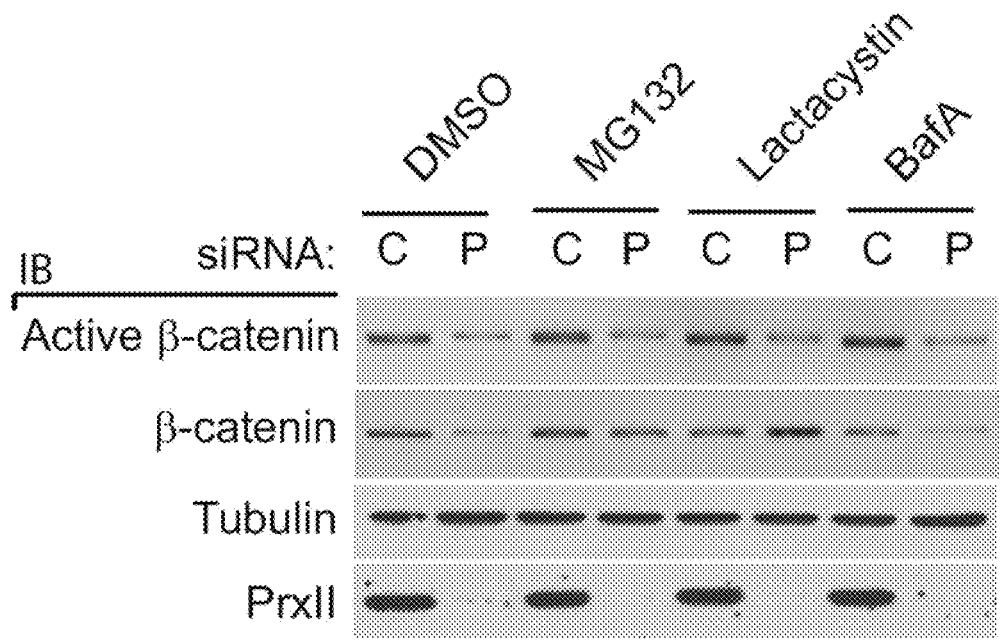
FIGS. 21 to 23 show images confirming that β-catenin destruction complex is involved in CRC, in which a control group according to an embodiment of the present invention and PrxII-deficient colorectal cancer cell (CRC) lines (i.e., SW480 and HT29) were each treated with a proteasome and a glycogen synthase kinase-β (GSK3β) inhibitor (25 μM MG132, lactacystin, 2.5 μM BIO, and SB216763) for one hour, and the expression levels of β-catenin and active β-catenin were measured.
Figure 22:
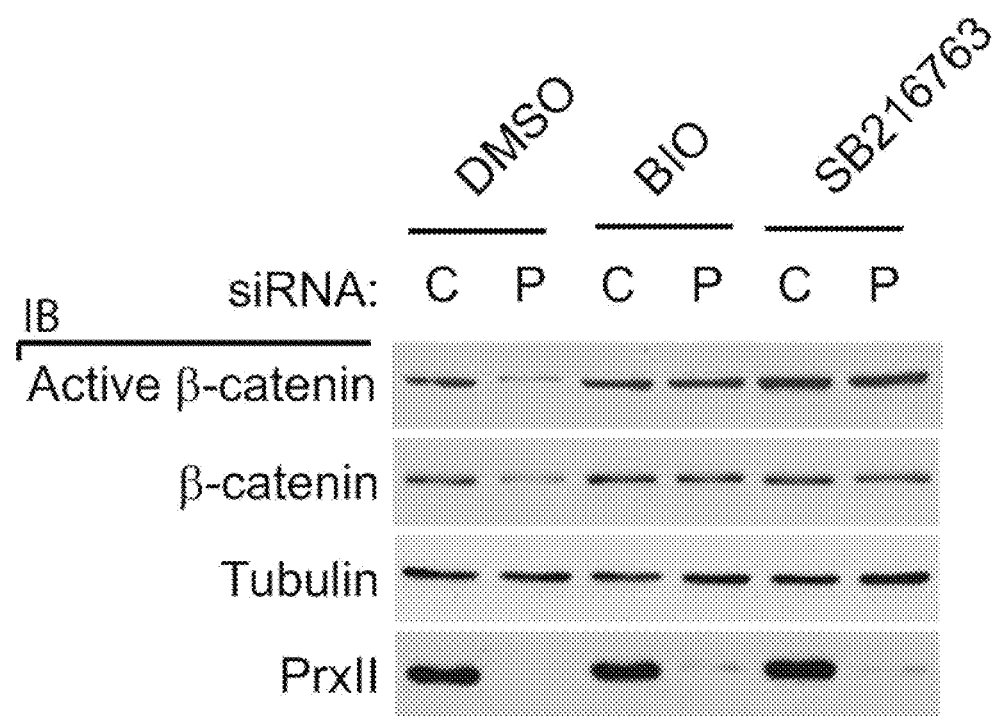
Figure 23:
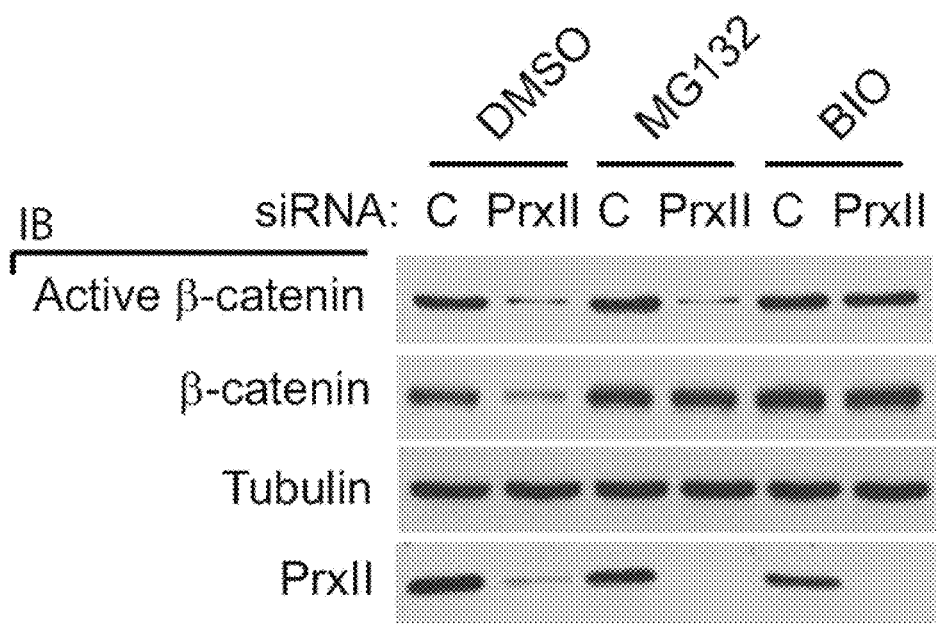

In FIGS. 21 to 23, the GSK-3β inhibitor increased the activity of β-catenin, which indicates that constitutively-active GSK3β is involved therein.

Figure 24:
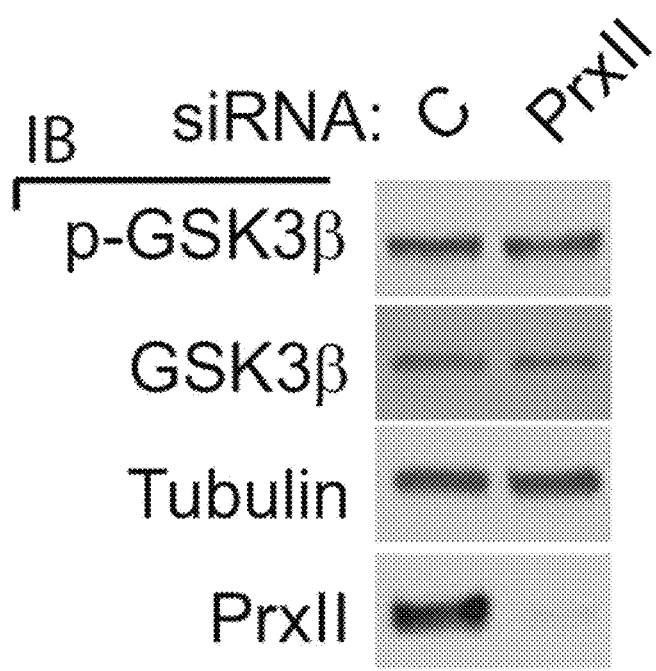
FIG. 24 shows an image confirming that PrxII deficiency does not affect the activation of GSK3β in APC mutant colorectal cancer (CRC) cells according to an embodiment of the present invention.

However, as shown in FIG. 24, it was indicated from the tyrosine phosphorylation level of GSK3β, which is an indicator of kinase activation, that PrxII deficiency is unlikely to stimulate GSK3β activation.

Figure 25:
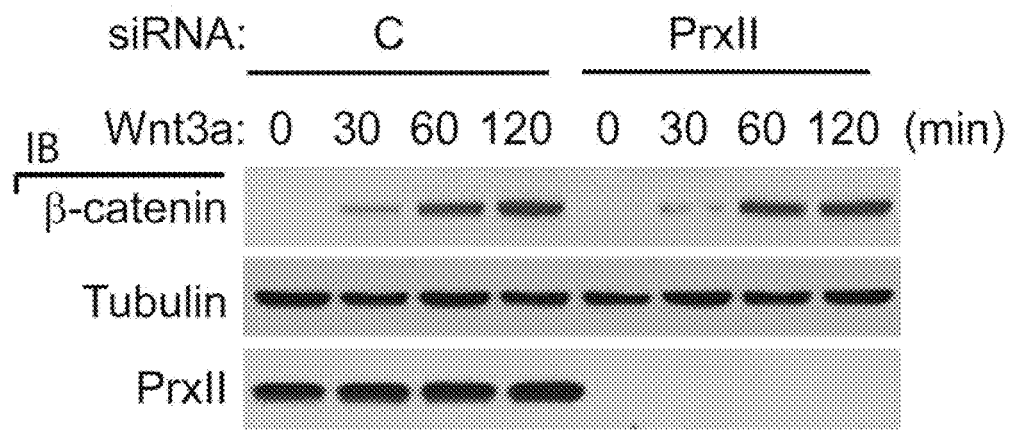
FIG. 25 shows an image confirming that PrxII deficiency does not affect normal Wnt3A signal stimulation in HEK293 cell line according to an embodiment of the present invention.

In addition, in FIG. 25, it was observed that PrxII deficiency does not affect Wnt-induced β-catenin stabilization, and it confirmed that PrxII selectively participates in deregulated β-catenin signaling.

Figure 26:
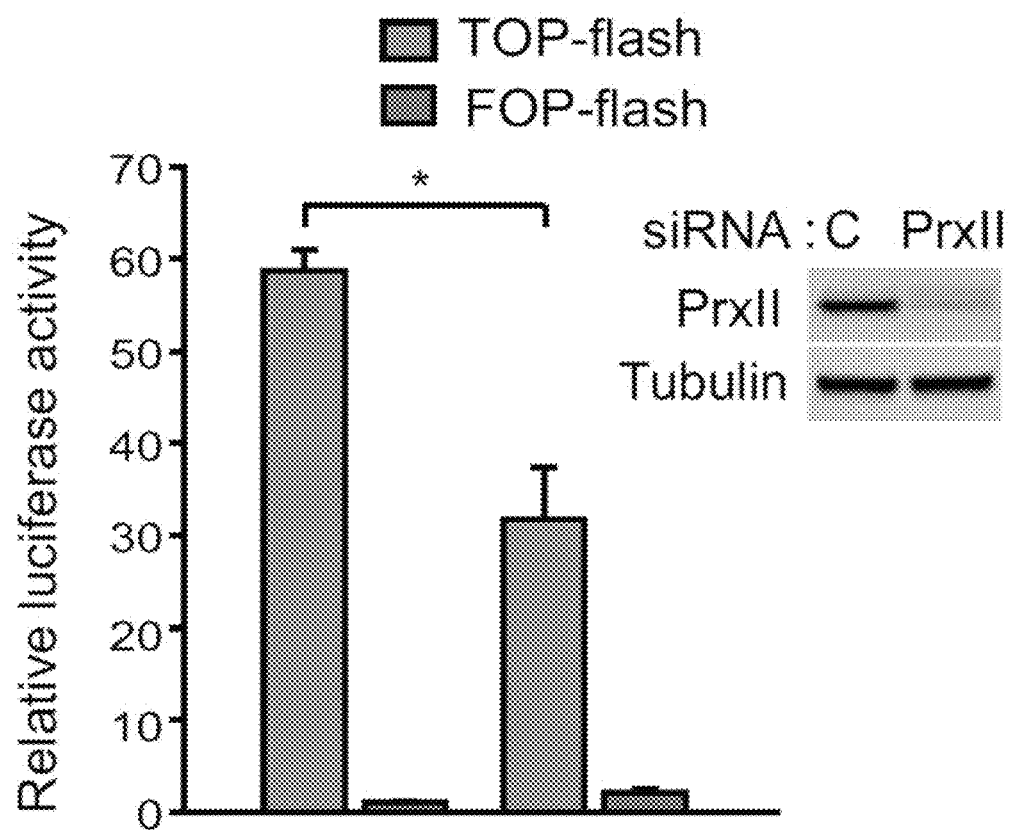
FIG. 26 shows a graph illustrating the results of β-catenin/TCF transcription activity according to an embodiment of the present invention.
Figure 27:
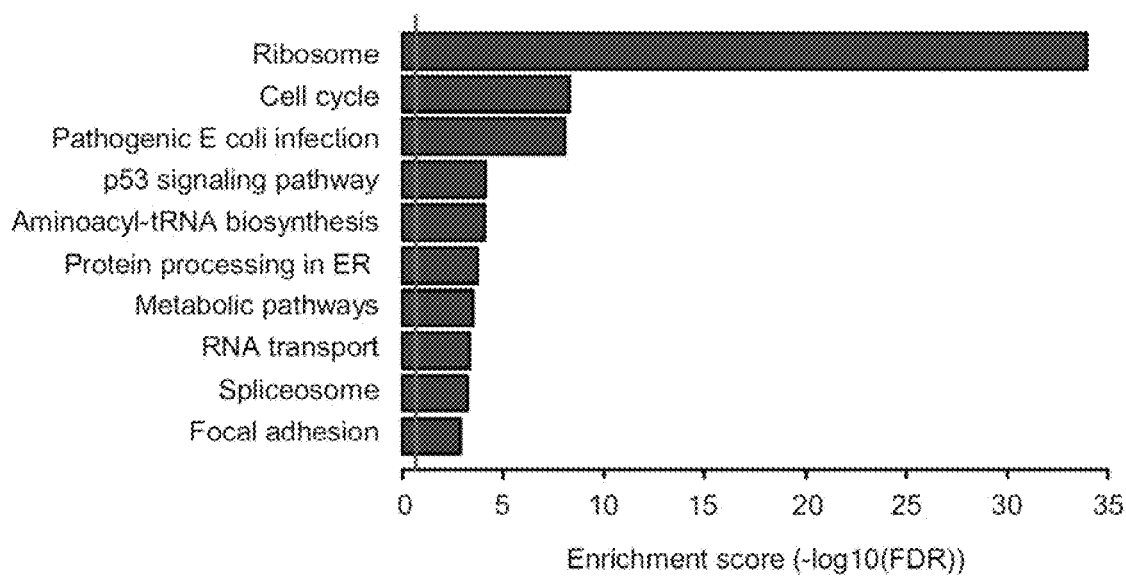
FIGS. 27 to 32 each show an image illustrating the analysis results of genes expressed at different levels in HT29 and SW480 cells due to PrxII deficiency according to an embodiment of the present invention.
Figure 28:
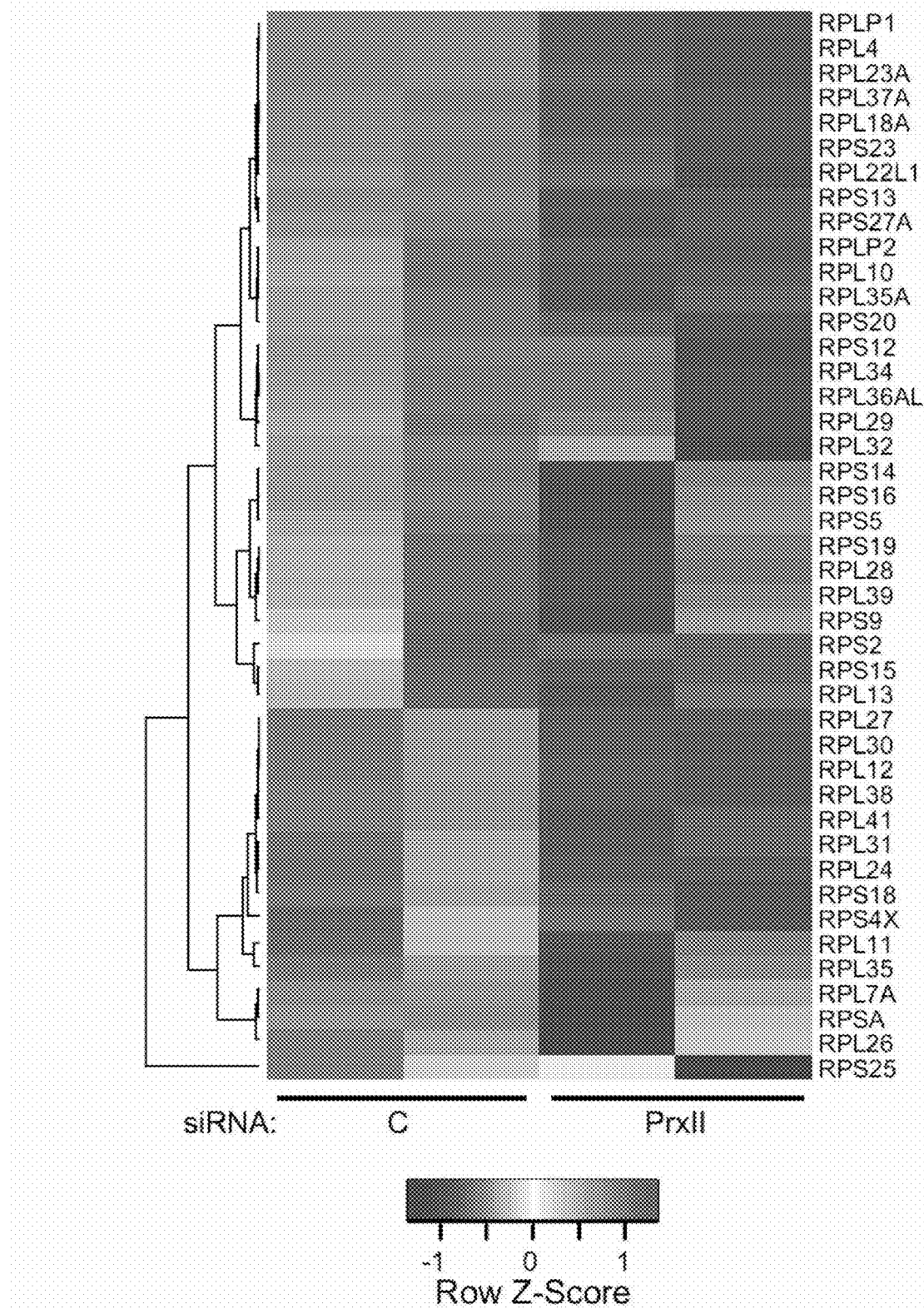
Figure 29:
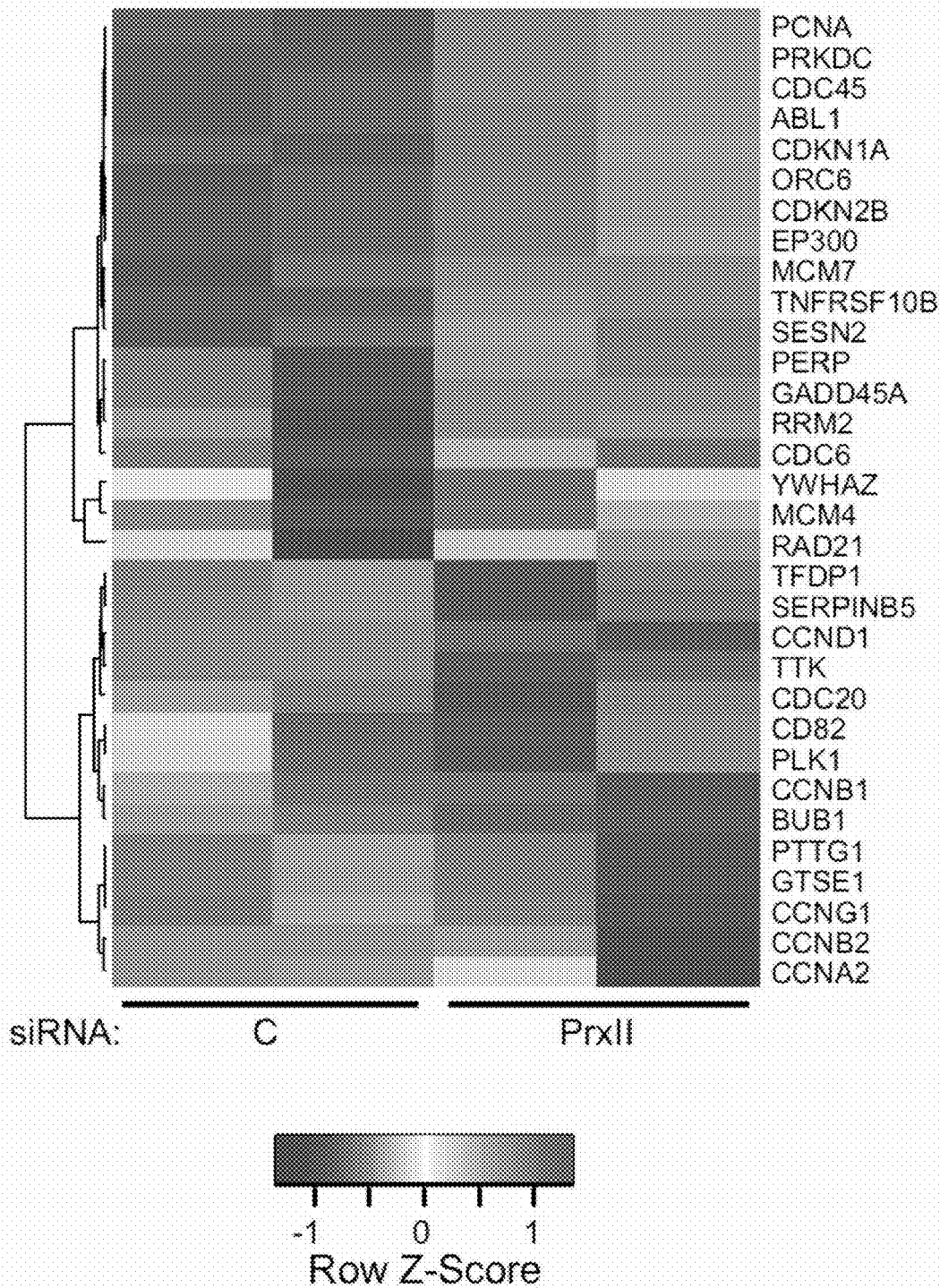
Figure 30:
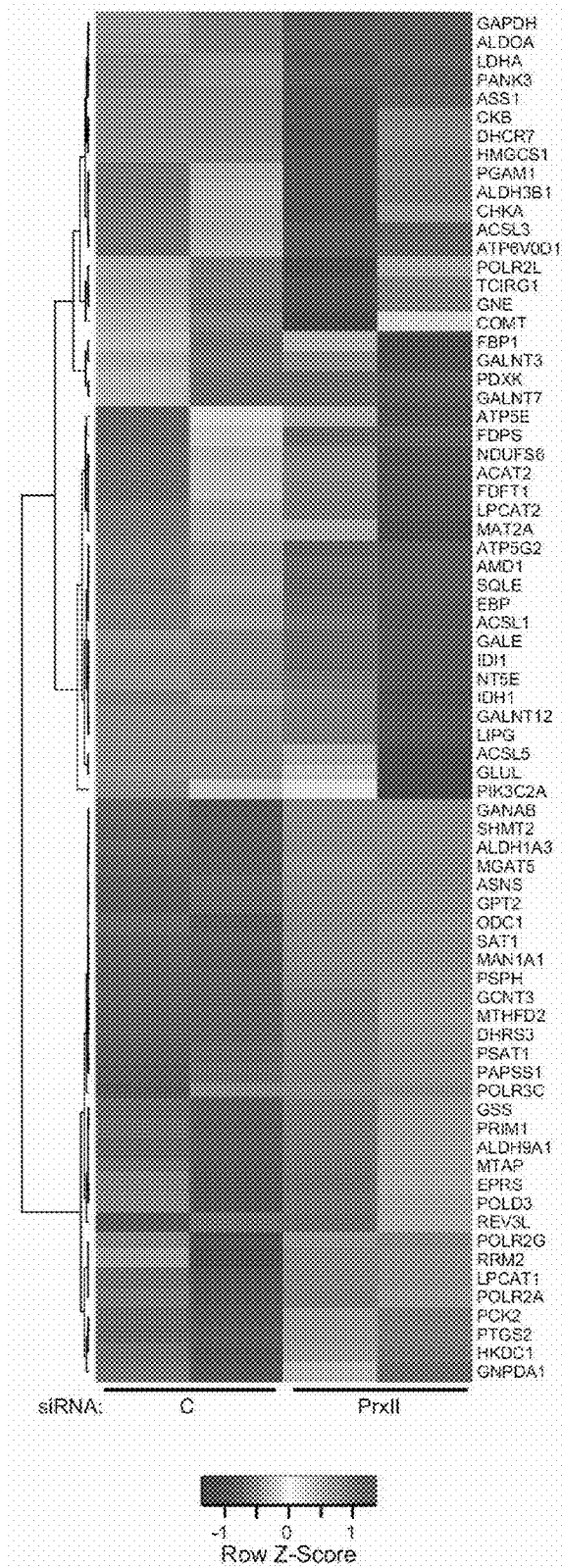

In FIG. 26, as a result of decreased β-catenin expression, PrxII deficiency induced a significant decrease in TCF-dependent reporter expression.

<Example 8> β-Catenin/TCF-Dependent Regulation of Transcription by PrII Deficiency The β-catenin/TCF-dependent transcription in HT29 cells was examined by mRNA sequencing via mRNA sequence analysis and the results are shown in FIGS. 27, 28, 29, and 30.

Figure 31:
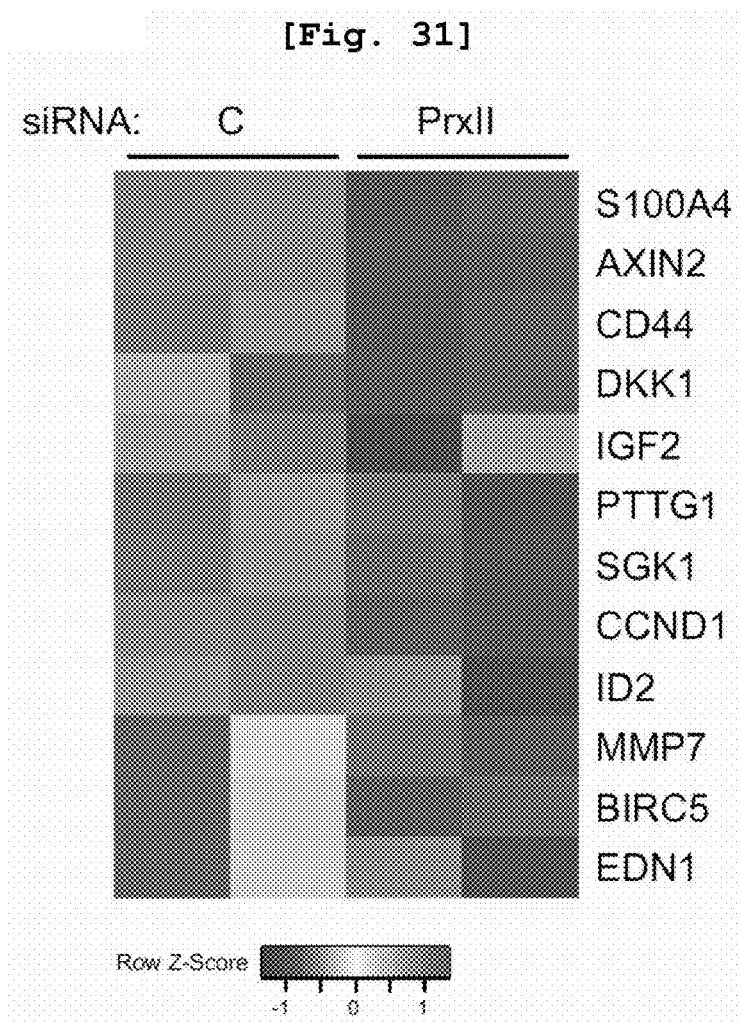

As shown in FIG. 31, in particular, PrxII deficiency downregulated 12 of the β-catenin target genes, which are expressed in CRC cells that include major β-catenin target genes (e.g., CCND1, AXIN2, and BIRC5) (FDR<0.05).

Other metastatic and cell cycle promoting genes (e.g., S100A4, MMP7, ID2, and PTTG1) were also downregulated by PrxII deficiency.

Figure 32:
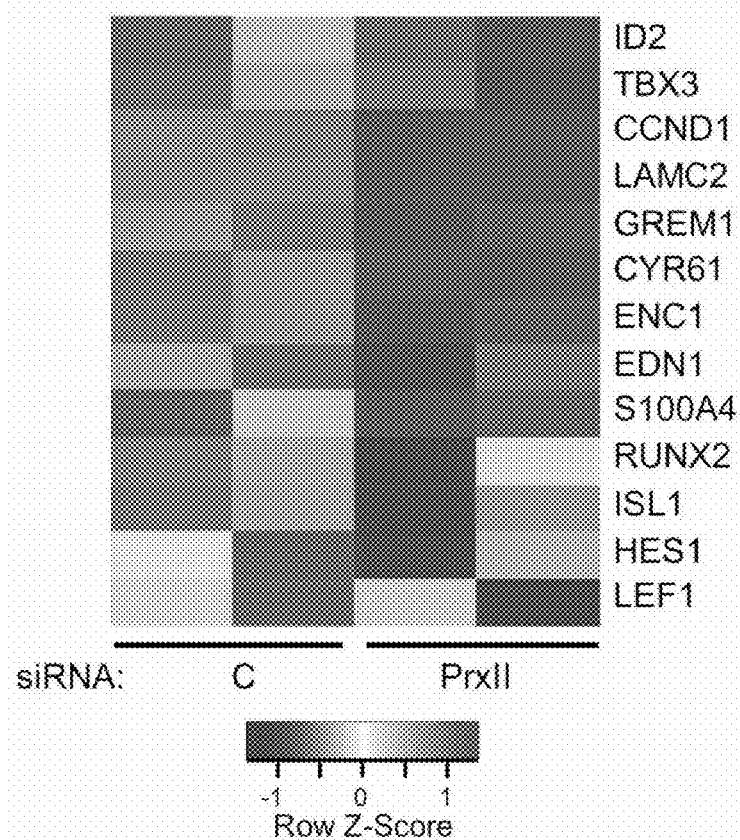

In addition to HT29 cells, PrxII deficiency downregulated 13 β-catenin target genes in SW480 cells (FDR<0.05), and in FIG. 32, it indicated that four genes (i.e., CCND1, S100A4, ID2, and EDN1) overlap with one other.

The downregulation of several different genes in SW480 cells indicates that it may mediated by the secondary effect of decrease in the β-catenin-related transcription complex or β-catenin.

These results indicate that PrxII deficiency promotes the degradation of transcription-active β-catenin through the destruction complex of CRC cells.

<Example 9> Wnt-Independent and Axin1-Dependent Destruction of β-Catenin by PrxII Deficiency in CRC Cells Axin1, another scaffold protein in APC mutations, is known to play an important role in β-catenin destruction. The overexpression of Axin1 in APC-mutant CRC cells is known to sufficiently induce the degradation of β-catenin.

Previously in FIG. 9, it confirmed that the expression of Axin1 was increased in the intestinal polyps of mice in which the PrxII gene was removed.

Figure 33:
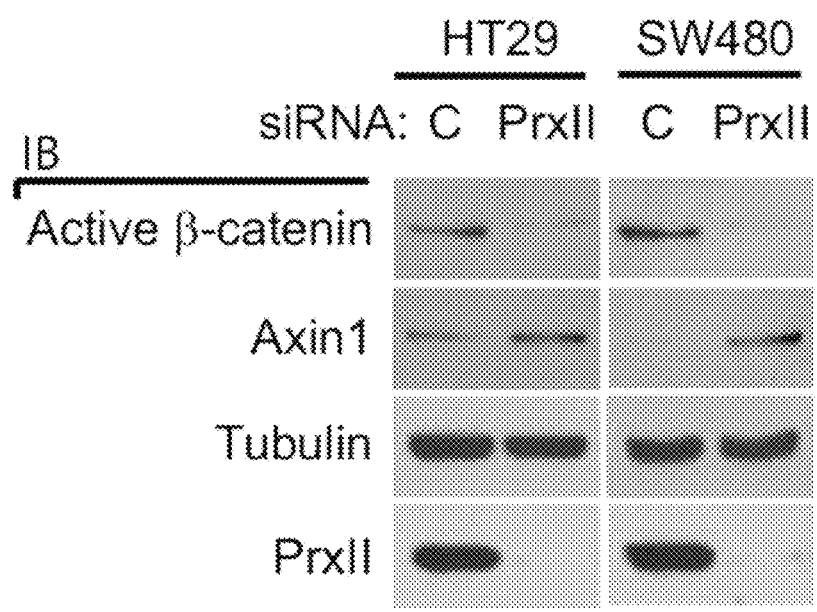
FIG. 33 shows an image illustrating the results of transfection of HT29 and SW480 cells with a control or PrxII-1 siRNA followed by measurement by immunoblotting against active β-catenin and Axin1, according to an embodiment of the present invention.

The amount of Axin and the Axin1-related destruction complex were measured in CRC cells. As a result of the immunoblot analysis in FIG. 33, it confirmed that PrxII deficiency increased the expression of endogenous Axin1 protein in both HT29 and SW480 CRC cells, which indicates that PrxII deficiency is inversely correlated with the expression of active β-catenin.

Figure 34:
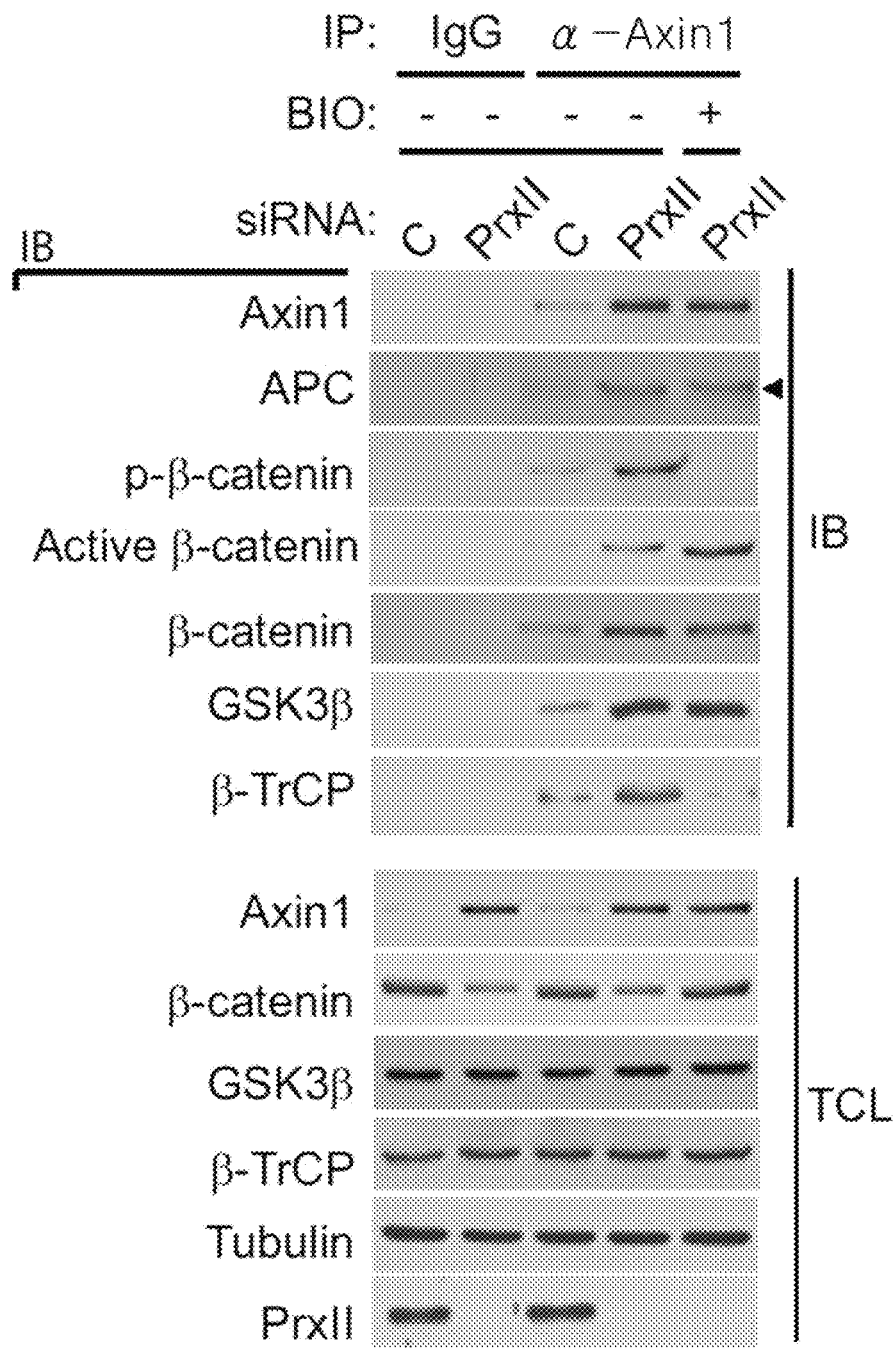
FIG. 34 shows an image confirming that PrxII deficiency significantly increases complexes, in which SW480 cells according to an embodiment of the present invention were transfected with a control or PrxII-1 siRNA and immunoblotting was performed for all complex-binding proteins separated by immunoprecipitation (IP) of Axin-1.

From the co-immunoprecipitation experiment in FIG. 34, it indicated that the PrxII deficiency increased the expression of the Axin1-related destruction complex. The phospho-β-catenin disappeared from the complex upon treatment with BIO, which is a GSK3β inhibitor.

Figure 35:
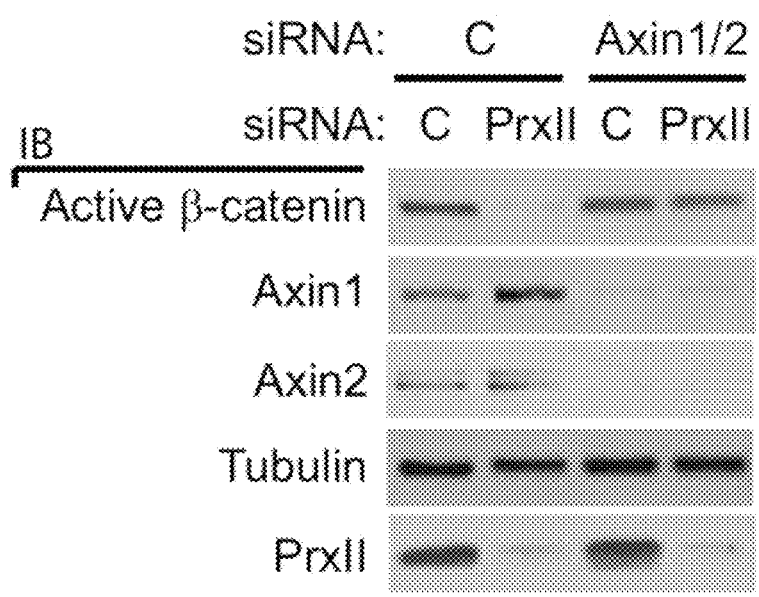
FIG. 35 shows an image illustrating the results of transfection of HT29 cells with a control or Axin-1/Axin-2 siRNAs, followed by immunoblotting against active i-catenin and Axin1, according to an embodiment of the present invention.

In addition, in FIG. 35, the knockdown of Axin1/2 restored the active β-catenin levels of PrxII-deficient cells to the levels of cells in the control.

These results indicate that Axin forms a functional destruction complex and regulates β-catenin degradation in PrxII-deficient CRC cells.

Since Axin is degraded by poly(ADP-ribose) polymerization (PARsylation) and subsequent ubiquitination, the state of Axin1 in HT29 and SW480 cells was analyzed.

In fact, it confirmed that the treatment with MG132 (i.e., a proteasome inhibitor) induces the accumulation of PARsylated and ubiquitinated Axin1 in the cells of the control and thus, Axin1 continues to degrade.

Figure 36:
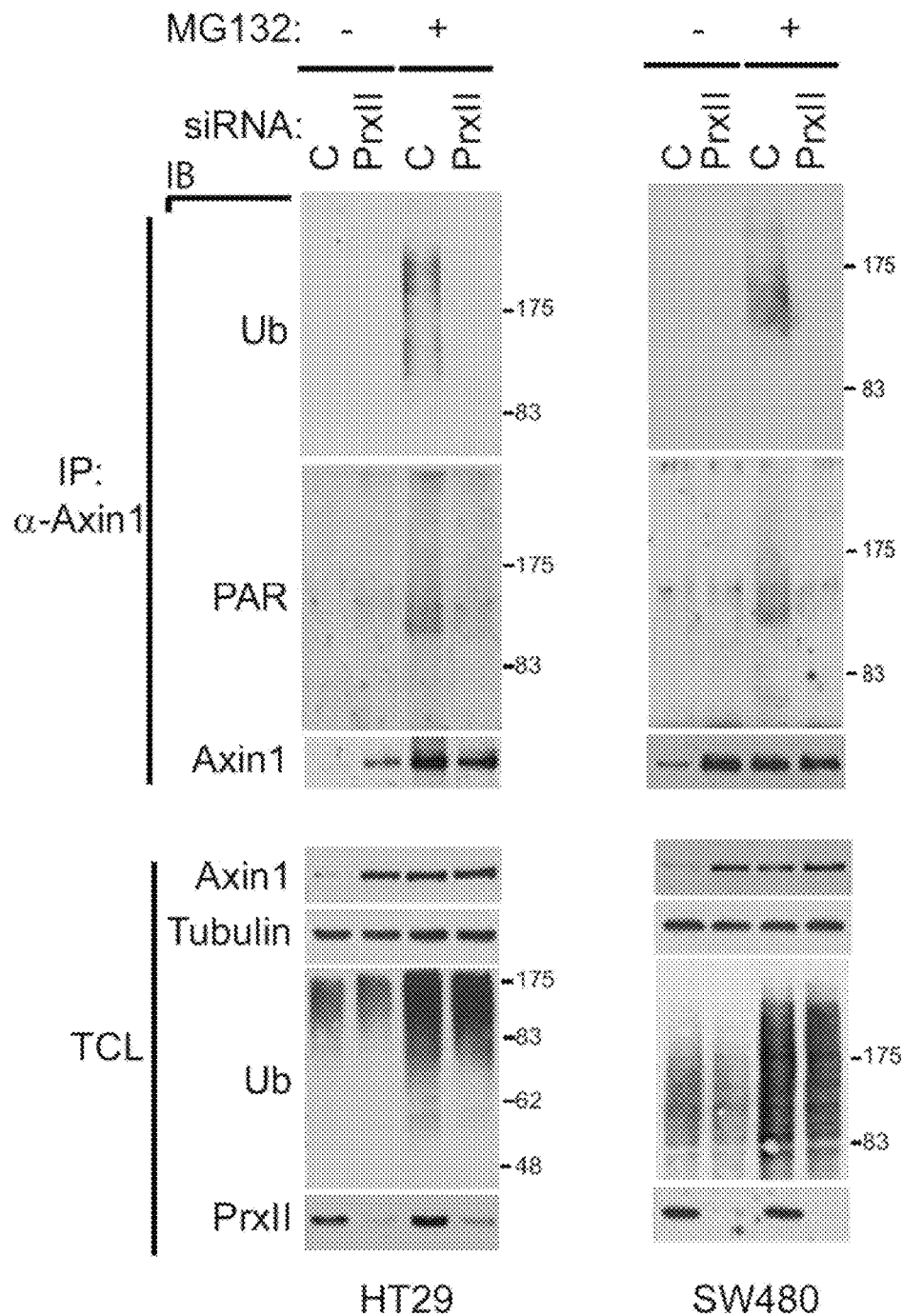
FIG. 36 shows images illustrating the results of transfection of HT29 and SW480 cells with a control or PrxII-1 siRNA, and immunoprecipitation of Axin-1, followed by immunoblotting performed on ubiquitination and poly-ADP-ribosylation, according to an embodiment of the present invention.

In contrast, as shown in FIG. 36, PrxII deficiency inhibited the PARsylation/ubiquitination of Axin1 without affecting total intracellular ubiquitination.

<Example 10> Determination of Colony Forming Ability of PrxII-Deficient CRC

To evaluate the biological significance of the PrxII-dependent regulatory mechanism of the Axin1/β-catenin pathway, colony forming ability in CRC cells was examined.

Figure 37:
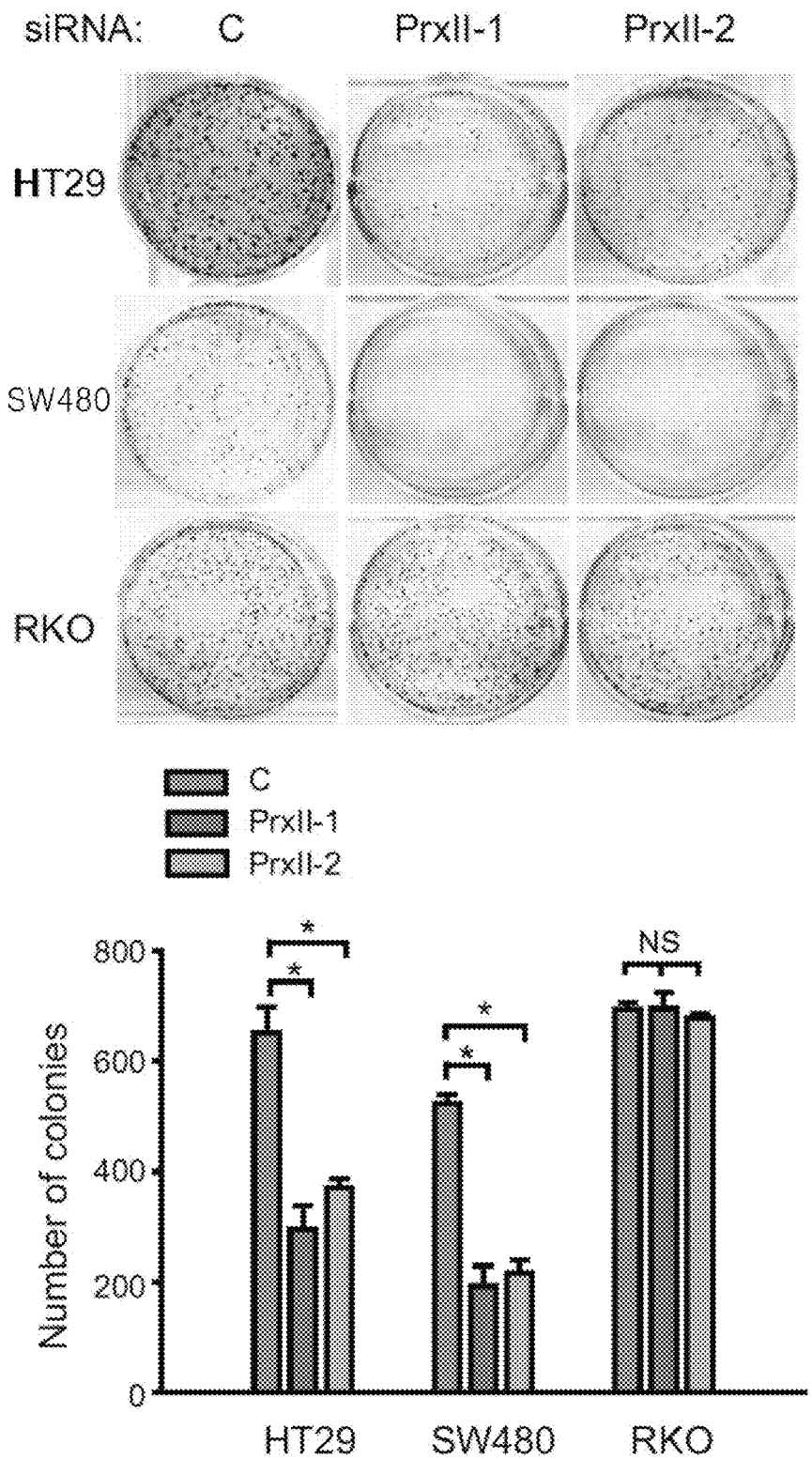
FIG. 37 shows an image and a graph illustrating the results of a colony forming assay, which was performed after transfecting RKO (i.e., an APC wild-type colorectal cancer (CRC) line) and HT29 and SW480 cells (i.e., APC-mutant cell lines) with a control or PrxII-1 siRNA, according to an embodiment of the present invention.

As a result of the in vitro colony forming ability assay, in FIG. 37, it confirmed that PrxII deficiency sufficiently inhibits colony formation in HT29 and SW480 cells, not RKO cells that express APC WT.

Figure 38:
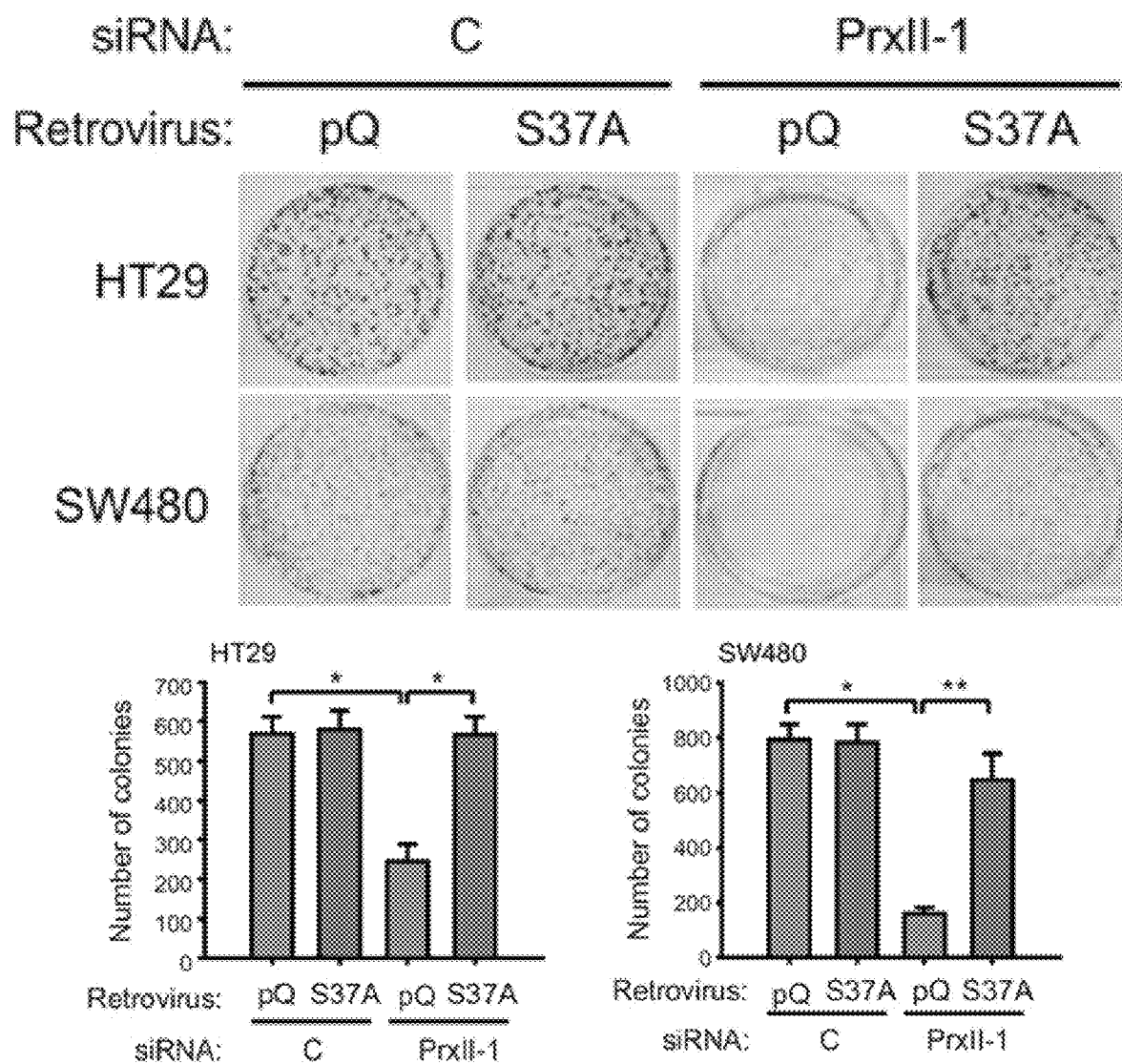
FIG. 38 shows an image and graphs illustrating the results of a colony forming assay, which was performed after transfecting HT29 and SW480 cells (i.e., APC-mutant cell lines) with a control or PrxII-1 siRNA, followed by expression of activated β-catenin (S37A), according to an embodiment of the present invention.

In FIG. 38, it confirmed that the expression of the active β-catenin S37A mutant almost completely restores the colony forming ability of APC-mutant CRC cells damaged by PrxII deficiency.

From these results, it indicated that PrxII deficiency can sufficiently reverse the carcinogenic phenotype of APC mutants via induction of β-catenin degradation by Axin1.

<Example 11> Analysis of Regulation of TNKS-Axin1 Signaling System by PrxII Deficiency TNKS is the only enzyme for poly(ADP-ribose) polymerization (PARsylation) of Axin proteins. Whether PrxII is essential for TNKS activity was confirmed by performing in vitro PARP analysis.

Figure 39:
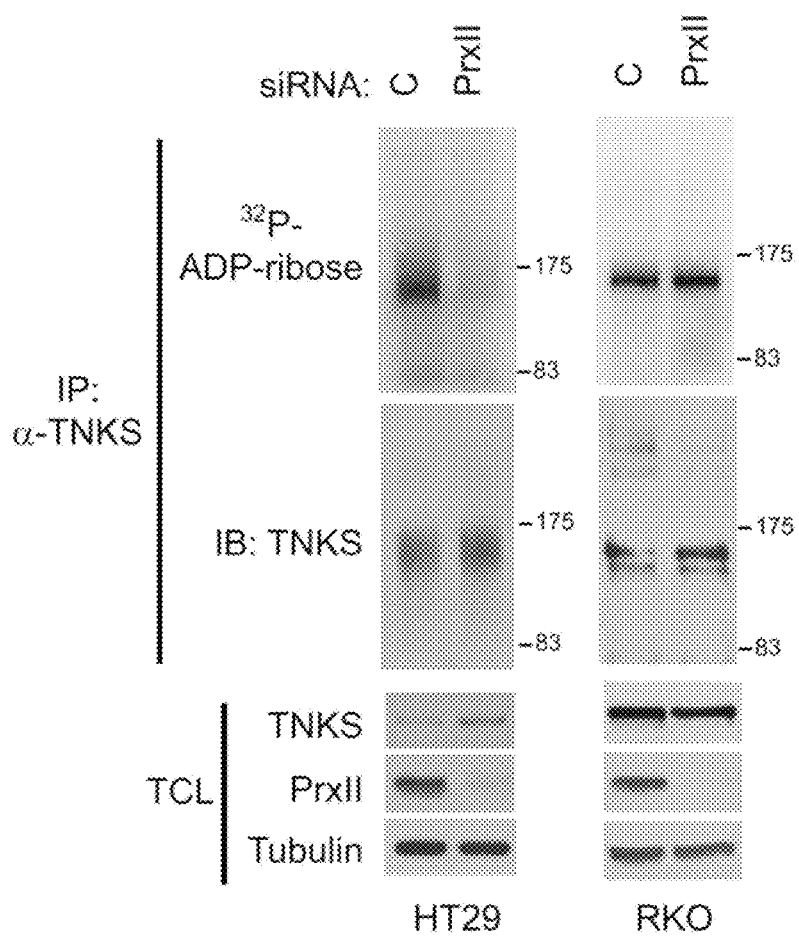
FIGS. 39 and 40 each show images illustrating the results, in which HT29 and RKO cells were transfected with a control or PrxII-1 siRNA, or treated with $H_2O_2$, and TNKS1 was immunoprecipitated, and the activity of ADP-ribose polymerase (PARP) was measured, according to an embodiment of the present invention.
Figure 40:
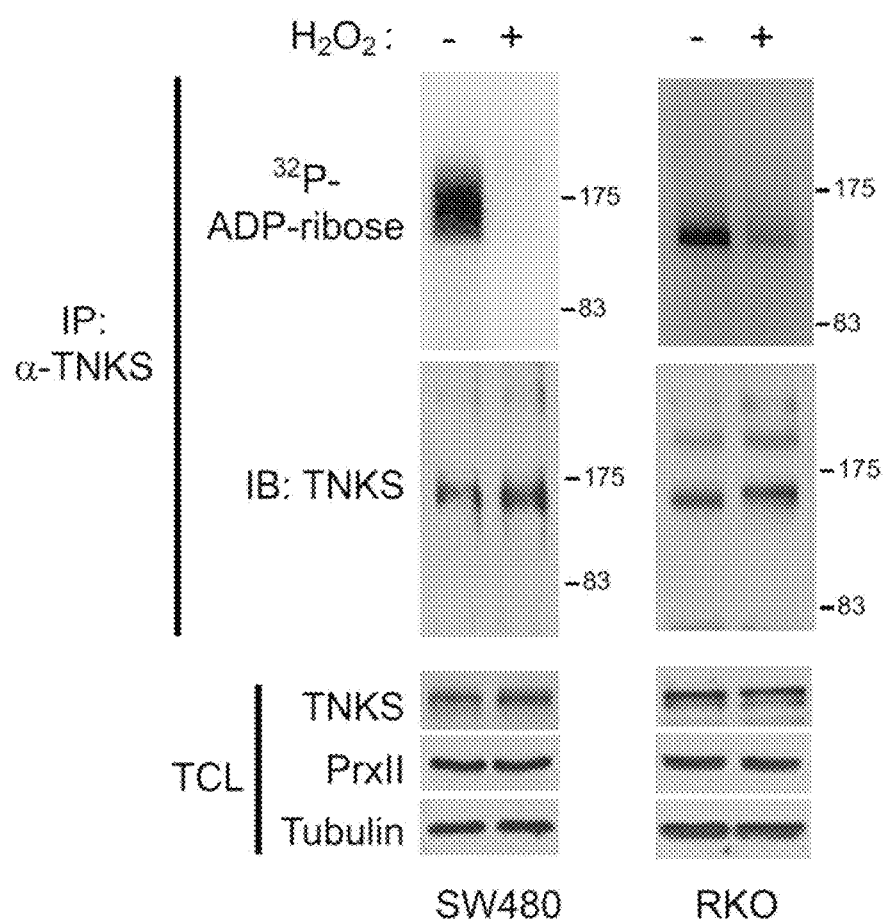

As shown in FIG. 39, PrxII deficiency induced a severe impairment of TNKS activity in APC-mutants (i.e., HT29 and SW480 cells), but not in RKO cells in which the AKO-function is retained. As shown in FIG. 40, on the contrary, hydrogen peroxide treatment inhibited TNKS activity in both HT29 and SW480 cells.

From these results, it may indicated that exogenous hydrogen peroxide directly inactivates TNKS activity regardless of APC mutation.

Since TNKS is known to be subjected to auto-polyADP-ribosylation (auto PARsylation) and degradation, the expression level of TNKS was measured in the CRC cell panel along with the substrate proteins.

Figure 41:
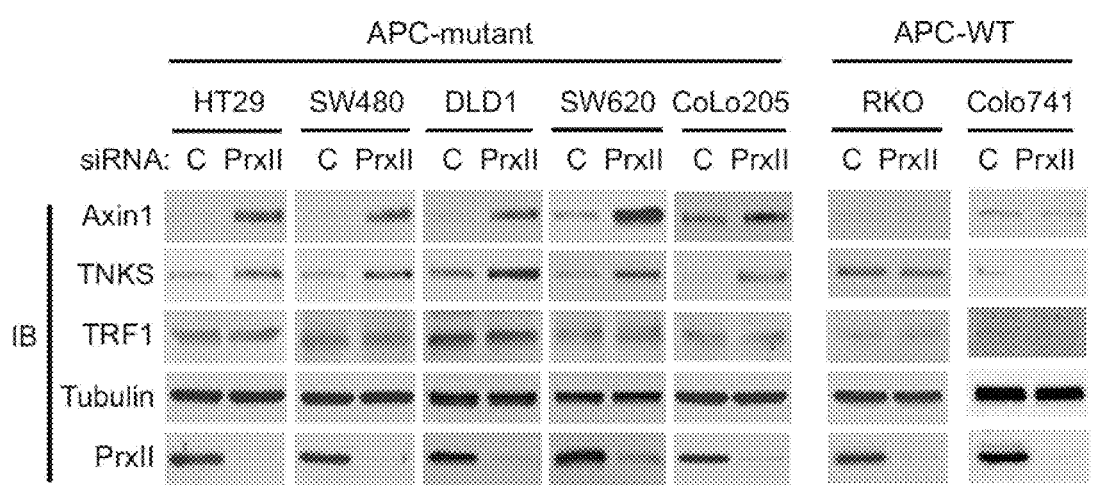
FIG. 41 shows images illustrating the results, in which various APC wild-type and APC-mutant colorectal cancer cell (CRC) lines were transfected with a control or PrxII-1 siRNA, and the expression levels of TNKS1, and Axin1 and TRF1 (i.e., the substrates of TNKS1) were measured by immunoblotting, according to an embodiment of the present invention.

As shown in FIG. 41, PrxII deficiency increased the expression levels of TNKS and Axin1 in all APC-mutant CRC cells tested, but not in cells including RKO and Colo741 cells where APC-function was retained.

More importantly, the PrxII deficiency did not affect the expression level of telomeric repeat-binding factor 1 (TRF1), which is another TNKS substrate essential for telomerase regulation in the nucleus.

Figure 42:
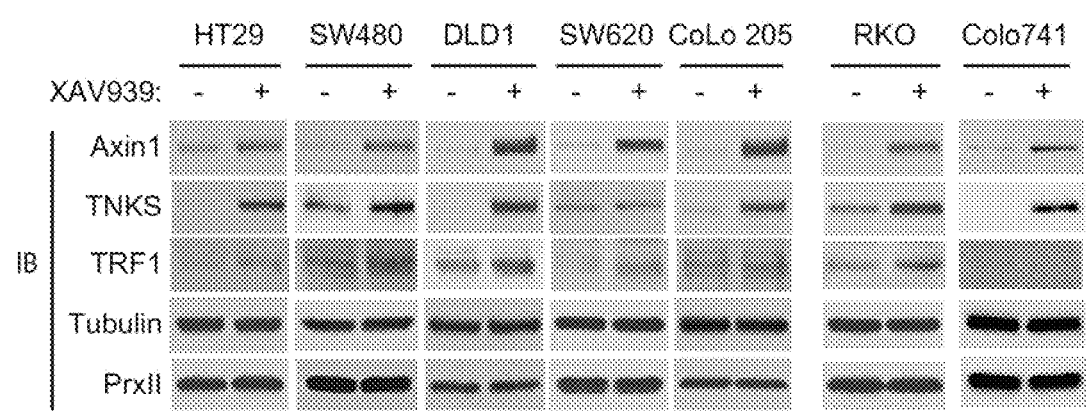
FIG. 42 shows images illustrating the results, in which various APC wild-type and APC-mutant colorectal cancer cell (CRC) lines were pretreated with a TNKS1 inhibitor (XAV939) for one hour, and the expression levels of TNKS1, and Axin1 and TRF1 (i.e., the substrates of TNKS1) were measured by immunoblotting, according to an embodiment of the present invention.
Figure 43:
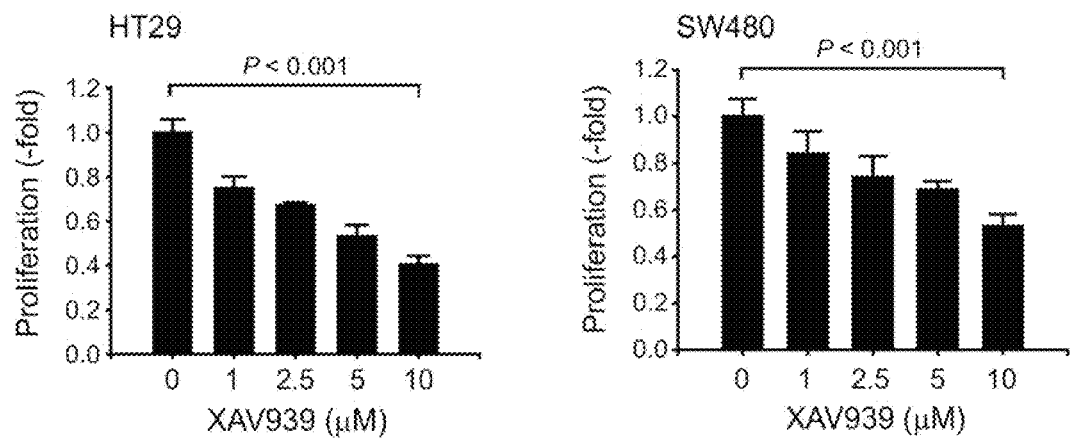
FIG. 43 shows graphs illustrating the results, in which various APC-mutant colorectal cancer cell (CRC) lines were pretreated with a TNKS1 inhibitor (XAV939) for one hour, and the proliferation levels of the cells were measured, according to an embodiment of the present invention.

In FIGS. 42 and 43, on the contrary, direct inhibition of TNKS using a specific inhibitor, XAV939, increased the expression levels of TNKS and the substrates (i.e., Axin1 and TRF1) in all CRC cells, resulting in inhibition of proliferation of HT29 and SW480 cells.

APC knockdown was performed in RKO cells to confirm a direct correlation between APC and PrxII function in CRC cells.

Figure 44:
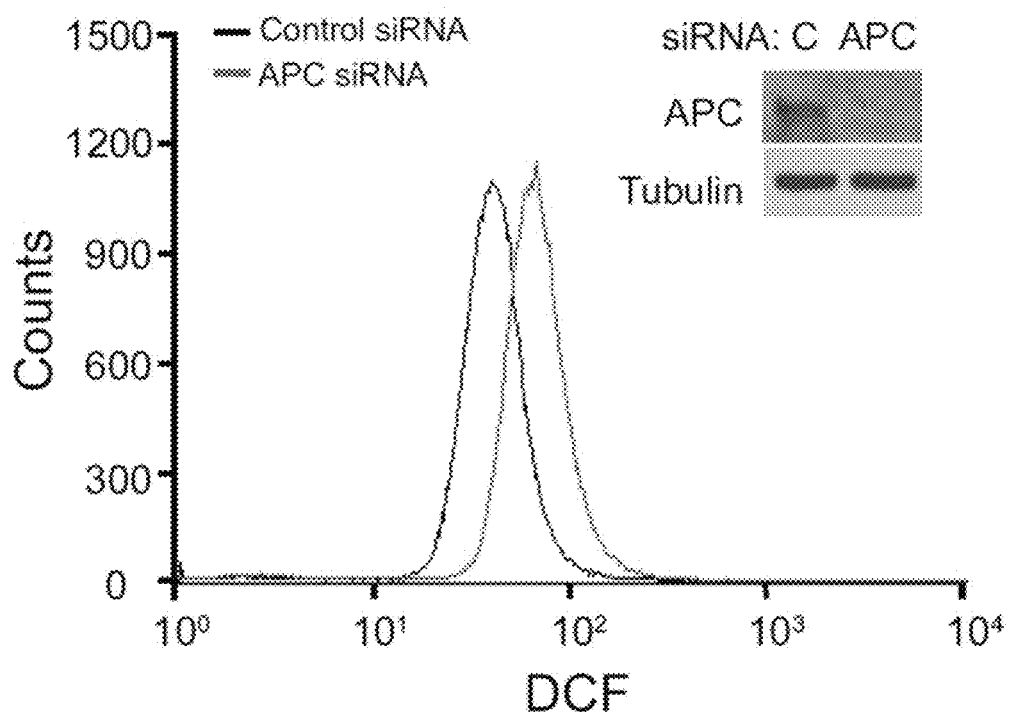
FIG. 44 shows a graph illustrating the results of the intracellular $H_2O_2$ levels in APC gene deficient RKO colorectal cancer (CRC) cell lines, according to an embodiment of the present invention.
Figure 45:
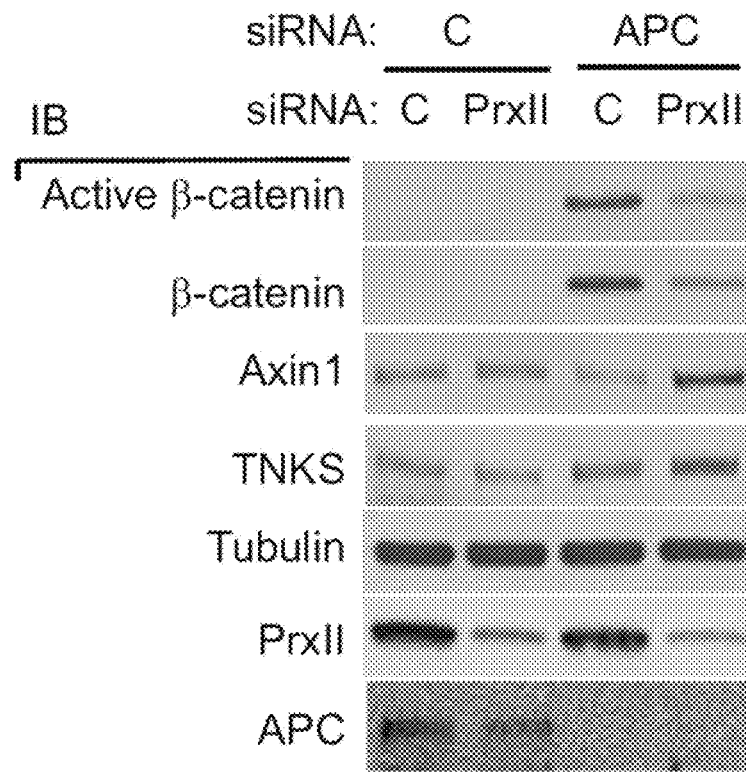
FIG. 45 shows an image illustrating the results, in which the levels of β-catenin, Axin1, and TNKS1 were measured by immunoblotting in APC gene deficient RKO cells, according to an embodiment of the present invention.
Figure 46:
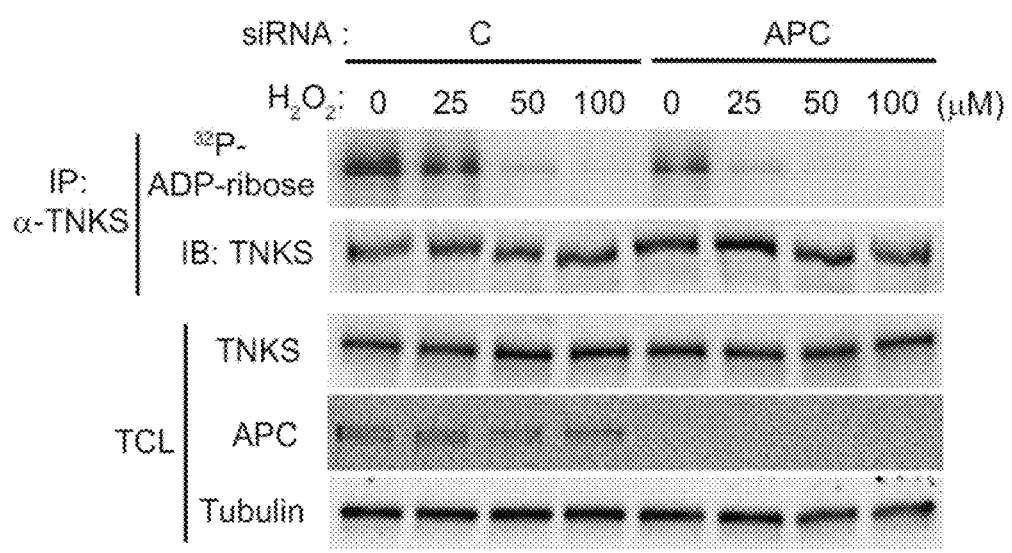
FIG. 46 shows images illustrating the results of ADP-ribose polymerase activity of TNKS1 in APC gene deficient RKO cells, according to an embodiment of the present invention.

As shown in FIGS. 44, 45, and 46, the APC knockdown certainly induced a significant increase in the expression levels of $H_2O_2$ and β-catenin in cells, and consequently accelerated $H_2O_2$-dependent inactivation of TNKS1. In addition, simultaneous deficiency of APC and PrxII increased the expression levels of TNKS and Axin1 proteins along with a decrease in the expression level of β-catenin.

Since PrxII is a peroxidase in the cytoplasm, it is suggested that PrxII can selectively protect TNKS in the cytoplasm from oxidative stress induced by APC mutation or loss.

<Example 12> Confirmation of Mechanism of Inactivation of PARP Activity of $H_2O_2$-Mediated TNKS To confirm the mechanism of inactivation of PARP activity of $H_2O_2$-mediated TNKS, the oxidation-sensitive Cys residues within the PARP catalytic domain of TNKS were examined.

Five Cys residues including three Zn-binding motifs were found by aligning the peptide sequences of various PARP domains, and these Cys residues were found to be uniquely present in the TNKS isomers between PARP family.

Figure 47:
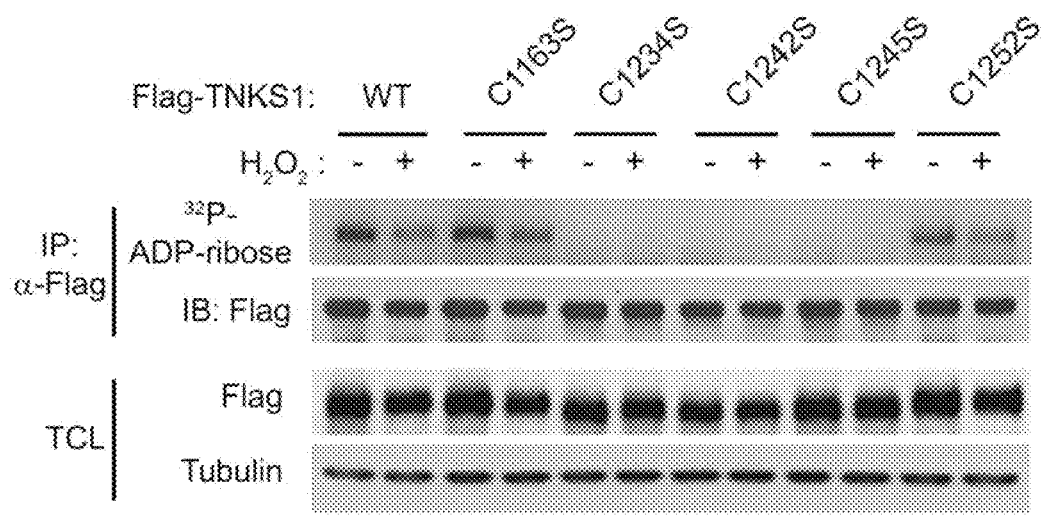
FIG. 47 shows images illustrating the results, in which the cells expressed various TNKS1 cysteine single mutant enzymes immunoprecipitated with an anti-TNKS antibody, and the ADP-ribose polymerase activity of TNKS1 was measured, according to an embodiment of the present invention.

In TNKS1, each Cys residue was mutated to Ser and its PARP activity was examined. As a result, the mutations of three Zn-coordinating Cys residues (C1234, C1242, and C1245) among the five Cys residues found resulted in a complete loss of PARP activity, as shown in FIG. 47.

Figure 48:
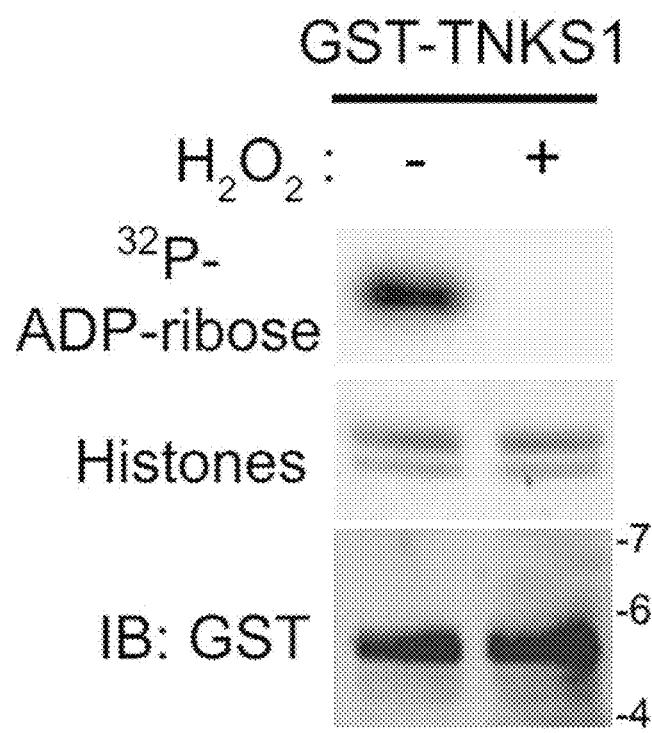
FIG. 48 shows an image illustrating the results of expression and purification of recombinant proteins in *E. coli* cells for the PARP domain of TNKS1 according to an embodiment of the present invention.

To test whether zinc binding motifs are unstable under oxidizing conditions, a recombinant TNKS1 PARP domain (amino acids of 1023-1327) was prepared. The TNKS1 PARP domain showed intact polyADP-ribosylation activity and was fully inactivated by incubation with $H_2O_2$, as shown in FIG. 48.

Zinc binding proteins release zinc ions by cysteine oxidation, and the released free zinc ions can be measured by a spectrophotometer using 4-(2-pyridylazo) resorcinol.

Figure 49:
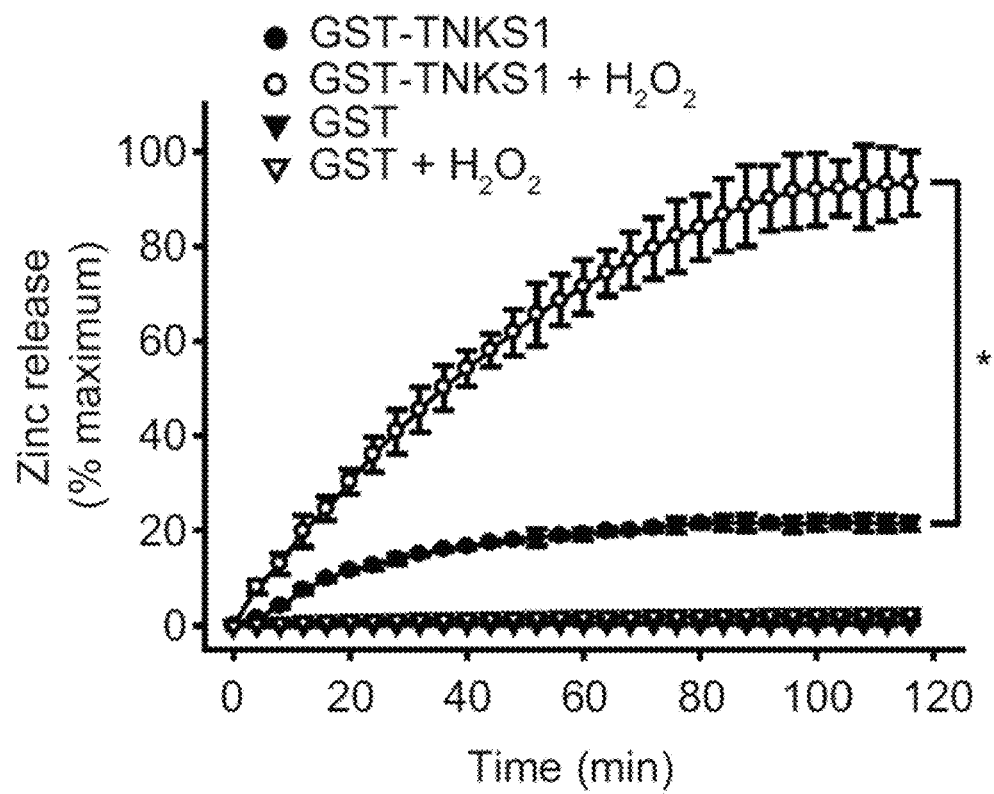
FIG. 49 shows a graph illustrating the results of the releasing of Zinc ions by hydrogen peroxide treatment in the purified recombinant TNKS1-PARD protein according to an embodiment of the present invention.

The results measured by a spectrophotometer by the above method are shown in FIG. 49. In FIG. 49, it indicated that $H_2O_2$ treatment induces a nearly complete release of zinc ions such that 90% or more of TNKS1 PARP proteins ultimately lost zinc ions.

From these results, it confirmed that zinc binding motifs of TNKS are essential for PARP activity and that the oxidation of Cys residues mediated by $H_2O_2$ can induce the release of zinc ions from the PARP domain.

From these results, it indicated that the redox of TANKS is regulated by PrxII-regulated $H_2O_2$.

<Example 13> Examination of Selective Binding Between PrxII and TNKS

The interaction between PrxII and TNKS was examined to demonstrate how PrxII protects TNKS from the $H_2O_2$-mediated inactivation.

Figure 50:
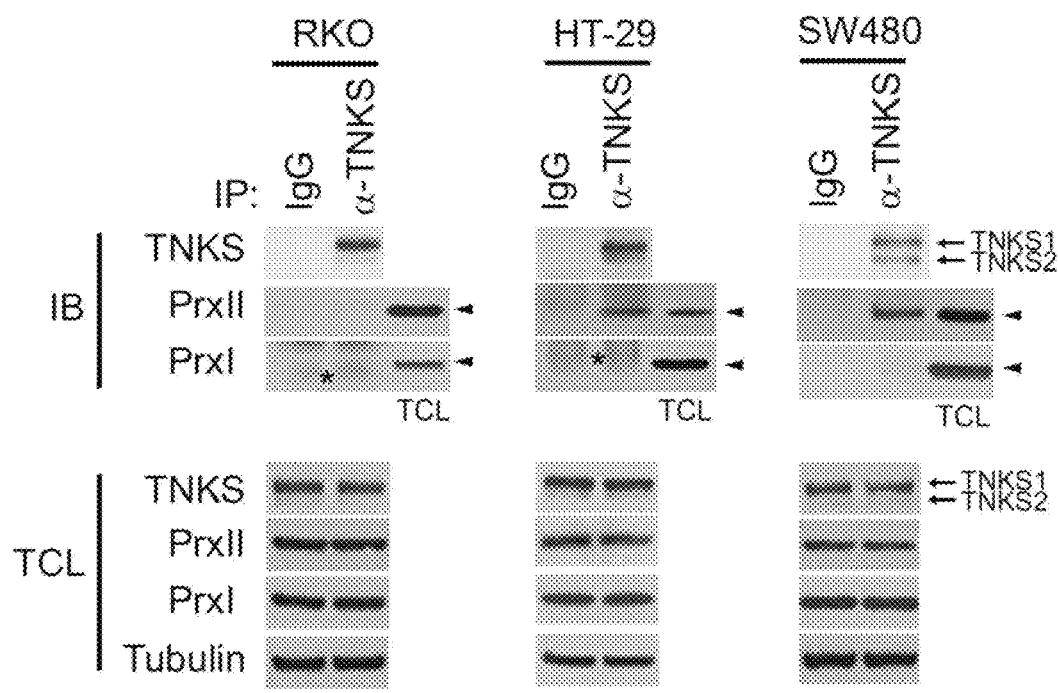
FIG. 50 shows images illustrating the results of immunoblotting of the cells against the proteins indicated after the immunoprecipitation reaction with an anti-TNKS antibody, according to an embodiment of the present invention.

In FIG. 50 which shows the experimental results of co-immunoprecipitation (co-IP), it confirmed that endogenous TNKS interacts with PrxII only in APC-mutant HT29 and SW480 cells, but not in RKO cells where APC functions are retained.

In contrast. TNKS did not interact with PrxI in APC-mutant HT29 and SW480 cells, confirming the specific role of PrxII in the TNKS/Axin1/β-catenin pathway.

Figure 51:
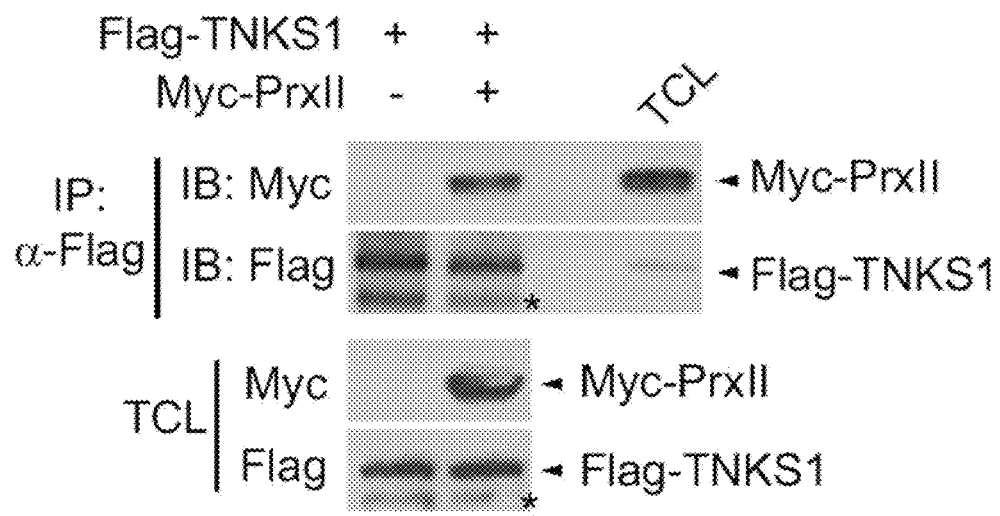
FIG. 51 shows images illustrating the results of Co-immunoprecipitation (co-IP) for detecting a binding between TNKS and PrxII proteins, according to an embodiment of the present invention.

To characterize the direct interaction between TNKS1 and PrxII, two proteins were overexpressed in human embryonic kidney cells, HEK293, as non-CRC cells. As a result, as shown in FIG. 51, it confirmed that TNKS and PrxII directly interact in the co-IP experiment.

Figure 52:
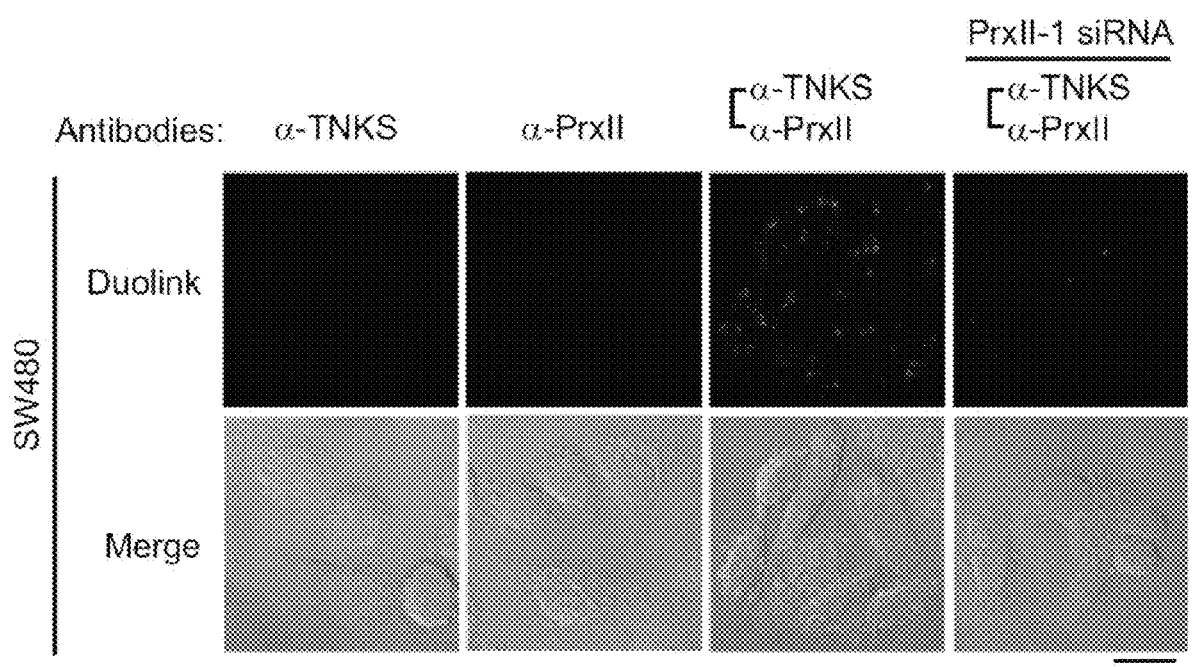
FIGS. 52 and 53 each show images illustrating the results of in situ proximity ligation assays according to an embodiment of the present invention.
Figure 53:
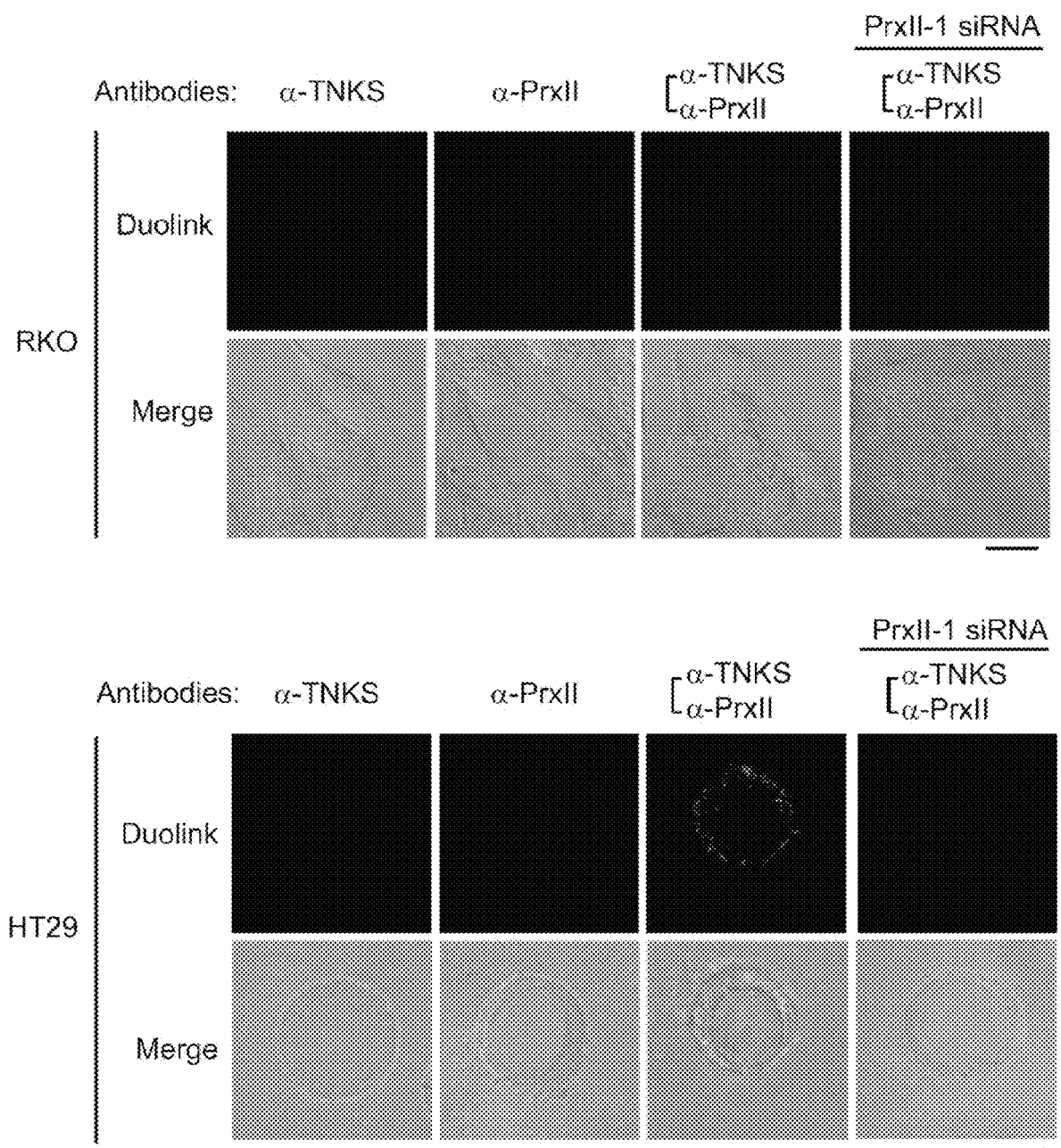

More specifically, in FIGS. 52 and 53, the in situ proximity ligation assay (in situ PLA) visualized that the direct interaction between TNKS and PrxII occurs in the cytoplasm of HT29 and SW480 cells, not in RKO cells. In FIGS. 52 and 53, the red fluorescence signals indicating the interaction of the two proteins disappeared almost completely by PrxII deficiency.

Therefore, it indicated that the blocking of redox in TNKS by PrxII is highly specific of a protein-protein interaction and is dependent on APC mutations.

Figure 54:
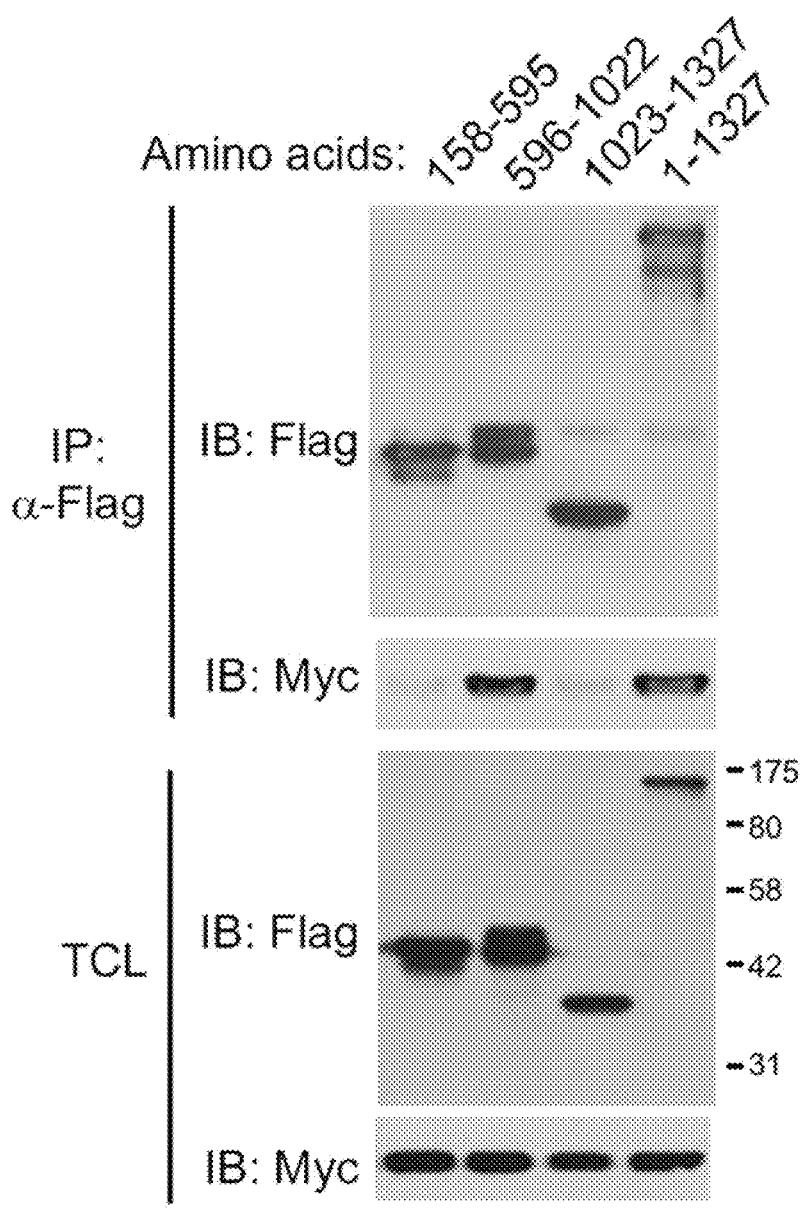
FIGS. 54 and 55 each show images illustrating the results of mutual binding assays using a truncation mutation or a single point mutation of TNKS and Myc-PrxII, respectively, according to an embodiment of the present invention.

TNKS and PrxII mutagenesis were performed to analyze molecular interaction maps. In FIG. 54, IP experiments showed that when a truncated TNKS mutant is expressed along with PrxII, PrxII interacts with the ankyrin repeat cluster (ARC) 4/5 domain of TNKS. This demonstrated that PrxII binding does not overlap with Axin1, which binds to the ARC 2/3 domain.

The TNKS ARC domain recognizes the consensus sequence, RXXPXG(SEQ ID NO: 10), in the client protein, and in particular, the Gly residue at position 6 plays a crucial role in direct binding.

Figure 55:
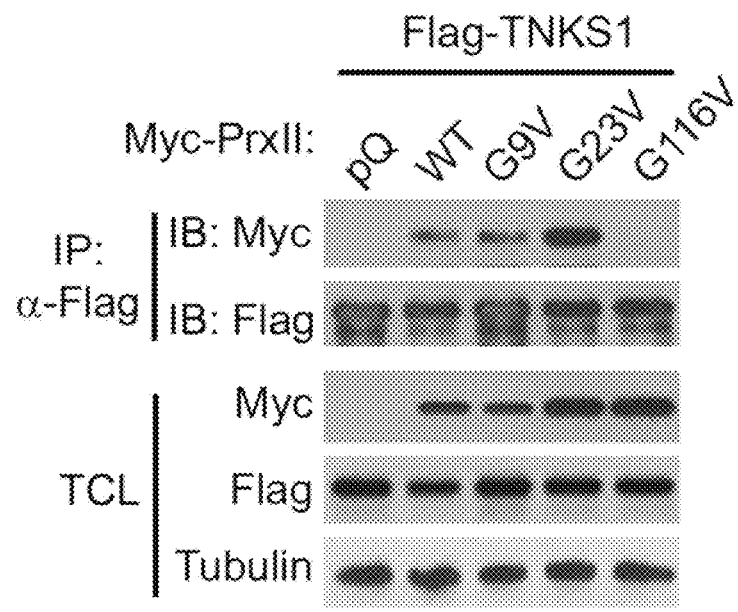

After searching similar hexapeptide sequences in PrxII, three potential common regions were found, and Gly-to-Val mutations were introduced thereto. In FIG. 55 in which the results of the Co-IP experiment are shown, it indicated that only the G116V mutation among the three mutation sites can completely remove the binding between PrxII and TNKS1.

Figure 56:
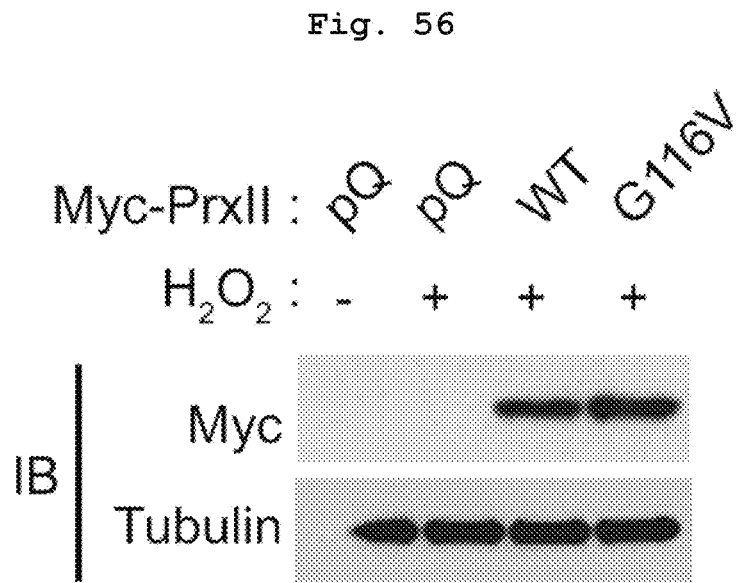
FIGS. 56 and 57 illustrate the results of intracellular expression and peroxidase activity of wild type and a G116V mutant of PrxII according to an embodiment of the present invention.
Figure 57:
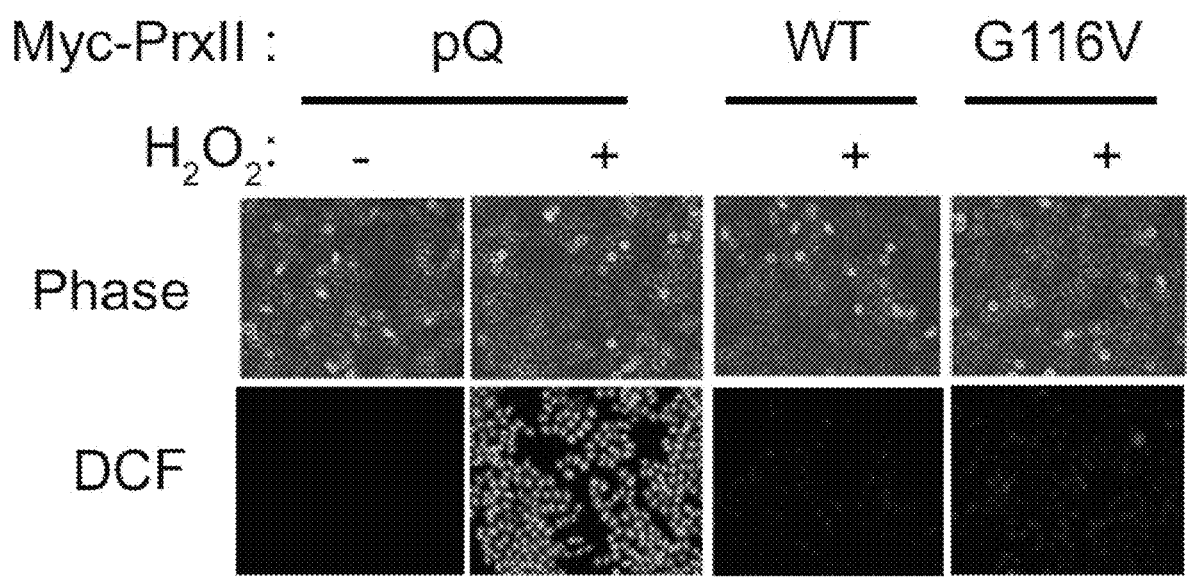

In FIGS. 56 and 57. PrxII WT and G116V mutants showed the same levels of expression and peroxidase activity, however, as shown in FIG. 53, the PrxII G116V mutant did not block the inhibition of TNKS activity by $H_2O_2$ but PrxII WT completely blocked the inhibition.

Figure 58:
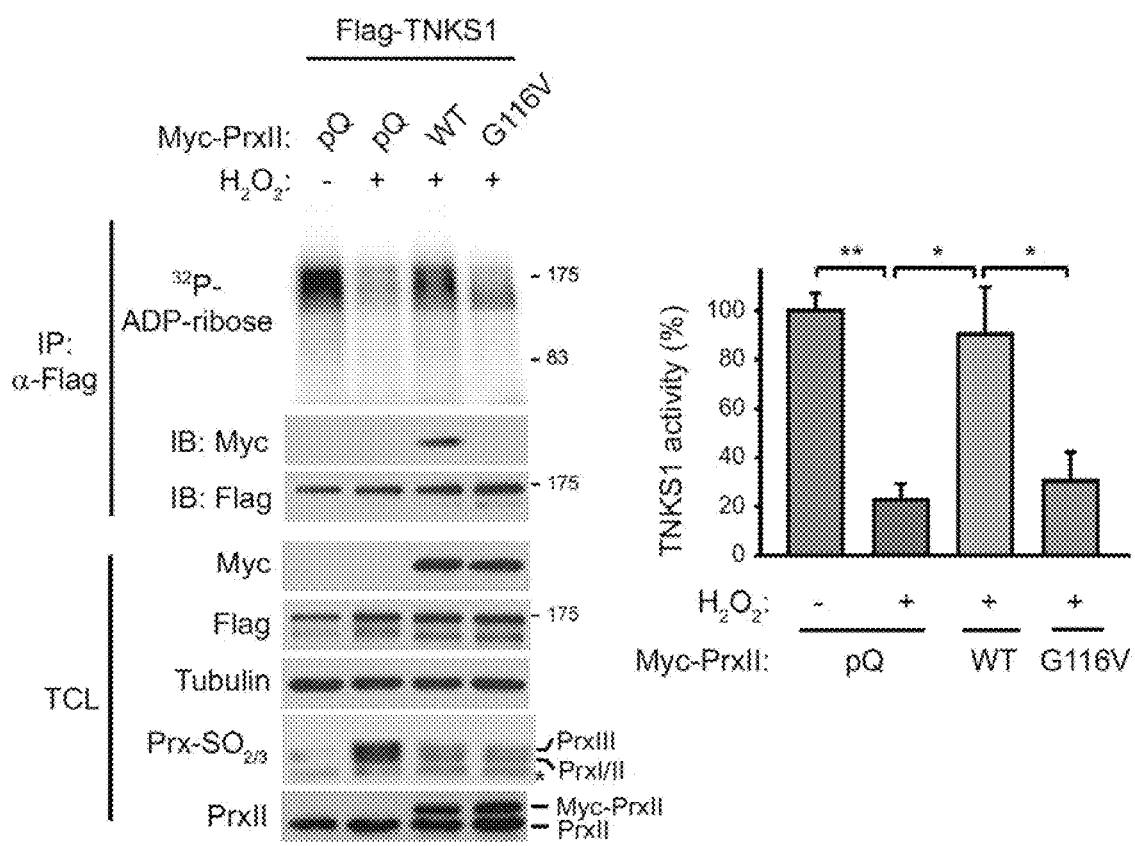
FIG. 58 shows images and a graph illustrating the results of PARP activity of TNKS1 in cells expressing wild type and a G116V mutant of PrxII according to an embodiment of the present invention.

In addition, in Lanes 2 and 3 of FIG. 58, it was indicated that the Prx-$SO_{2/3}$ blot completely peroxidated the endogenous 2-Cys Prx upon $H_2O_2$ treatment, whereas the exogenous PrxII with a C-terminal Myc tag (PrxII-Myc) was resistant to peroxidation.

In fact, as a result of the analysis of the activity of 2-Cys Prx ex vivo using a recombinant enzyme, as shown in FIG. 58, the PrxII-Myc enzyme showed a strong peroxidation enzyme activity without any sign of peroxidation, unlike the wild-type PrxII enzyme.

Since it is known that the C-terminal modification of the PrxII protein confers resistance to peroxidation, it predicted that the addition of the Myc tag to the C-terminus may result in a similar structural change in PrxII, which is converted to a peroxidation resistant form.

In addition, colony forming assays were performed to determine the biological significance of the PrxII-TANKS interaction.

Figure 59:
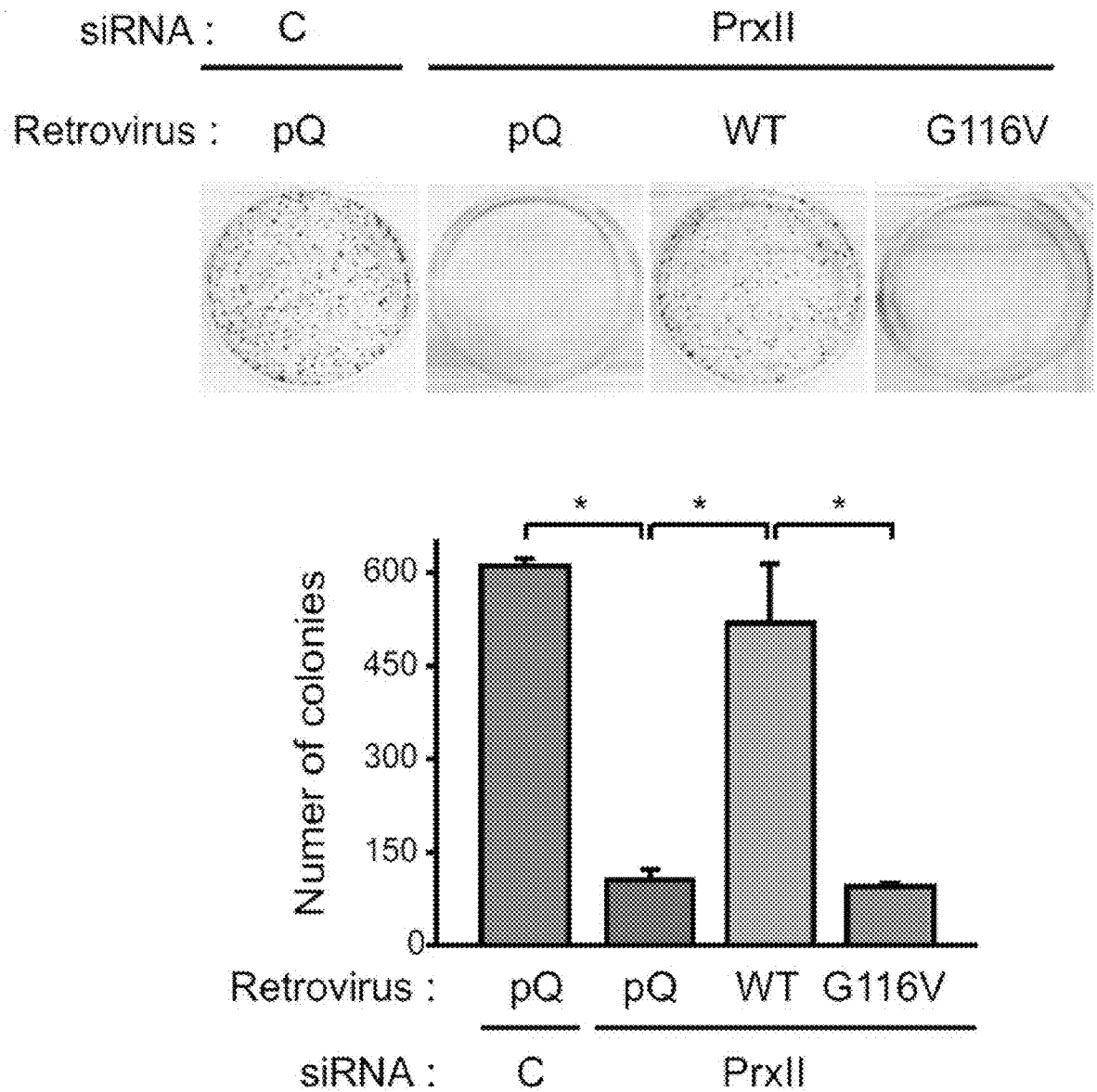
FIG. 59 shows an image and a graph illustrating the results of colony forming assays in cells expressing wild type and a GI 16V mutant of PrxII according to an embodiment of the present invention.

In FIG. 59, the colony formation of APC-mutant SW480 cells inhibited by PrxII deficiency was fully recovered by ectopic expression of PrxII WT, but the colony formation of the G116V mutant was not fully recovered.

From these results, it confirmed that the bound PrxII can prevent oxidative inactivation of tankyrase by removing $H_2O_2$ from tankyrase, which is important for the growth of APC-mutant CRC cells.

<Example 14> Analysis of PrxII Expression in Human CRC Tissues

Figure 60:
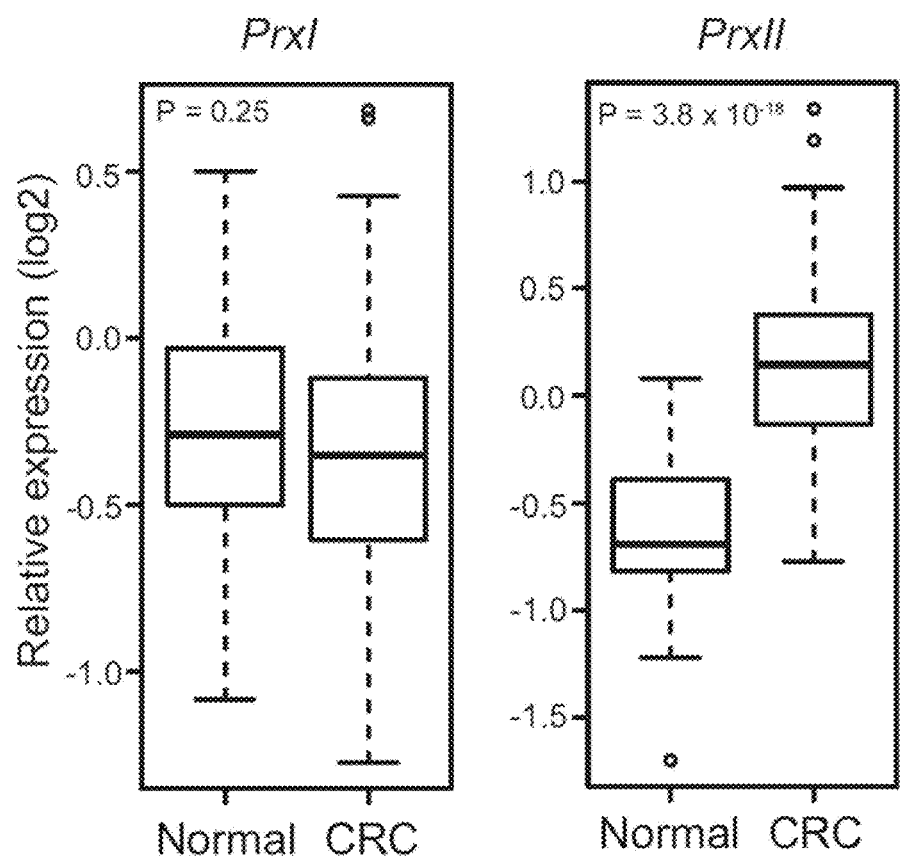
FIGS. 60 and 61 each show images illustrating the comparison results of expression levels of PrxI and PrxII genes in CRC patients (n=155) retrieved from healthy individuals and The Cancer Genome Atlas (TCGA) code database according to an embodiment of the present invention.
Figure 61:
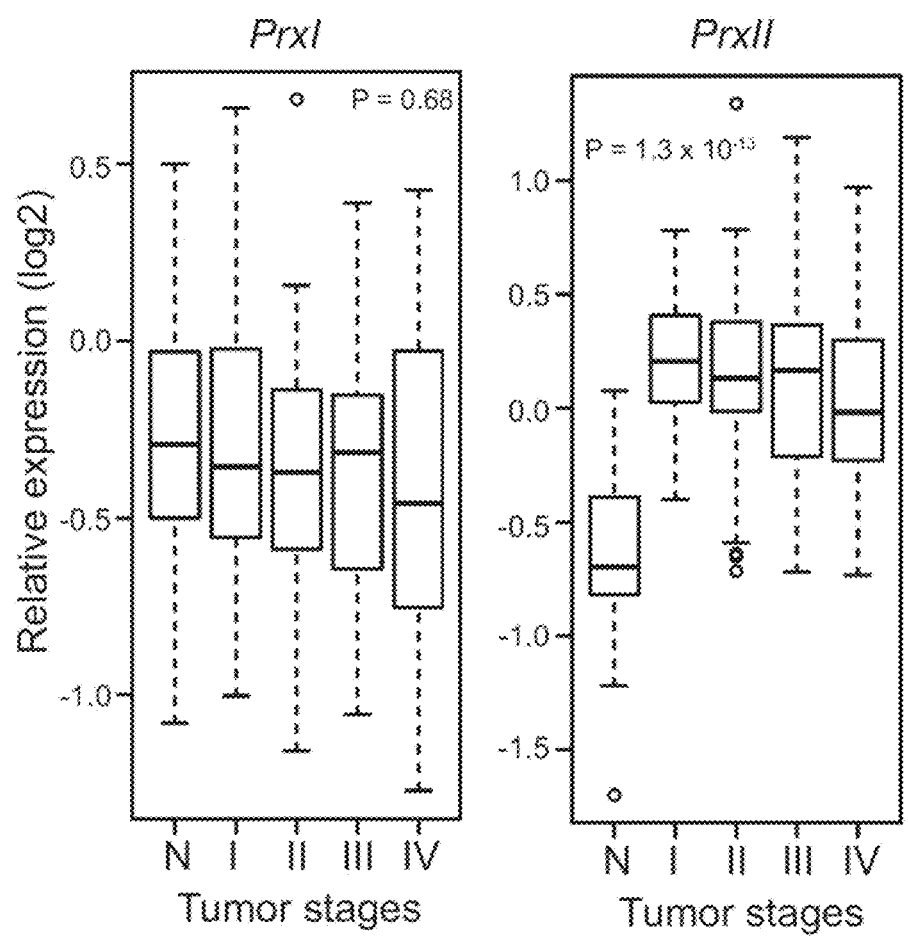

As shown in FIG. 60, as a result of the gene expression analysis of the Cancer Genome Atlas (TCGA) database1, it confirmed that PrxII expression was significantly higher than normal colorectal tissue in tumor specimens of colorectal adenocarcinoma patients and that the expression of PrxI (i.e., the closest homologous protein) showed no such difference. In FIG. 61, an increased PrxII expression was observed in all tumor steps.

Figure 62:
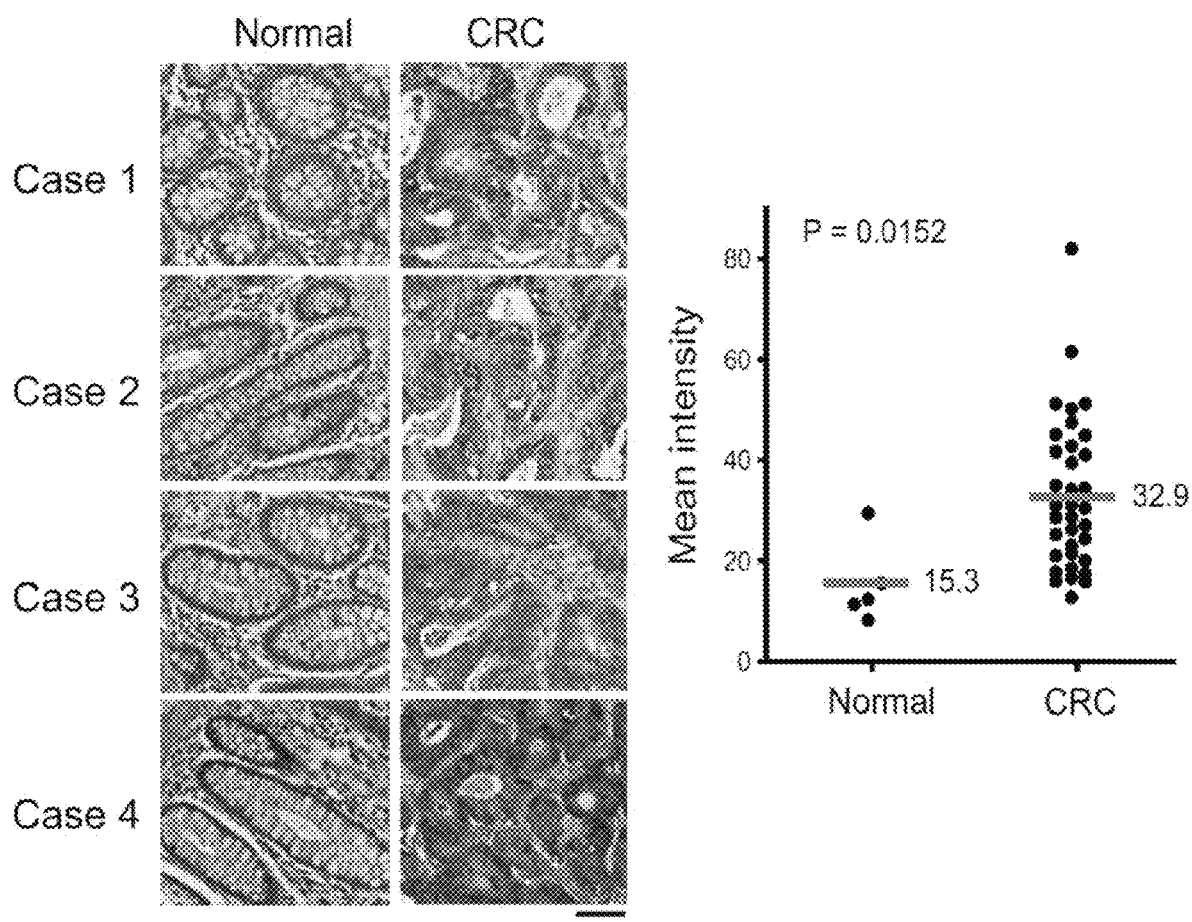
FIG. 62 shows images and a graph illustrating the results of PrxII immunostaining in colon tissue arrangement of healthy individuals and CRC patients according to an embodiment of the present invention.

As shown in FIG. 62, the immunohistochemistry performed using CRC tissue array showed PrxII levels approximately 2 times higher in CRC tissues compared to normal tissues. From these results, it confirmed that specific PrxII induction may be a prerequisite for CRC expansion.

<Example 15> Regulation of PrII Activity by Compound 6 (Conoidin A)

Based on this assay, a cell-permeable compound of Compound 6 called Conoidin A was tested to evaluate the possibility of treating human CRC by inhibiting PrxII.

Figure 63:
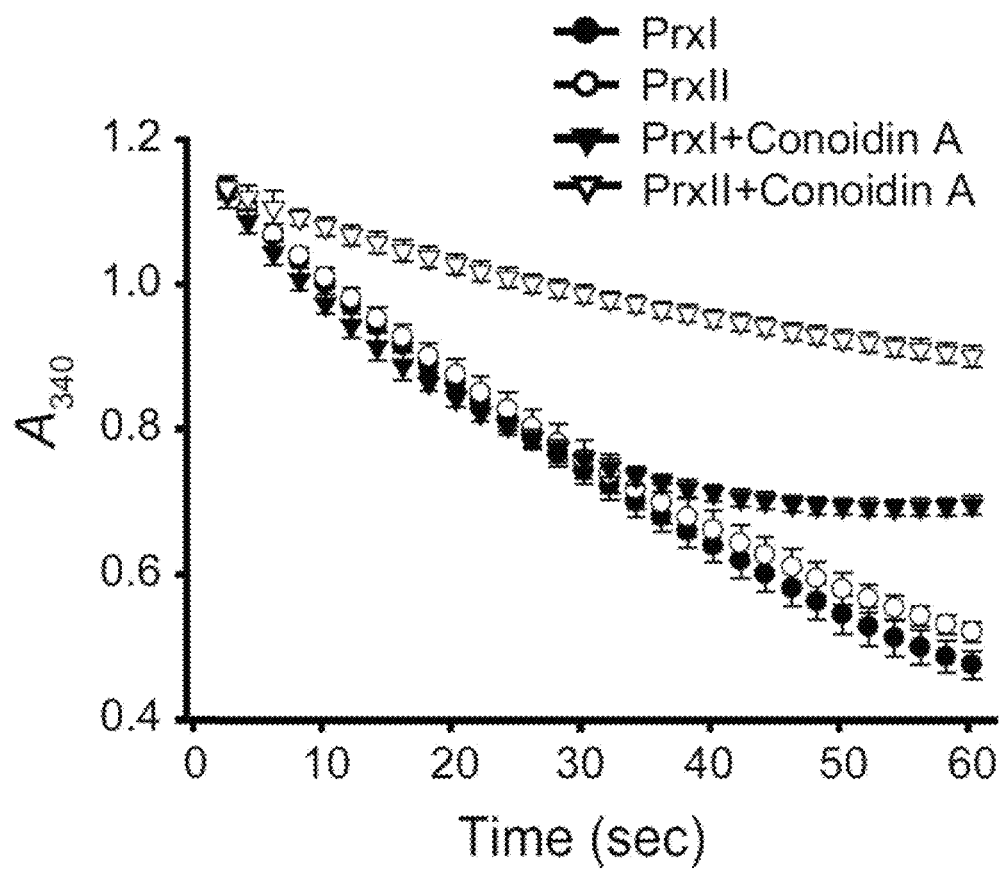
FIG. 63 shows a graph illustrating the results of inhibition of activity against PrxI and PrxII of Compound-6 (Conoidin A) according to an embodiment of the present invention.

In the in vitro Prx assay of FIG. 63, it was found that Compound 6 (Conoidin A) inhibited human PrxII activity by about 85% (214.9±24.3 nmol min$^{-1}$ for the control, 38.8±17.1 nmol min$^{-1}$ for the group treated with Conoidin A), and inhibited PrxI activity by about 50%.

In comparison, the initial rate of PrxI activity was not affected by Compound 6 (Conoidin A) (263.7±45.4 nmol min$^{-1}$ for the control, 241.7±21 nmol min$^{-1}$ for the group treated with Conoidin A).

<Example 16> Colony Forming Assay by Treatment with Compound 6 (Conoidin A)

Figure 64:
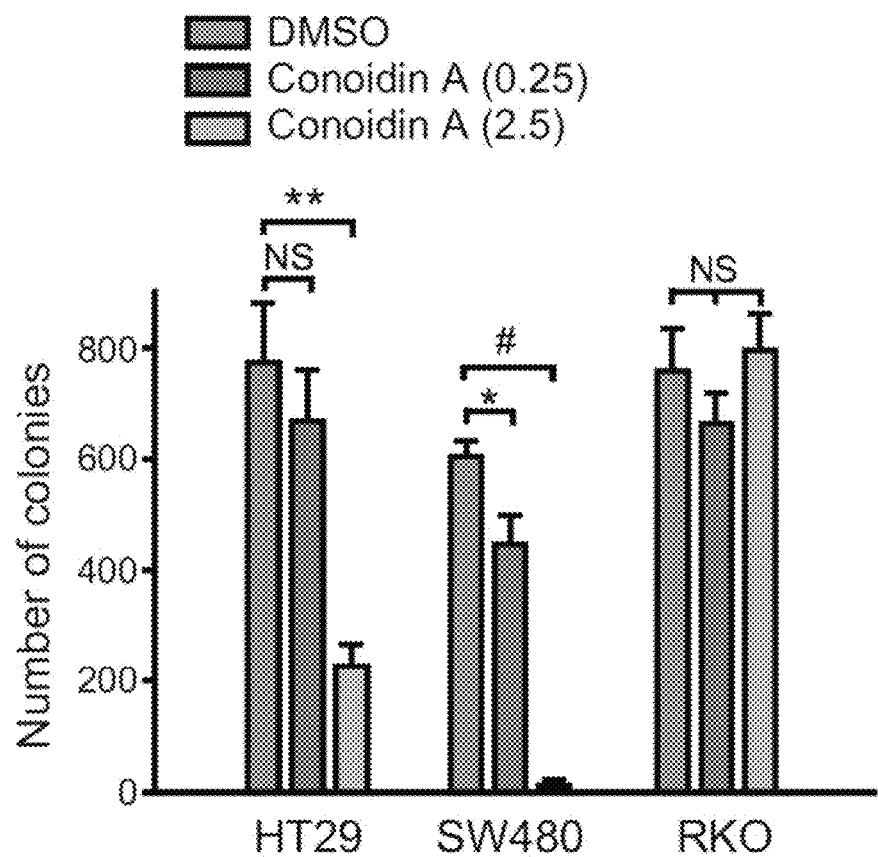
FIG. 64 shows an image and a graph illustrating the results of colony forming assays in colorectal cancer (CRC) cell lines pretreated with Compound-6 (Conoidin A) according to an embodiment of the present invention.

The colony forming assay in FIG. 64 showed that Compound 6 (Conoidin A) treatment sufficiently inhibited the proliferation of HT29 and SW480 cells but not RKO cells. This results suggest that the therapeutic potential of PrxII inhibition to selectively target human APC-mutant CRC cells.

Figure 65:
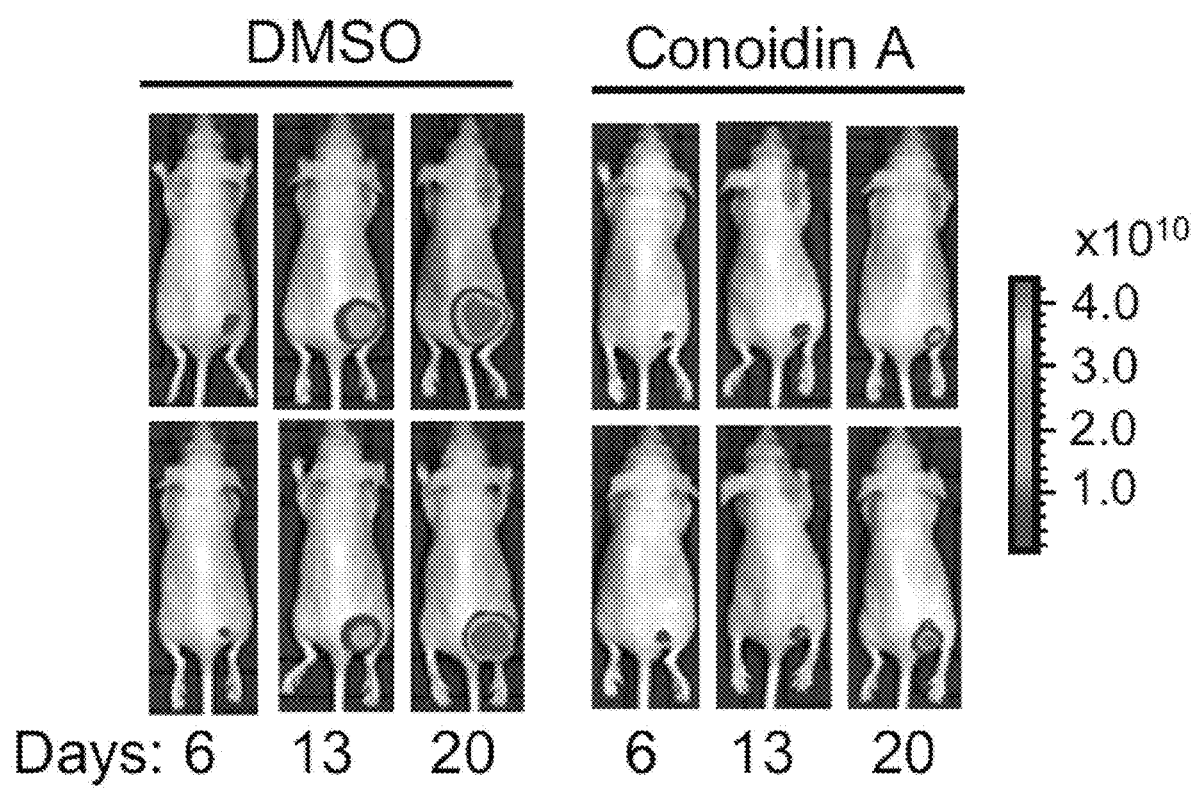
FIGS. 65 and 66 each show the results of luminescence imaging in vivo and weight measurement of tumor growth after transplantation (xenograft), to a mouse, of the colorectal cancer (CRC) cell line, HT29, treated with Compound-6 (Conoidin A) according to an embodiment of the present invention.
Figure 66:
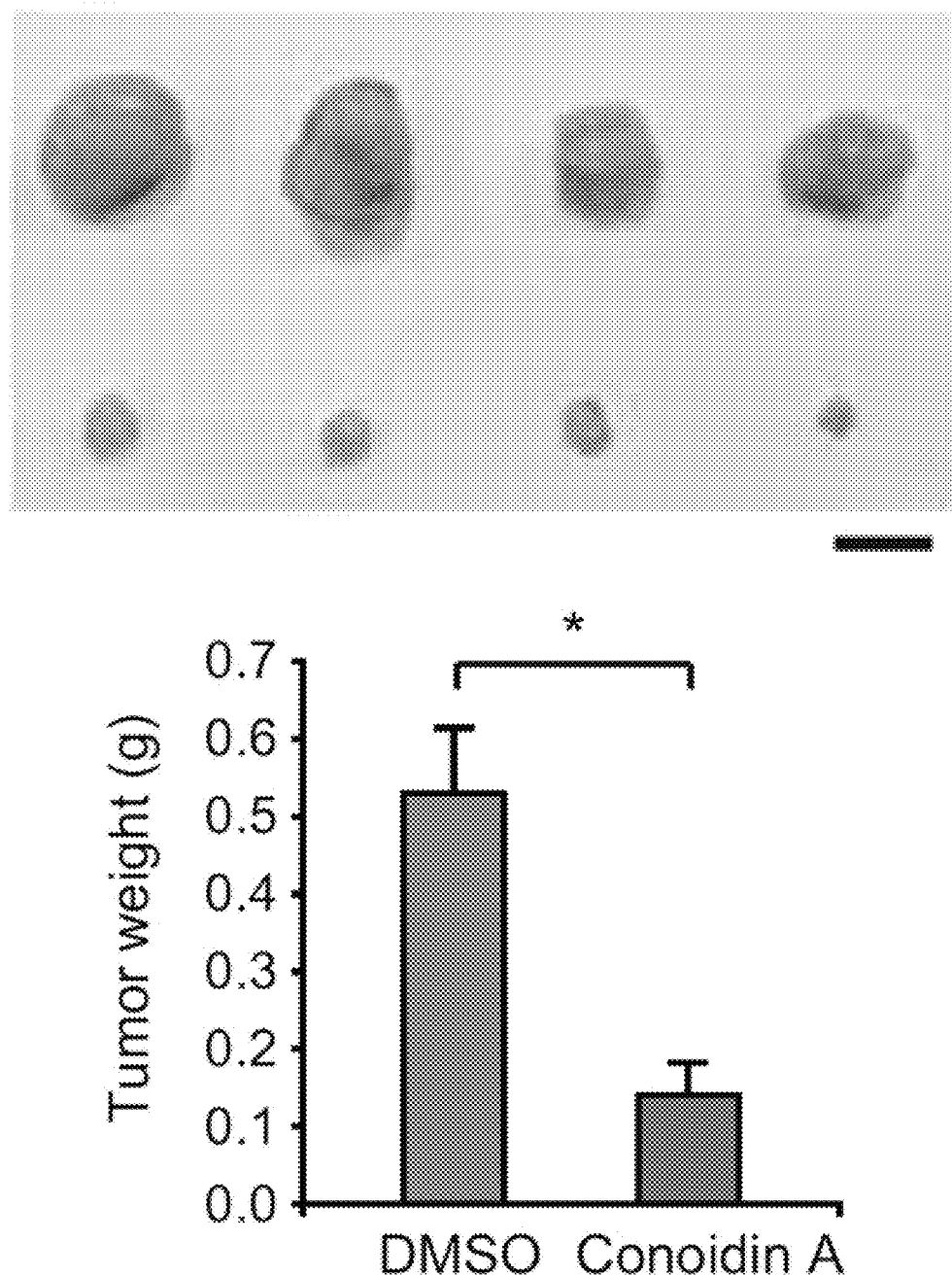

When Compound 6 (Conoidin A) was intraperitoneally injected into mice with a tumor xenograft derived from HT29, Compound 6 (Conoidin A) treatment significantly delayed tumor growth compared to the control, as shown in FIGS. 65 and 66.

Figure 67:
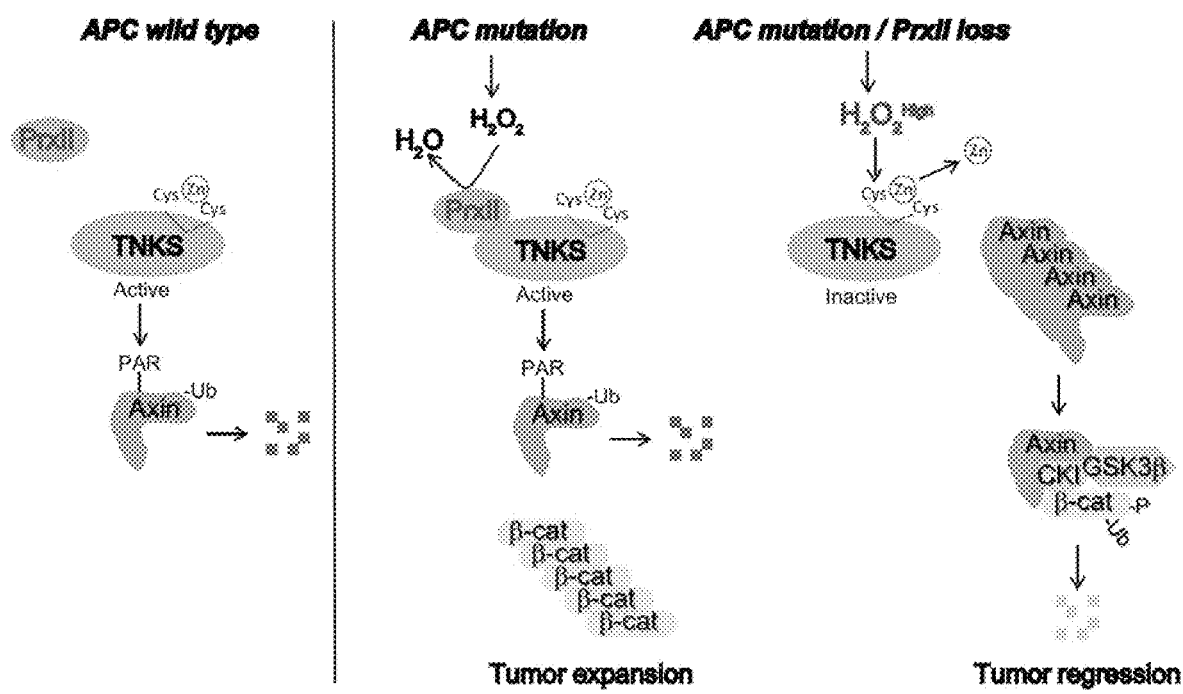
FIG. 67 shows a schematic diagram illustrating the effects of inhibiting CRC by the suppression of the enzyme activity of PrxII according to an embodiment of the present invention.
Figure 68:
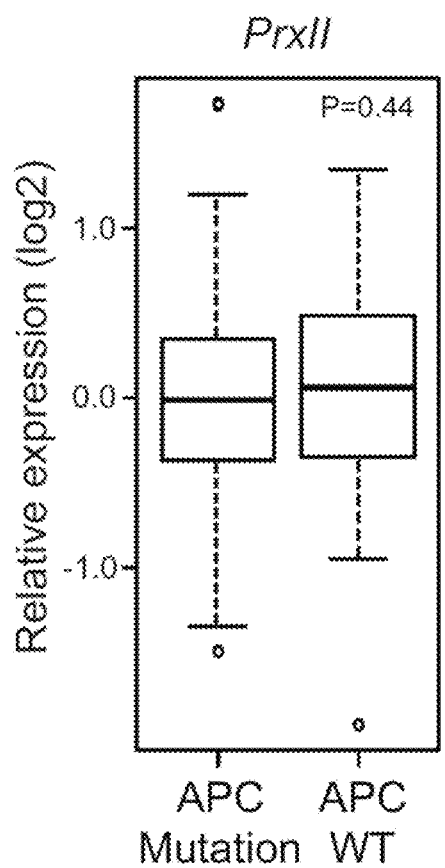
FIG. 68 shows an image illustrating the results of the expression levels of PrxII gene in CRC patients with APC WT or an APC mutation according to an embodiment of the present invention.
Figure 69:
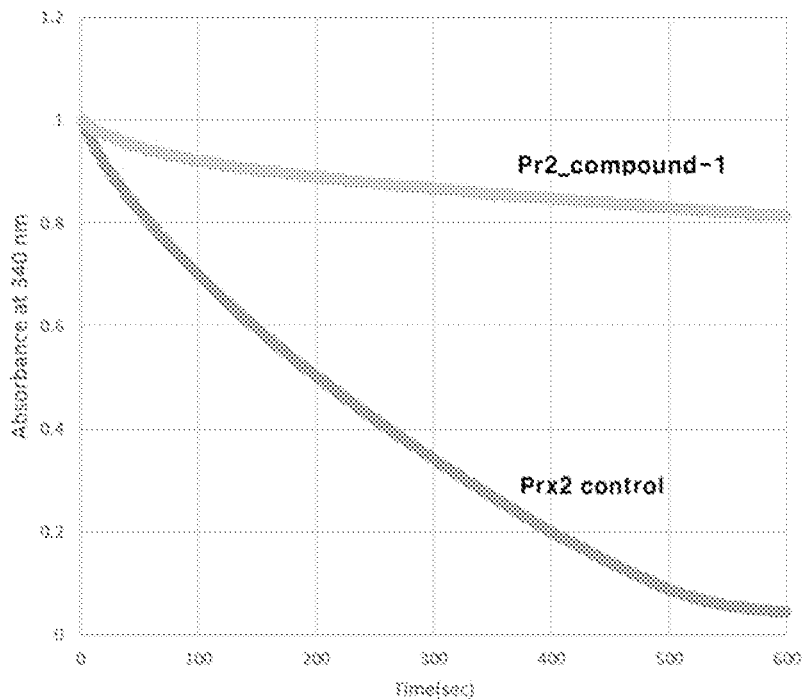
FIG. 69 shows a graph illustrating the results of peroxidase activity measured after reacting PrxII with Compound-1 in vitro according to an embodiment of the present invention.
Figure 70:
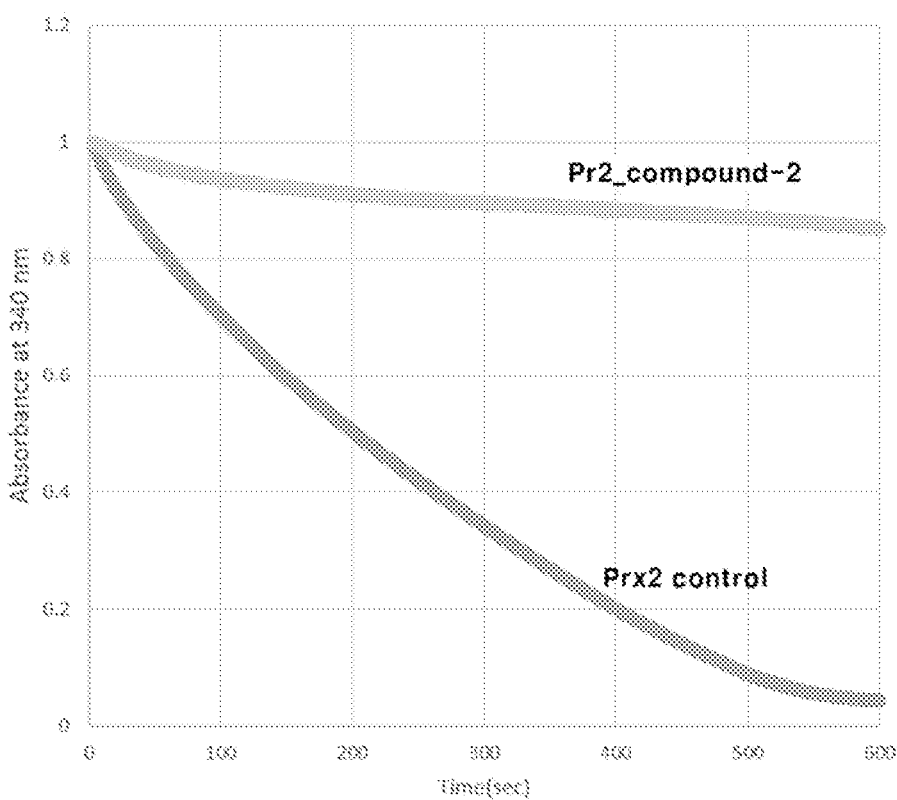
FIG. 70 shows a graph illustrating the results of peroxidase activity measured after reacting PrxII with Compound-2 in vitro according to an embodiment of the present invention.
Figure 71:
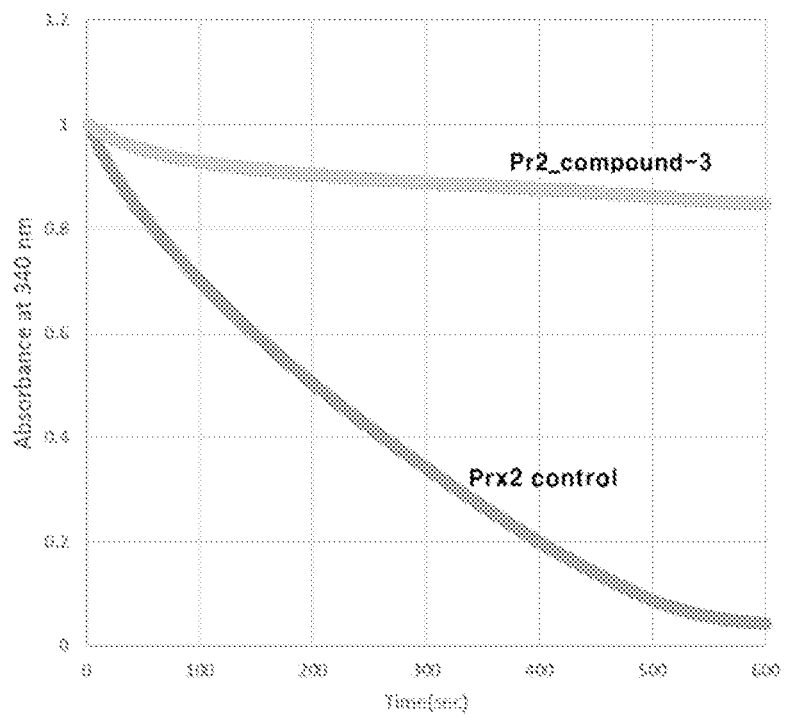
FIG. 71 shows a graph illustrating the results of peroxidase activity measured after reacting PrxII with Compound-3 in vitro according to an embodiment of the present invention.

From these results, it was indicated that PrxII may be a new target treatment for human CRC, and a compound that inhibits PrxII, such as Compound 6 (Conoidin A), can be a new therapeutic drug for human CRC, as shown in the schematic diagram of FIG. 67.

Hereinafter, the synthesis method of Compound-1 to Compound-5 will be described in Synthesis Examples. Compound-6 is Conoidin A and is widely sold by Candia Thamtech Company Limited: Shanghai YuLue Chemical Co., Ltd., etc.

<Synthetic Example 1> Synthesis of 2,3-bis(bromomethyl)-6-methoxyquinoxaline 1,4-dioxide (Compound-1)

Step 1

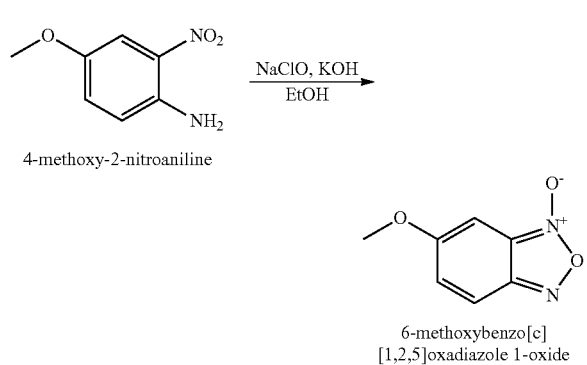

4-methoxy-2-nitroaniline 6-methoxybenzo[c][1,2,5]oxadiazole 1-oxide

4-Methoxy-2-nitroaniline (1.01 g, 5.89 mmol) was added to a 20% KOH/ethanol solution (35 mL) prepared in advance and stirred. About 30 mL of 12% NaOCl solution was added thereto in an ice bath and warmed to room temperature and the solution was stirred until the starting material disappeared.

The solid generated was filtered and washed with cold ethanol. The thus-obtained yellow solid was subjected to a recrystallization process using a solution (water:ethanol=1:3) (0.65 g, 66%).

$^1$H-NMR (400 MHz, CDC$_3$) δ 7.47-6.40 (m, 3H), and 3.90 (s, 3H).

Step 2

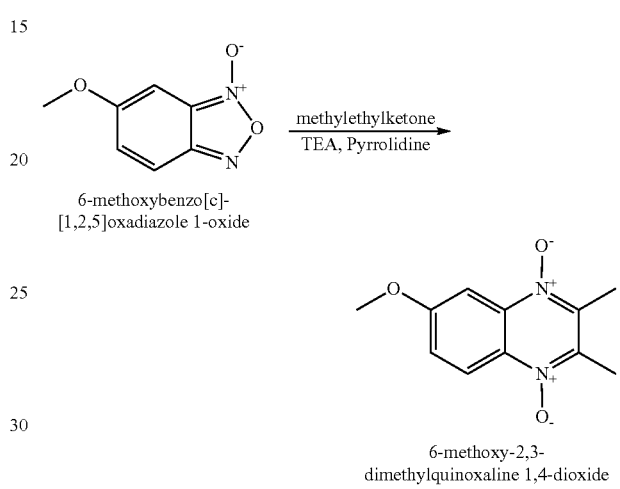

6-methoxybenzo[c]-[1,2,5]oxadiazole 1-oxide 6-methoxy-2,3-dimethylquinoxaline 1,4-dioxide 6-Methoxybenzo[c][1,2,5]oxadiazole 1-oxide (1.00 g, 6.02 mmol) was stirred with trimethylamine (18.06 mmol). Pyrrolidine (0.78 g, 10.83 mmol) and methylethylketone (0.65 g, 9.03 mmol) were added dropwise in an ice bath.

The termination of reaction was confirmed about one hour after increasing the temperature to room temperature (TLC analysis conditions, n-hexane:EtOAc=2:1). The reaction solution was filtered and then washed with cold ethanol to obtain a brown solid (1.06 g, 80%). In this step, the reaction was proceeded to the next step without further purification.

$^1$H-NMR (400 MHz, DMSO-d$_6$) δ 8.36 (d, J=9.6 Hz, 1H), 7.78 (d, J=2.0 Hz, 1H), 7.49 (dd, J=9.0 Hz, 3.0 Hz, 1H) 3.97 (s, 3H), 2.59 (s, 3H), and 2.56 (s, 3H).

Step 3

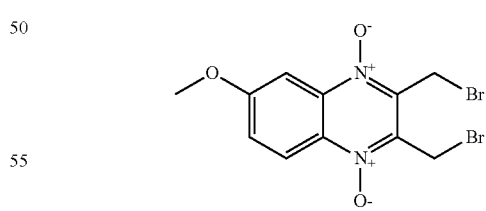

6-Methoxy-2,3-dimethylquinoxaline 1,4-dioxide (1.00 g, 4.54 mmol) was dissolved in 1,4-dioxane, and bromine (12.71 mmol) was added dropwise to the mixture.

The reaction solution was heated up to 90° C. and reacted for about two hours until the spot of the starting material disappeared. In particular, the reaction progress was determined using TLC analysis (n-hexane:EtOAc=1:2).

After completion of the reaction, an aqueous NaHCO$_3$ solution was added thereto and the mixture was extracted with ethyl acetate. Then, the resulting organic layer was washed with brine, dried over MgSO$_4$, filtered, and concentrated to obtain a product in a mixed state. This product was columned using MPLC (n-hexane:EtOAc=3:1) to obtain Compound-1 (1.15 g, 65%).

$^1$H-NMR (400 MHz, DMSO-d$_6$) δ 8.39 (d, J=9.6 Hz, 1H), 7.81 (d, J=2.4 Hz), 7.59 (dd, J=7.4 Hz, 2.2 Hz), 5.06 (s, 4H), and 4.01 (s, 3H); $^{13}$C-NMR (100 MHz, DMSO-d$_6$) δ 162.9, 124.4, 122.2, 99.5, 57.0, 23.5, and 23.4; HRMS (ESI): m/z 377.9038 [M+H]$^+$ (calcd for C$_{11}$H$_{10}$Br$_2$N$_2$O$_3$$^+$ 378.9170)

<Synthetic Example 2> Synthesis of 2,3-bis(bromomethyl)-6-ethoxyquinoxaline 14-dioxide) (Compound-2)

Step 1

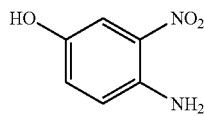

4-amino-3-nitrophenol

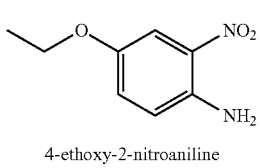

4-ethoxy-2-nitroaniline

A subdivision of potassium carbonate (6.73 g, 48.66 mmol) was added while stirring 4-amino-3-nitrophenol (5.00 g, 32.44 mmol) and bromoethane (5.30 g, 48.66 mmol) in DMF solvent.

Then, the reaction vessel was heated to 90° C. and the reaction was performed for about three hours and observed until the starting material disappeared (TLC analysis conditions, n-hexane:EtOAc=3:1).

After completion of the reaction, the reaction solution was cooled to room temperature and added to ice water. The solid generated was filtered to obtain a red solid in a mixed state. The resultant was purified through a column (n-hexane: EtOAc=10:1) and obtained 4-ethoxy-2-nitroaniline (4.25 g, 72%).

$^1$H-NMR (400 MHz, CDCl$_3$) δ 7.55 (bs, 1H), 7.07 (d, J=8 Hz, 1H), 6.77 (d, J=8 Hz, 1H), 5.89 (bs, 2H), 4.01 (m, 2H), and 1.41 (t, J=6.0 Hz, 3H).

Step 2

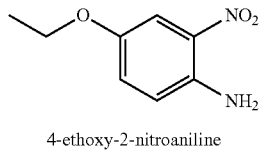

4-ethoxy-2-nitroaniline

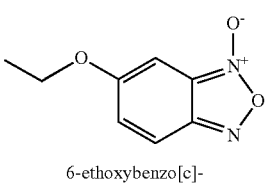

6-ethoxybenzo[c]-
[1,2,5]oxadiazole 1-oxide

4-Ethoxy-2-nitroaniline (2.00 g, 10.98 mmol) was added to a 20% KOH/ethanol solution (60 mL) prepared in advance and stirred.

About 50 mL of a 12% NaOCl solution was added dropwise thereto in an ice bath, and the mixture was warmed to room temperature and stirred until the starting material disappeared. The solid generated was filtered and washed with cold ethanol. The thus-obtained yellow solid was subjected to a recrystallization process using a solution (water:ethanol=1:3 solution) (1.85 g, 94%).

$^1$H-NMR (400 MHz, CDCl$_3$) δ 7.49-6.34 (m, 3H), 4.08 (m, 2H), and 1.48 (t, J=8.0 Hz, 3H)

Step 3

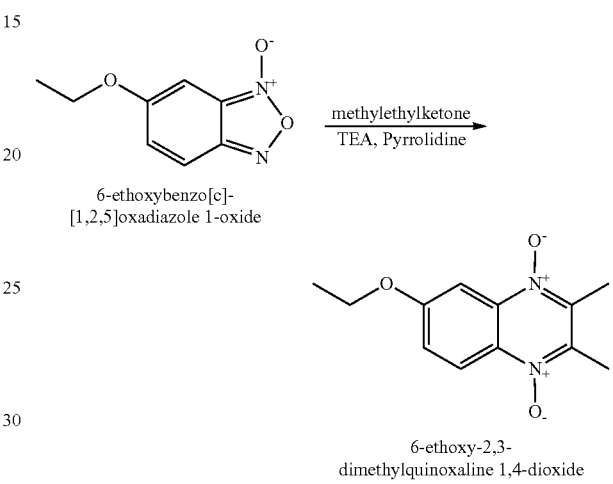

6-ethoxybenzo[c]-
[1,2,5]oxadiazole 1-oxide 6-ethoxy-2,3-
dimethylquinoxaline 1,4-dioxide 6-Ethoxybenzo[c][1,2,5]oxadiazole 1-oxide) (1.50 g, 8.33 mmol) was stirred with trimethylamine (2.52 g, 24.98 mmol).

Pyrrolidine (1.08 g, 14.99 mmol) and methylethylketone (0.90 g, 12.49 mmol) were added dropwise in an ice bath.

The reaction was terminated about one hour after the reaction temperature was raised to room temperature (TLC analysis conditions, n-hexane:EtOAc=2:1). The reaction solution was filtered and washed with cold ethanol to obtain a brown solid (1.11 g, 57%). In this step, the reaction was proceeded to the next step without further purification.

$^1$H-NMR (400 MHz, DMSO-d$_6$) δ 8.51 (d, J=9.6 Hz, 1H), 7.90 (d, J=2.4 Hz, 1H), 7.38 (dd, J=9.4, 2.6 Hz, 1H), 4.24 (m, 2H), 2.74 (s, 3H), 2.71 (s, 3H), and 1.51 (t, J=6.8 Hz, 3H).

Step 4

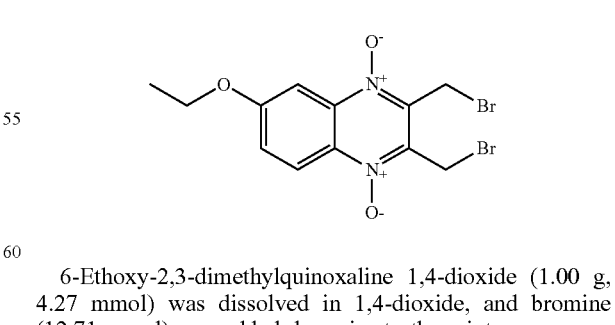

6-Ethoxy-2,3-dimethylquinoxaline 1,4-dioxide (1.00 g, 4.27 mmol) was dissolved in 1,4-dioxane, and bromine (12.71 mmol) was added dropwise to the mixture.

The reaction solution was heated up to 90° C. and reacted for about two hours until the spot of the starting material disappeared. In particular, the reaction progress was determined using TLC analysis (n-hexane:EtOAc=1:2). After completion of the reaction, an aqueous NaHCO$_3$ solution was added thereto and the mixture was extracted with ethyl acetate.

Then, the resulting organic layer was washed with brine, dried over MgSO$_4$, filtered, and concentrated to obtain a product in a mixed state. This product was columned using MPLC (n-hexane:EtOAc=3:1) to obtain Compound-2 (0.98 g, 61%).

$^1$H-NMR (400 MHz, DMSO-d$_6$) δ 8.52 (d, J=9.2 Hz, 1H), 7.90 (d, J=2.4 Hz, 1H), 7.42 (dd, J=9.6, 2.8 Hz), 4.90 (s, 4H), 4.24 (m, 2H), and 1.52 (t, J=7.2 Hz, 3H); $^{13}$C-NMR (100 MHz, DMSO-d$_6$) δ 163.2, 122.5, 122.1, 101.2, 58.0, 23.9 and 13.9; HRMS (ESI): m/z 391.9194 [M+H]$^+$ (calcd for C$_{12}$H$_{12}$Br$_2$N$_2$O$_3$$^+$ 392.9155)

<Synthetic Example 3> Synthesis of 2,3-bis(bromomethyl)-6-isopropoxyquinoxaline 1,4-dioxide (Compound-3)

Step 1

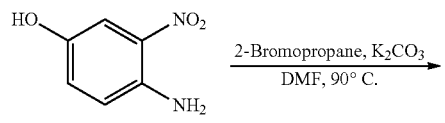

4-amino-3-nitrophenol

2-Bromopropane, K$_2$CO$_3$
DMF, 90° C.

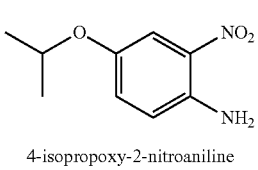

4-isopropoxy-2-nitroaniline

A subdivision of potassium carbonate (6.73 g, 48.66 mmol) was added while stirring 4-amino-3-nitrophenol (5.00 g, 32.44 mmol) and 2-bromopropane (5.98 g, 48.66 mmol) in DMF solvent.

Then, the reaction vessel was heated to 90° C. and the reaction was performed for about five hours and observed until the starting material disappeared (TLC analysis conditions, n-hexane:EtOAc=3:1).

After completion of the reaction, the reaction solution was cooled to room temperature and added to ice water. Then, an extraction was performed with diethyl ether until the spot in the aqueous layer disappeared. The resulting organic layer was washed with brine, dried over MgSO$_4$, and concentrated to obtain a red solid.

This was purified through a column (n-hexane:EtOAc=10:1) and obtained 4-isopropoxy-2-nitroaniline (5.90 g, 93%).

$^1$H-NMR (400 MHz, CDCl$_3$) δ 7.51 (bs, 1H), 7.04 (d, J=8.0 Hz, 1H), 6.75 (d, J=8.0 Hz, 1H), 5.88 (bs, 2H), 4.46 (m, 1H), and 1.33 (d, J=6.0 Hz, 6H).

Step 2

4-isopropoxy-2-nitroaniline

NaClO, KOH
EtOH

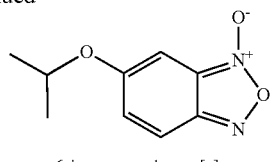

6-isopropoxybenzo[c]-
[1,2,5]oxadiazole 1-oxide

4-Isopropoxy-2-nitroaniline (2.00 g, 10.19 mmol) was added to a 20% KOH/ethanol solution (60 mL) prepared in advance and stirred.

About 50 mL of a 12% NaOCl solution was added dropwise thereto in an ice bath, and the mixture was warmed to room temperature and stirred until the starting material disappeared. The solid generated was filtered and washed with cold ethanol. The thus-obtained yellow solid was subjected to a recrystallization process using a solution (water:ethanol=1:3) (1.93 g, 97%).

$^1$H-NMR (400 MHz, CDCl$_3$) δ 7.48-6.34 (m, 3H), 4.60 (m, 1H), and 1.41 (d, J=6.0 Hz, 6H).

Step 3

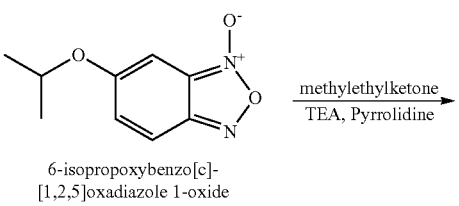

6-isopropoxybenzo[c]-
[1,2,5]oxadiazole 1-oxide methylethylketone
TEA, Pyrrolidine

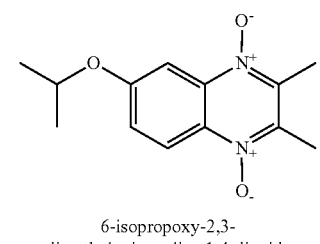

6-isopropoxy-2,3-
dimethylquinoxaline 1,4-dioxide

6-Isopropoxybenzo[c][1,2,5]oxadiazole 1-oxide) (1.50 g, 7.72 mmol) was stirred with trimethylamine (2.34 g, 23.17 mmol).

Pyrrolidine (1.00 g, 13.90 mmol) and methylethylketone (0.84 g, 11.59 mmol) were added dropwise in an ice bath. The reaction was terminated about one hour after the temperature was increased to room temperature (TLC analysis conditions, n-hexane:EtOAc=2:1). The reaction solution was filtered and washed with cold ethanol to obtain a brown solid (1.49 g, 78%). In this step, the reaction was proceeded to the next step without further purification.

$^1$H-NMR (400 MHz, DMSO-d$_6$) δ 8.50 (d, J=9.6 Hz, 1H), 7.91 (d, J=2.4 Hz, 1H), 7.34 (dd, J=9.4 Hz, 2.6 Hz, 1H) 4.81 (s, 1H), 2.73 (s, 3H), 2.71 (s, 3H), and 1.44 (d, J=6.0 Hz, 3H).

Step 4

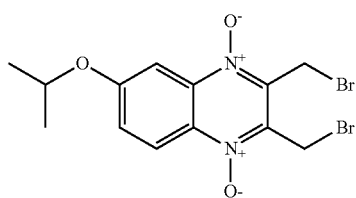

6-Isoproxy-2,3-dimethylquinoxaline 1,4-dioxide (1.00 g, 4.03 mmol) was dissolved in 1,4-dioxane, and bromine (12.71 mmol) was added dropwise to the mixture.

The reaction solution was heated up to 90° C. and reacted for about two hours until the spot of the starting material disappeared. In particular, the reaction progress was determined by TLC analysis (n-hexane:EtOAc=1:2).

After completion of the reaction, an aqueous NaHCO$_3$ solution was added thereto and the resultant was extracted with ethyl acetate. The resulting organic layer was washed with brine, dried over MgSO$_4$, filtered, and concentrated to obtain a product in a mixed state. This product was columned using MPLC (n-hexane:EtOAc=3:1) to obtain Compound-3 (0.69 g, 42%).

$^1$H-NMR (400 MHz, DMSO-d$_6$) δ 8.52 (d, J=9.2 Hz, 1H), 7.90 (d, J=2.4 Hz, 1H), 7.42 (dd, J=9.6, 2.8 Hz), 4.90 (s, 4H), 4.24 (m, 2H), and 1.52 (t, J=7.2 Hz, 3H); $^{13}$C-NMR (100 MHz, DMSO-d$_6$) δ 162.9, 122.70, 105.7, 73.0, 23.9 and 21.8; HRMS (ESI): m/z 405.9351 [M+H]$^+$ (calcd for C$_{13}$H$_{14}$Br$_2$N$_2$O$_3$$^+$ 406.9458)

<Synthetic Example 4> Synthesis of 6-(allyloxy)-2, 3-bis(bromomethyl)quinoxaline 1,4-dioxide) (Compound-4)

Step 1

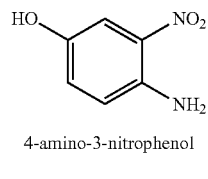

4-amino-3-nitrophenol

Allyl bromide, K$_2$CO$_3$
DMF, 90° C.

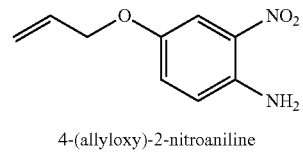

4-(allyloxy)-2-nitroaniline

A subdivision of potassium carbonate (6.73 g, 48.66 mmol) was added while stirring 4-amino-3-nitrophenol (5.00 g, 32.44 mmol) and allyl bromide (5.89 g, 48.66 mmol) in DMF solvent.

Then, the reaction vessel was heated to 90° C. and the reaction was performed and observed for about three hours until the starting material disappeared (TLC analysis conditions, n-hexane:EtOAc=3:1).

After completion of the reaction, the reaction solution was cooled to room temperature and added to ice water. Then, an extraction was performed with diethyl ether until the spot in the aqueous layer disappeared. The resulting organic layer was washed with brine, dried over MgSO$_4$, and concentrated to obtain a red solid.

This was purified through a column (n-hexane:EtOAc=10:1) and obtained 4-(allyloxy)-2-nitroaniline (4.44 g, 71%).

$^1$H-NMR (400 MHz, CDCl$_3$) δ 7.52 (bs, 1H), 7.00 (d, J=7.6 Hz, 1H), 6.73 (d, J=8.0 Hz, 1H), 6.06 (m, 1H), 5.60 (bs, 2H), 5.47 (d, J=16.0 Hz, 1H), 5.34 (d, J=10.4 Hz, 1H), and 4.70 (d, J=5.2 Hz, 2H).

Step 2

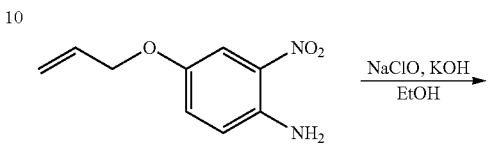

4-(allyloxy)-2-nitroaniline

NaClO, KOH
EtOH

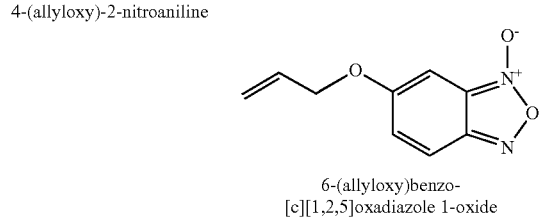

6-(allyloxy)benzo-
[c][1,2,5]oxadiazole 1-oxide

4-Allyloxy-2-nitroaniline (2.00 g, 10.30 mmol) was added to a 20% KOH/ethanol solution (60 mL) prepared in advance and stirred.

About 50 mL of a 12% NaOCl solution was added dropwise thereto in an ice bath, and the mixture was warmed to room temperature and stirred until the starting material disappeared. The solid generated was filtered and washed with cold ethanol. The thus-obtained yellow solid was subjected to a recrystallization process using a solution (water:ethanol=1:3 solution (1.96 g, 99%).

$^1$H-NMR (400 MHz, CDCl3) δ 7.76-6.69 (m, 3H), 6.06 (m, 1H).

Step 3:

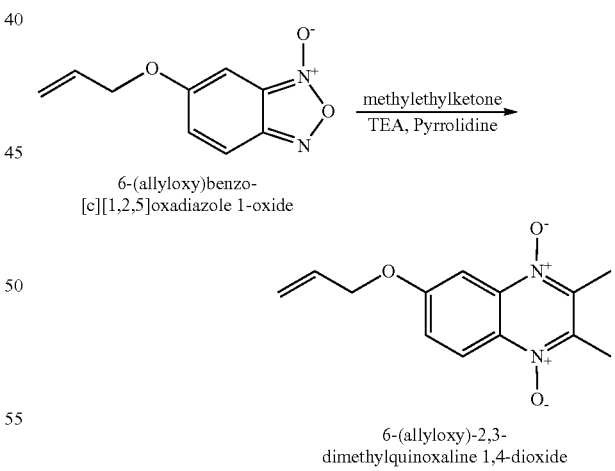

6-(allyloxy)benzo-
[c][1,2,5]oxadiazole 1-oxide methylethylketone
TEA, Pyrrolidine 6-(allyloxy)-2,3-
dimethylquinoxaline 1,4-dioxide 6-(Allyloxy)benzo[c][1,2,5]oxadiazole 1-oxide (1.50 g, 7.81 mmol) was stirred with trimethylamine (2.36 g, 23.42 mmol).

Pyrrolidine (1.01 g, 14.05 mmol) and methylethylketone (0.84 g, 11.71 mmol) were added dropwise thereto. The termination of reaction was confirmed about one hour after increasing the temperature to room temperature (TLC analysis conditions, n-hexane:EtOAc=2:1). The reaction solution was filtered and then washed with cold ethanol to obtain a brown solid (0.96 g, 50%). In this step, the reaction was proceeded to the next step without further purification.

¹H-NMR (400 MHz, DMSO-$d_6$) δ 8.38 (d, J=9.6 Hz, 1H), 7.82 (d, J=2.4 Hz, 1H), 7.52 (dd, J=9.4, 2.4 Hz, 1H), 6.10 (m, 1H), 5.57 (dd, J=17.2, 1.6 Hz, 1H), 5.34 (dd, J=10.6, 1.6 Hz, 1H), 2.59 (s, 3H), 2.57 (s, 3H).

Step 4:

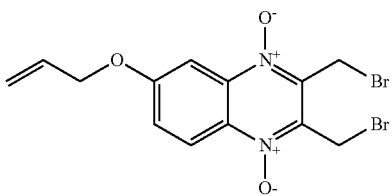

6-(Allyloxy)-2,3-dimethylquinoxaline 1,4-dioxide (1.00 g, 4.06 mmol) was dissolved in 1,4-dioxane, and bromine (12.71 mmol) was added dropwise to the mixture.

The reaction solution was heated up to 90° C. and reacted for about two hours until the spot of the starting material disappeared. In particular, the reaction progress was determined using TLC analysis (n-hexane:EtOAc=1:2). After completion of the reaction, an aqueous NaHCO₃ solution was added thereto and the resultant was extracted with ethyl acetate. Then, the resulting organic layer was washed with brine, dried over MgSO₄, filtered, and concentrated to obtain a product in a mixed state.

This product was columned using MPLC (n-hexane:EtOAc=3:1) to obtain Compound-4 (0.72 g, 44%).

¹H-NMR (400 MHz, DMSO-$d_6$) δ 8.25 (d, J=9.6 Hz, 1H), 7.90 (m, 2H), 5.87 (m, 1H) 5.23-5.17 (m, 2H), 4.92 (s, 4H), and 4.61 (d, J=4.8 Hz, 2H); ¹³C-NMR (100 MHz, DMSO-$d_6$) δ 167.0, 134.5, 122.3, 122.1, 117.5, 105.0, 70.1, and 23.9 HRMS (ESI): m/z 403.9194 [M+H]⁺ (calcd for $C_{13}H_{12}Br_2N_2O_3^+$ 404.9279)

<Synthetic Example 5> Synthesis of 2,3-bis(bromomethyl)-6-(prop-2-ynyloxy)quinoxaline 1,4-dioxide (Compound-5)

Step 1:

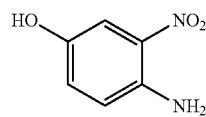

4-amino-3-nitrophenol

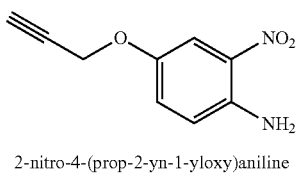

2-nitro-4-(prop-2-yn-1-yloxy)aniline

A subdivision of potassium carbonate (6.73 g, 48.66 mmol) was added while stirring 4-amino-3-nitrophenol (5.00 g, 32.44 mmol) and propargyl bromide (5.79 g, 48.66 mmol) in DMF solvent. Then, the reaction vessel was heated to 90° C. and the reaction was performed and observed for about three hours until the starting material disappeared (TLC analysis conditions, n-hexane:EtOAc=3:1).

After completion of the reaction, the reaction solution was cooled to room temperature and added to ice water. Then, an extraction was performed diethyl ether until the spot in the aqueous layer disappeared. The resulting organic layer was washed with brine, dried over MgSO₄, and concentrated to obtain a red solid.

This finally confirmed 2-nitro-4-(prop-2-yn-1-yloxy)aniline (3.95 g, 63%) through a column (n-hexane:EtOAc=10:1).

¹H-NMR (400 MHz, CDCl₃) δ 7.69 (bs, 1H), 7.13 (d, J=8.0 Hz, 1H), 6.78 (d, J=8.0 Hz, 1H), 5.91 (bs, 2H), 4.67 (d, J=4.0 Hz, 2H), and 2.55 (t, J=2.0 Hz, 1H).

Step 2:

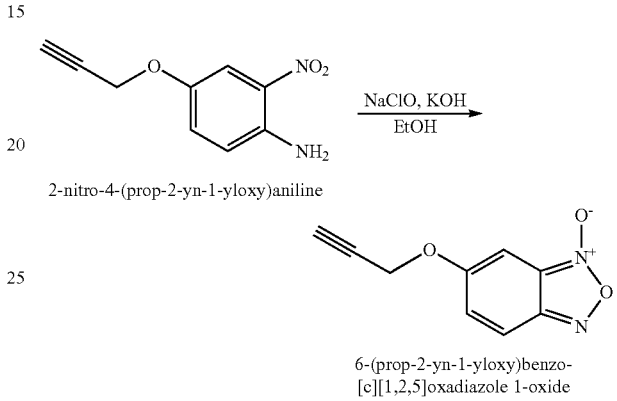

2-nitro-4-(prop-2-yn-1-yloxy)aniline 6-(prop-2-yn-1-yloxy)benzo-[c][1,2,5]oxadiazole 1-oxide 2-Nitro-4-(prop-2-yn-1-yloxy) aniline (2.00 g, 10.41 mmol) was added to a 20% KOH/ethanol solution (60 mL) prepared in advance and stirred. About 50 mL of 12% NaOCl solution was added thereto in an ice bath and the mixture was warmed to room temperature and stirred until the starting material disappeared.

The solid generated was filtered and washed with cold ethanol. The thus-obtained yellow solid was subjected to a recrystallization process using a solution (water:ethanol=1:3) (1.96 g, 99%).

¹H-NMR (400 MHz, CDCl₃) δ 7.81-6.81 (m, 3H), 4.98 (d, J=2.0 Hz, 2H), and 3.34 (s, 1H).

Step 3:

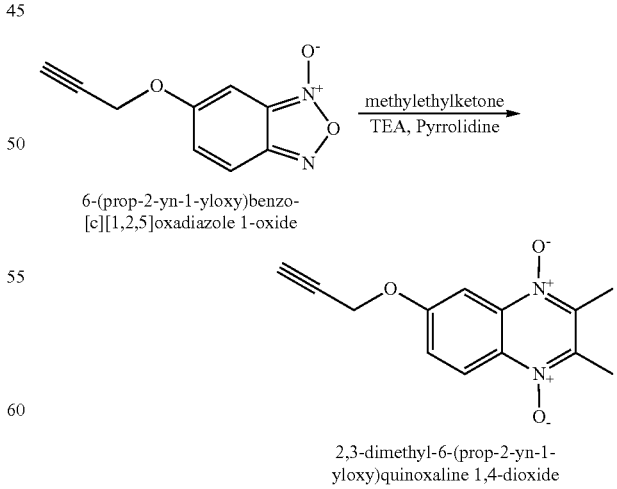

6-(prop-2-yn-1-yloxy)benzo-[c][1,2,5]oxadiazole 1-oxide 2,3-dimethyl-6-(prop-2-yn-1-yloxy)quinoxaline 1,4-dioxide 6-(Prop-2-yn-1-yloxy)benzo[c][1,2,5]oxadiazole 1-oxide) (1.50 g, 7.89 mmol) was stirred with trimethylamine (2.39 g, 23.66 mmol).

Pyrrolidine (1.02 g, 14.20 mmol) and methylethylketone (0.85 g, 11.83 mmol) were added dropwise in an ice bath. The termination of reaction was confirmed about one hour after increasing the temperature to room temperature (TLC analysis conditions, n-hexane:EtOAc=2:1). The reaction solution was filtered and then washed with cold ethanol to obtain a brown solid (0.96 g, 51%). In this step, the reaction was proceeded to the next step without further purification.

$^1$H-NMR (400 MHz, DMSO-$d_6$) δ 8.38 (d, J=9.6 Hz, 1H), 7.92 (d, J=2.4, 1H), 7.51 (dd, J=9.4, 2.6 Hz, 1H), 5.06 (d, J=2.4 Hz, 2H), 3.71 (t, J=2.4 Hz, 1H), 2.59 (s, 1H), 2.57 (s, 1H).

Step 4:

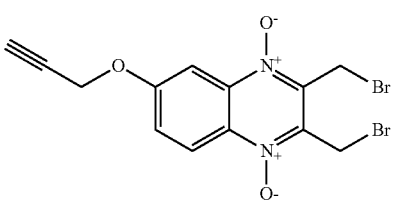

A 2,3-dimethyl-6-(prop-2-ynyloxy)quinoxaline 1,4-dioxide (1.00 g, 4.09 mmol) was dissolved in 1,4-dioxide, and bromine (12.71 mmol) was added thereto.

The reaction solution was heated up to 90° C. and reacted for about two hours until the spot of the starting material disappeared. In particular, the reaction progress was determined using TLC analysis (n-hexane:EtOAc=1:2). After completion of the reaction, an aqueous NaHCO$_3$ solution was added thereto and the resultant was extracted with ethyl acetate.

Then, the resulting organic layer was washed with brine, dried over MgSO$_4$, filtered, and concentrated to obtain a product in a mixed state. This product was columned using MPLC (n-hexane:EtOAc=3:1) to obtain Compound-5 (0.68 g, 41%).

$^1$H-NMR (400 MHz, DMSO-$d_6$) δ 8.34 (d, J=9.6 Hz, 1H), 8.06 (m, 2H); 5.00 (s, 4H), 4.86 (d, J=2.4 Hz, 2H) and 3.51 (t, J=2.4 Hz, 1H); $^{13}$C-NMR (100 MHz, DMSO-$d_6$) δ 164.8, 122.2, 120.6, 106.3, 80.0, 78.8, 58.8 and 23.1; HRMS (ESI): m/z 401.9038 [M+H]$^+$ (calcd for $C_{13}H_{10}Br_2N_2O_3^+$ 402.9465)

<Example 17> Analysis of Regulation of PrxII Activity by Compound-1 to Compound-5

To evaluate the possibility of treating human CRC by inhibiting PrxII, cell-permeability of Compound-1 to Compound-5 were tested.

Figure 72:
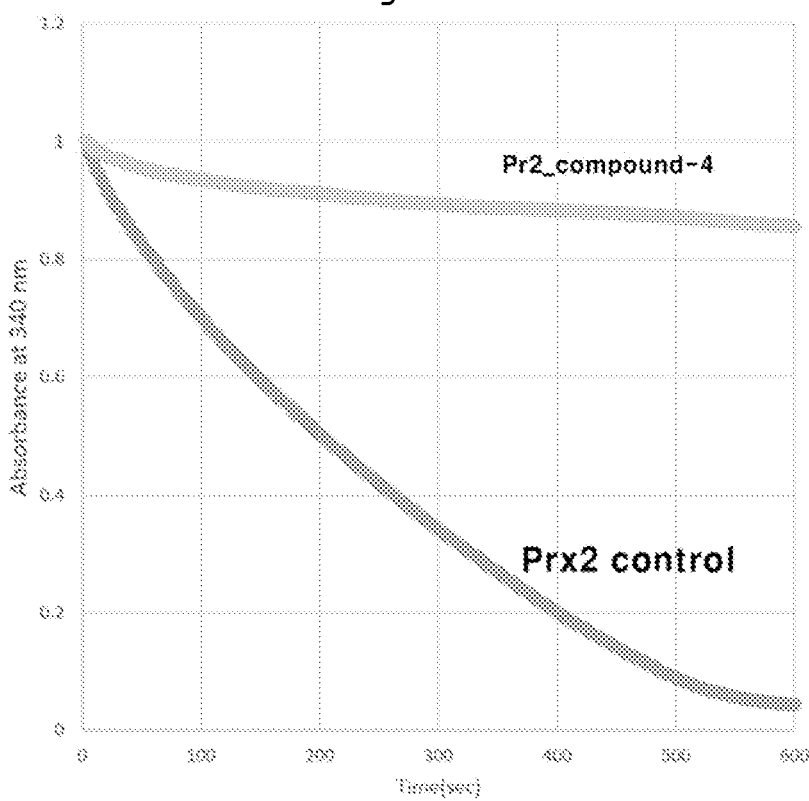
FIG. 72 shows a graph illustrating the results of peroxidase activity measured after reacting PrxII with Compound-4 in vitro according to an embodiment of the present invention.
Figure 73:
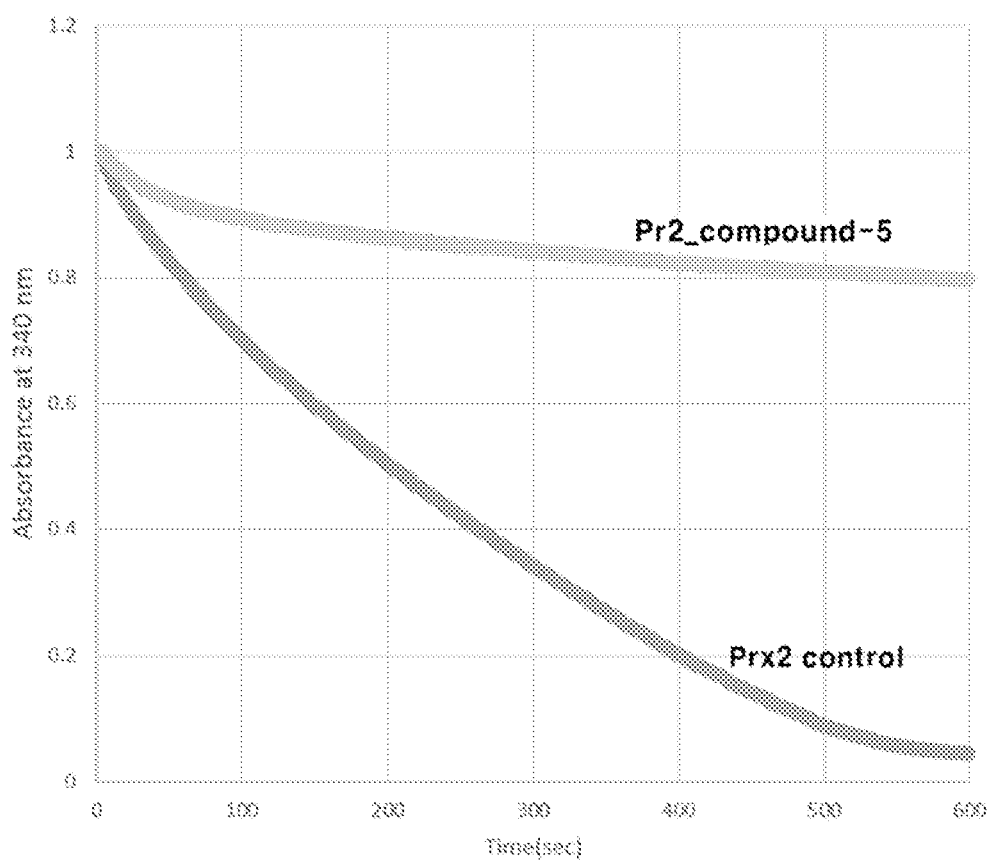
FIG. 73 shows a graph illustrating the results of peroxidase activity measured after reacting PrxII with Compound-5 in vitro according to an embodiment of the present invention.

In the graphs of FIGS. 72 and 73, it confirmed that Compound-1 to Compound-5 synthesized according to an embodiment of the present invention significantly inhibited PrxII activity.

<Example 18> Colony Forming Assay by Compound-1 to Compound-5

Figure 74A:
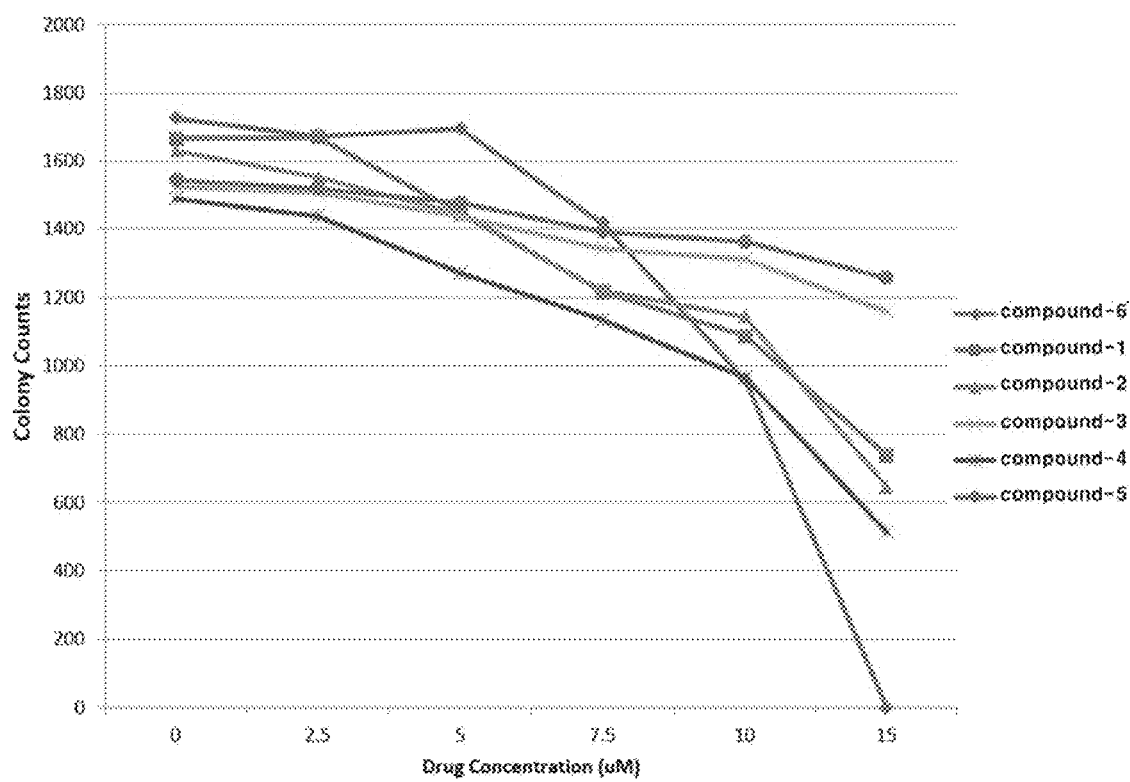
Figure 75A:
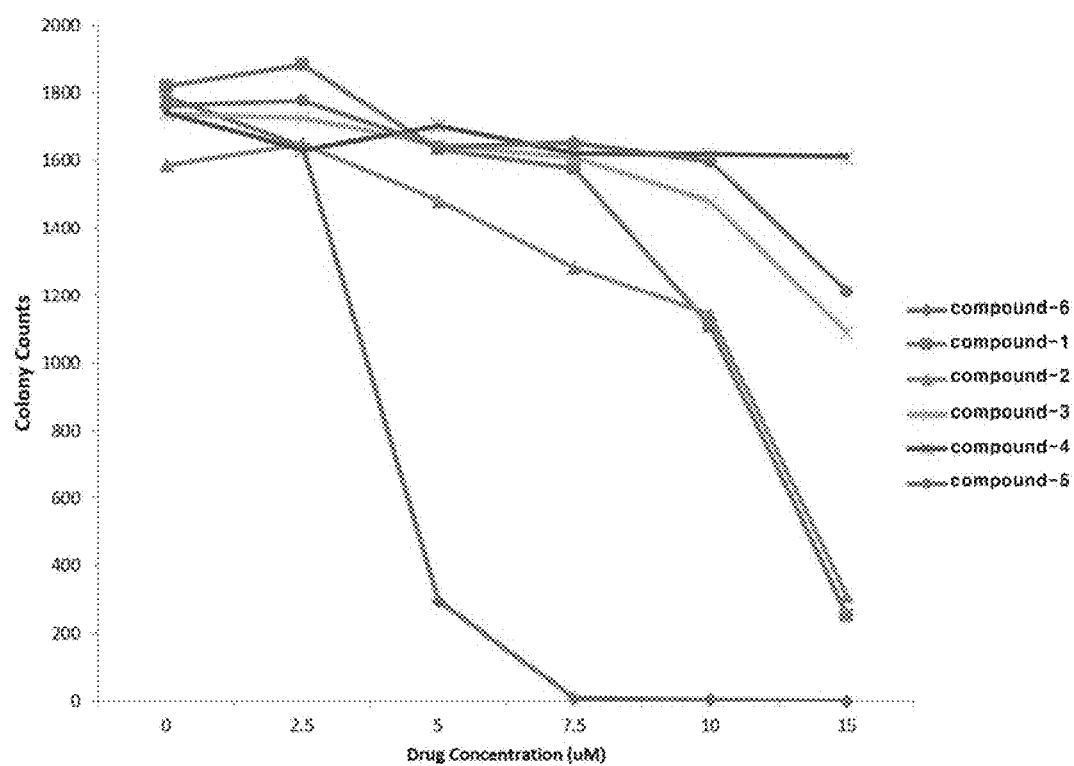

FIG. 74 shows a graph illustrating the results of the number of colonies after treatment of Compound-1 to Compound-5 in RKO cells. FIG. 75 shows the results of colony forming assay obtained by culturing RKO cells after treating with Compound-1 to Compound-5 and Conoidin A (Compound-6).

FIG. 76 shows a graph illustrating the results of the number of colonies after treatment of Compound-1 to Compound-5 in HT29 cells. FIG. 77 shows the results of colony forming assay obtained by culturing HT29 cells after treating with Compound-1 to Compound-5 and Conoidin A (Compound-6).

These results showed that the treatment with Compound-1 to Compound-5 sufficiently inhibits the proliferation of HT29 cells but not RKO cells. From these results it predicted that PrxII can be a new targeted treatment for human CRC, and compounds that inhibit PrxII, such as Conoidin A (Compound-6) and Compound-1 to Compound-5, can be new therapeutics for human CRC.

<Reference Example 1> Analysis of The Cancer Genome Atlas (TCGA)

The expression of PrxI and PrxII in CRC and normal colorectal tissue samples was measured using microarray data from The Cancer Genome Atlas (TCGA) project (https://tcga-data.nci.nih.gov).

To illustrate, mRNA expression data were generated using the Agilent G4502A microarray platform and then processed and normalized as described previously. For the analysis of gene expression data, 155 CRC tissue samples and 26 normal colorectal tissue samples were included.

<Reference Example 2> Immunoblotting and Immunoprecipitation

The intestinal lumen was washed with ice-filled phosphate buffered saline (PBS) using a syringe with a flat needle and cut longitudinally. Intestinal sections without polyps were excised along with polyps for immunoblotting analysis.

Tissues were homogenized in HEPES-buffered saline containing 10% glycerol, 1 mM EDTA, 2 mM EGTA, 1 mM DTT, 5 mM Na$_3$VO$_4$, 5 mM NaF, 1 mM AEBSF, aprotinin (5 μg/mL), and leupetin (5 μg/mL) using a Dounce homogenizer.

The cultured cells were rinsed once with ice-cold PBS and dissolved in lysis buffer containing 20 mM HEPES (pH 7.0), 1% Triton X-100, 150 mM NaCl, 10% glycerol, 1 mM EDTA, 2 mM EGTA, 1 mM DTT, 5 mM Na$_3$VO$_4$, 5 mM NaF, 1 mM AEBSF, aprotinin (5 μg/mL), and leupetin (5 μg/mL).

Homogenates and cell lysates were centrifuged at 15,000×g for 15 minutes and protein concentrations were examined by Bradford assay (Pierce). Protein samples were mixed with an SDS sample buffer and boiled for 5 minutes.

The proteins were isolated by SDS-PAGE and transferred to nitrocellulose membranes by electroblotting for one hour. The membranes were blocked with 5% bovine serum albumin (BSA) or 5% dried skim milk for two hours in Tris buffered saline containing 0.05% (v/v) Tween-20 (TBST) and then incubated at a constant temperature in blocking buffer along with an appropriate primary antibody at room temperature for two hours.

Then, the membranes, after washing three times with TBST, were incubated with a horseradish peroxidase-conjugated secondary antibody (Amersham Biosciences) in blocking buffer. The immune-reactive bands were detected by a chemiluminescence kit (AbFrontier. Korea) and quantified with a LAS-3000 imaging system (Fuji Film, Japan).

If necessary, the membranes were removed by shaking at 37° C. for 60 minutes in 67 mM Tris (pH 6.7), 2% SDS, and 100 mM β-mercaptoethanol, and re-examined with an appropriate general antibody (pan-antibody).

For immunoprecipitation, purified cell lysates (0.5-1 mg of proteins) were removed in advance with 30 μL of protein-A/G Sepharose 4 Fast Flow beads (Amersham Biosciences) for one hour.

Supernatants (cultures floating on the surface) were incubated with 3 μg of an appropriate antibody overnight, and then, precipitated by mixing with 30 μL of protein-A/G beads at 4° C. for three hours.

Then, the beads were washed three times with 1 mL of lysis buffer, followed by in vitro PARP analysis or immunoblotting.

<Reference Example 3> β-Catenin/TCF Transcription Reporter Assay

SW480 cells were seeded in a 12-well plate and transfected with pTOPflash or pFOPflash plasmid. To normalize transfection efficiency, cells were transfected with pRL-TK renilla Luciferase control plasmid.

After the transfection, cells were incubated for 24 hours in a complete medium and then lysed with reporter lysis buffer. Luciferase activity was measured three times by Dual-Luciferase reporter assay (Promega).

Data were reported as fold induction compared to the control siRNA after normalization of transfection efficiency. As used herein, "fold induction" refers to a ratio of experimental activity to control activity.

<Reference Example 4> RNA Sequence Analysis

Four samples of siRNA-transfected HT29 cells were prepared for high-throughput mRNA sequencing. 1 μg of RNA was extracted from each sample and an mRNA library (an insert size of about 300 bp) was constructed using TruSeq RNA Library Preparation kit v2 (Illumina).

Paired-end transcriptome sequencing (101 bp read length) was performed using Illumina HiSeq 2500. The number of reads for each sample ranged from 69.4 million to 74.8 million. The sequencing data were deposited in the GEO database (Accession Number GSE81429).

After standard quality testing and trimming with FastQC and Fastx-toolkit, RNA sequence data was aligned to the human genome (hg19 of UCSC) using MapSplice v2.1.7. The mapping rate of reads was between 96.5% and 96.8%, and RSG v1.2.12 was used to estimate the amount of transcriptome of refGene mRNA.

Differentially expressed genes (DEG) were identified using DESeq2 with an FDR cutoff of 0.05.

<Reference Example 5> In Vitro PARP Assay

Immunocomplex-bound beads were incubated at 25° C. for 30 minutes in 40 μL of assay buffer (50 mM Tris-HCl, pH 8.0, 4 mM $MgCl_2$) containing 4 μCi of $\gamma$-$^{32}$[P]-NAD$^+$. The reaction was stopped by adding 2×SDS sample buffer. The sample was boiled and separated using an SDS denaturing gel.

The gel was dried under vacuum and radiographed on an imaging plate. Radioactivity recorded on the plate was read and quantified by Fujifilm Bio-imaging Analyzer System (BAS)-3000.

<Reference Example 6> Plasmid Construction and Site-Directed Mutagenesis

A plasmid including the full-length complementary DNA of human tankyrase 1 (TNKS1) was purchased from Open Biosystems (mRNA accession number, BC098394). The entire sequence of tankyrase-1 was PCR-amplified using the forward and reverse primers:

```
                                       (SEQ ID NO: 11)
   5'-ATAAGAATGCGGCCGCGGCGGCGTCGCGTCGCTC-3'
   and
                                       (SEQ ID NO: 12)
   5'-GAAGATCTCTAGGTCTTCTGCTCTG-3'
```

Then, the amplified PCR products was inserted into p3×FLAG CMV9 vector to generate FLAG-tagged tankyrase 1 (TNKS1). For domain mapping experiments, various tankyrase 1 fragments were PCR-amplified and subcloned into the p3×FLAG CMV9 vector using the following forward and reverse primers:

```
   amino acid residue 1-158,
                                       (SEQ ID NO: 13)
   5'-ATAAGAATGCGGCCGCGGCGGCGTCGCGTCGCTC-3'
   and
                                       (SEQ ID NO: 14)
   5'-GAAGATCTCTAGGCCGCCTCGGGGCTCTC-3';

amino acid residue 158-595,
                                       (SEQ ID NO: 15)
   5'-ATAAGAATGCGGCCGCCGGAGTTAGCAGCACAGCAC-3'
   and
                                       (SEQ ID NO: 16)
   5'-GAAGATCTCTACAAAGCAGTCTGACCAAGGG-3';

amino acid residue 596-1022,
                                       (SEQ ID NO: 17)
   5'-ATAAGAATGCGCCGCGCATAGAGCCGCCCTAGCAGG-3'
   and
                                       (SEQ ID NO: 18)
   5'-GAAGATCTCTATCCTTCCTTCCTTTCTGTTCC-3';

amino acid residue 1023-1327,
                                       (SEQ ID NO: 19)
   5'-ATAAGAATGCGGCCGCAGAAGTTGCTGGTCTTGAC-3'
   and
                                       (SEQ ID NO: 20)
   5'-GAAGATCTCTAGGTCTTCTGCTCTG-3'
```

The E. coli expressing plasmid for GST-TNKS1 (1023-1327) was kindly provided by Chang-Woo Lee (School of Medicine, Sungkyunkwan University).

Myc-tagged siRNA-resistant PrxII WT, and a retroviral vector (pQ-CXIX) expressing a C172S single mutant and a C51/172S double mutant were prepared as described above. Site-directed mutagenesis for amino acid substitutions was performed using a QuikChange kit (Stratagene).

The double-stranded primers for Cys-Ser substitution in tankyrase 1 are as follows:

```
   in the case of a C1163S mutant,
   (sense)
                                       (SEQ ID NO: 21)
   5'-GTTGAGGGAGCGGTTCTCCCACCGACAGAAGGAAG-3';

in the case of a C1234S mutant,
   (sense)
                                       (SEQ ID NO: 22)
   5'-GGAGGAGGAACAGGCTCCCCTACACACAAGGAC-3';
```

```
in the case of a C1242S mutant,
(sense)
                                        (SEQ ID NO: 23)
5'-CACAAGGACAGGTCATCCTATATATGTCACAGAC-3';

in the case of a C1245S mutant,
(sense)
                                        (SEQ ID NO: 24)
5'-CAGGTCATGCTATATATCTCACAGACAAATGCTCTTC-3';

in the case of a C1252S mutant,
(sense)
                                        (SEQ ID NO: 25)
5'-GACAAATGCTCTTCTCTAGAGTGACCCTTGGG-3'
```

The double-stranded primers for Gly-Val substitution of human PrxII are as follows:

```
in the case of a G9V mutant,
(sense)
                                        (SEQ ID NO: 26)
5'-GCGCGCATCGTAAAGCCAGCCCCTG-3';

in the case of a G23V mutant,
(sense)
                                        (SEQ ID NO: 27)
5'-GCGGTGGTTGATGTCGCCTTCAAAG-3';

in the case of a G116V mutant,
(sense)
                                        (SEQ ID NO: 28)
5'-CTGAGGATTACGTCGTGCTGAAAAC-3'.
```

A retroviral vector pQ vector expressing β-catenin S37A mutants was prepared by PCR subcloning from the pBI-EGFP-β-catenin (S37A) structure described previously. All of the structures and mutations were confirmed by nucleotide sequencing.

<Reference Example 7> Zinc Determination

Zinc ions were observed using 4-(2-pyridylazo) resorcinol (PAR) in an aqueous solution.

The glutathione S-transferase (GST)-fused TNKS1 PARP (1023-1327) protein was expressed in *E. coli* grown in LB medium supplemented with 100 μM $ZnCl_2$, and purified by affinity chromatography using Glutathione Sepharose 4B Fast Flow beads according to the manufacturer's protocol (GE Healthcare Life Sciences).

The purity (>99.5%) of a GST-TNKS1 PARP protein was confirmed by the concentration measurement method, and then, broadly dialyzed in Chelex100 treated buffer containing 25 mM HEPES (pH 7.0) and 2 mM DTT to remove unbound zinc ions.

The GST-TANK1 PARP protein was incubated with 500 μM $H_2O_2$ for 30 minutes in 200 μL of 40 mM HEPES (pH 7.0) reaction buffer containing 0.1 mM PAR. The formation of a PAR2-$Zn^{2+}$ complex was monitored at 500 nm with a UV/VIS spectrophotometer (Agilent).

The total zinc content of the purified GST-TNKS1 PARP protein used in the assay was determined by adding 0.5 mM p-chloromercuribenzoic acid to a reaction mixture.

<Reference Example 8> Peroxiredoxin Assay

The peroxidase assay was performed in a reaction mixture (200 μL) containing 250 μM NADPH, 1.5 μM yeast TR, 3 μM yeast Trx, a recombinant human Prx (PrxI (4.6 μM) and PrxII (16.4 μM)), and 50 μM HEPES (pH 7.0) containing 1 mM EDTA, and 200 M $H_2O_2$.

The mixture (minus $H_2O_2$) was preincubated for 5 minutes in the presence or absence of Compounds 1 to 6 (100 μM), and then, the reaction was initiated by adding $H_2O_2$. NADPH oxidation was monitored at 30° C. for 5 minutes as the absorbance decreased near 340 nm using an Agilent UV8453 spectrophotometer (Hewlett Packard. USA). The initial reaction rate was calculated using the linear portion of the curve and indicated as the amount of oxidized NADPH per minute.

<Reference Example 9> Histology, Immunohistochemistry, and Immunofluorescence Staining 12-Week-old male mice were anesthetized by inhalation of isoflurane gas ($N_2O:O_2$/70%: 30%) and subjected to transcardiac perfusion-fixation with heparinized saline containing 3.7% formaldehyde.

Then, the intestine was excised and cut into two parts, the small intestine and the colon, both of which were opened vertically and folded outward. The folded intestine was paraffin inserted and sectioned by a rotary microtome (Leica RM2255).

Three serial tissue sections with a thickness of 10 μm were stained with hematoxylin and eosin (HE). The folded intestine was immediately buried in OCT medium and frozen in dry ice. A cryostatt microtome, cryotome, was used to cut the tissue into 10 μm cross sections.

Cryotome is a microtome that handles frozen tissue. A microtome is a machine that cuts samples into pieces of a certain thickness to prepare specimens for microscopic observation. The samples were placed on Superfrost Plus slides (Surgipath Medical Inc. UK) and dried at room temperature and maintained at −80° C. until thawed for immunostaining.

Paraffin sections were dewaxed with xylene and rehydrated in ethanol for immunohistochemistry. Then, antigen retrieval was performed by boiling the sections in sodium citrate buffer (pH 6.0).

Tissue sections were incubated at 4° C. with an anti-Ki-67 antibody (a 1:200 dilution) and an affinity-purified anti-PrxII antibody (a 1:500 dilution) for 48 hours. After washing three times with PBS, the sections were incubated with a peroxidase-conjugated secondary antibody and stained with a 3,3'-diaminobenzidine (DAB) substrate solution.

Nuclei were further stained with hematoxylin. DAB staining images were obtained and quantified using HistoFAXS Tissue Analysis System (TissueGnostics, USA). For immunofluorescence staining, paraffin or frozen sections were blocked at room temperature for one hour with 5% normal rabbit serum (Vector Laboratories) in PBST (0.3% Triton X-100 in PBS).

Sections were incubated at 4° C. overnight with a primary antibody (a 1:500 dilution for the anti-PrxII antibody and a 1:100 dilution for the anti-BrdU antibody). After washing several times with PBST, the samples were incubated at room temperature with the Alexa Fluor 568-conjugated donkey anti-rabbit IgG antibody for 2 hours.

Sections were counterstained with 4',6-diamidino-2 phenylindole (DAPI, Sigma-Aldrich) for 30 minutes, and mounted using Vectashield mounting medium.

Fluorescence images were obtained at three random fields per tissue cross-section at 100× magnification using an LSM 51 Meta confocal microscope equipped with an argon and helium-neon laser (Carl Zeiss. Germany).

<Reference Example 10> Statistical Analysis

Unless otherwise specified, to determine statistical significance (P value), the data was analyzed by Analysis of Variance (ANOVA) using the Student's t-test for comparison between two groups, or using the Tukey-HSD or Tukey test for comparison of multiple groups (SPSS 12.0K in case of Windows, SPSS, Ill., USA). P<0.05 was considered statistically significant.

<Reference Example 11> Data Availability

The RNA sequencing data that supports the findings is deposited in the Gene Expression Omnibus database (GEO DB) (Accession Number GSE81429).
<Reagent>
The anti-tubulin antibody (mouse monoclonal, B-5-1-2, 1:8,000, T5168) and the anti-FLAG antibody (mouse monoclonal, M2, 1:1,000, F3165) were purchased from Sigma-Aldrich.

The antibodies for β-catenin (rabbit monoclonal, 6B3, 1:1,000, 9582), Axin1 (rabbit monoclonal, C76H11, 1:1, 000, 2087), pS33/37pT41-β-catenin (rabbit polyclonal, 1:1, 000, 9561), Axin2 (rabbit monoclonal, 76G6, 1:1,000, 2151), GSK3β(rabbit monoclonal, 27C10, 1:1,000, 9315), β-actin (rabbit monoclonal, 13E5, 1:1,000, 4970), and cyclin D1 (rabbit polyclonal, 1:1,000, 2922) were purchased from Cell Signaling Technology.

The antibodies for c-Myc (rabbit polyclonal, 1:1,000, sc-788), Ubiquitin (mouse monoclonal, P4D1, 1:1,000, sc-8017), pY279/216-GSK3β (rabbit polyclonal, 1:1,000, sc-135653), and tankyrase-½ (rabbit polyclonal, 1:1,000, H-350) were purchased from Santa Cruz Biotechnology.

The antibodies for anti-active β-catenin (mouse monoclonal, 8E7, 1:1,000, 05-665), anti-Myc (mouse monoclonal, 9E10, 1:1,000, 05-419), and anti-APC (mouse monoclonal, FE9, 1:1,000, ABC202) were purchased from Millipore.

The antibodies for Alexa Fluor 568-conjugated donkey, anti-rabbit IgG (1:200, A-21206), and anti-β-TrCP (mouse monoclonal, 1B1D2, 1:1,000, 37-3400) were purchased from Invitrogen.

The anti-PAR antibody that detects poly(ADP-ribose) chains (rabbit polyclonal, 1:2,000, 551813) was purchased from BD Bioscience.

The anti-Ki-67 antibody (rabbit monoclonal, SP6, 1:200, MA5-14520) was purchased from Thermo Fisher Scientific.

As described previously, rabbit polyclonal antibodies for PrxI (1:3,000), PrxII (1:3,000), and Prx-SO ⅔ (1:1,000) were produced.

Rabbit anti-PrxII antiserum was affinity-purified with a recombinant PrxII protein and agarose gel beads and used for immunofluorescence and proximity ligation assays (PLA).

Wnt3a was purchased from R & D Biosystems.

DuoLink in situ fluorescence reagent was purchased from Sigma-Aldrich.

TissueFocus Colorectal Tissue Microarray was purchased from OriGene Technologies (Rockville, USA).

Examples of the present invention described above have been described with reference to the embodiments shown in the drawings for ease of understanding, however, these are merely exemplary, and it will be understood by those skilled in the art that various modifications and equivalent other examples are possible therefrom. Therefore, the true technical protection scope of the present invention should be defined by the appended claims.

INDUSTRIAL APPLICABILITY

According to an embodiment of the invention, a composition, which can treat or prevent colorectal cancer (CRC) and reduce colorectal polyps by inhibiting the enzyme activity of peroxiredoxin 2 (PrxII) via regulation of the redox system of colorectal cancer (CRC) cells, can be provided.

According to another embodiment of the invention, a composition, which can treat or prevent colorectal cancer (CRC) and reduce colorectal polyps by reducing the interaction between peroxiredoxin 2 (PrxII) and tankyrase (TNKS) in the cytoplasm of APC-mutant cells, can be provided.

The invention claimed is:

1. A method for improving or treating colorectal cancer in a subject in need thereof, comprising the step of administering a pharmaceutically effective dose of a material inhibiting an enzyme activity of peroxiredoxin 2 to the subject, wherein the material inhibiting the enzyme activity of peroxiredoxin 2 is a compound of the following Formula 1:

[Formula 1]

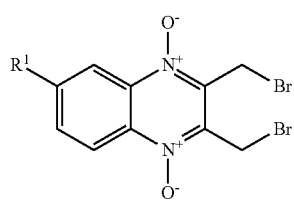

wherein in Formula 1 above, $R^1$ is —O—$R^2$, a cyclic group, or hydrogen; and $R^2$ is a branched or unbranched $C_1$ to $C_8$ alkyl, a branched or unbranched $C_2$ to $C_8$ alkenyl, a branched or unbranched $C_2$ to $C_8$ alkynyl, or an aromatic or non-aromatic cyclic group that is substituted or unsubstituted.

2. The method for improving or treating colorectal cancer of claim 1, wherein the material inhibiting the enzyme activity of peroxiredoxin 2 is one or more selected from the group consisting of Compound-1 to Compound-6 shown below:

Compound-1
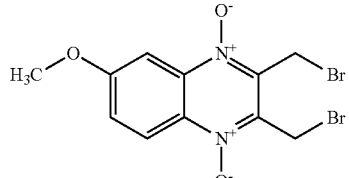

Compound-2
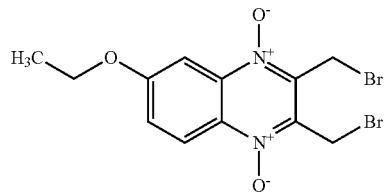 [SMILES: CCOc1ccc2c(c1)[n+]([O-])c(CBr)c(CBr)[n+]2[O-]]

Compound-3
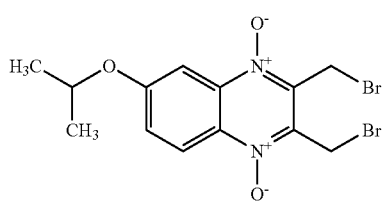 [SMILES: CC(C)Oc1ccc2c(c1)[n+]([O-])c(CBr)c(CBr)[n+]2[O-]]

Compound-4
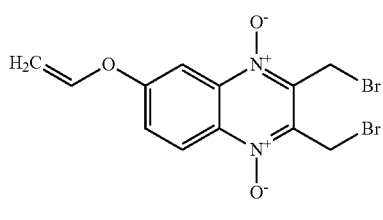 [SMILES: C=COc1ccc2c(c1)[n+]([O-])c(CBr)c(CBr)[n+]2[O-]]

Compound-5
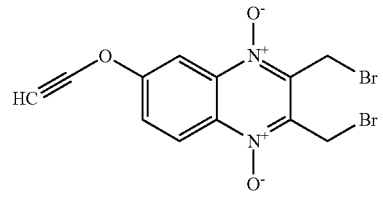 [SMILES: C#COc1ccc2c(c1)[n+]([O-])c(CBr)c(CBr)[n+]2[O-]]

Compound-6
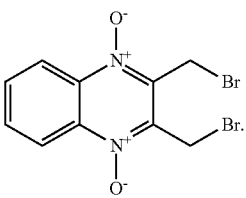

3. The method for improving or treating colorectal cancer of claim 1, wherein the material inhibiting the enzyme activity of peroxiredoxin 2 increases degradation of β-catenin.

4. The method for improving or treating colorectal cancer of claim 1, wherein the material inhibiting the enzyme activity of speroxiredoxin 2 decreases degradation of Axin1 by tankyrase (TNKS).

5. The method for improving or treating colorectal cancer of claim 1, wherein the material inhibiting the enzyme activity of peroxiredoxin 2 increases oxidative inactivation of tankyrase (TNKS).

6. The method for improving or treating colorectal cancer of claim 5, wherein the oxidative inactivation of tankyrase (TNKS) occurs in cytoplasm of an APC-mutant cell.

7. The method for improving or treating colorectal cancer of claim 1, wherein the material inhibiting the enzyme activity of peroxiredoxin 2 decreases interaction between peroxiredoxin 2 and tankyrase (TNKS) in cytoplasm of an APC-mutant cell.

* * * * *

SEQUENCE LISTING

```
<160> NUMBER OF SEQ ID NOS: 28

<210> SEQ ID NO 1
<211> LENGTH: 18
<212> TYPE: DNA
<213> ORGANISM: Artificial Sequence
<220> FEATURE:
<223> OTHER INFORMATION: primer for APC wild type

<400> SEQUENCE: 1
gccatccctt cacgttag                                                 18

<210> SEQ ID NO 2
<211> LENGTH: 21
<212> TYPE: DNA
<213> ORGANISM: Artificial Sequence
<220> FEATURE:
<223> OTHER INFORMATION: primer for APC mutant

<400> SEQUENCE: 2
ttctgagaaa gacagaagtt a                                             21

<210> SEQ ID NO 3
<211> LENGTH: 19
<212> TYPE: DNA
```

```
<213> ORGANISM: Artificial Sequence
<220> FEATURE:
<223> OTHER INFORMATION: primer for APC common

<400> SEQUENCE: 3
ttccactttg gcataaggc                                                19

<210> SEQ ID NO 4
<211> LENGTH: 20
<212> TYPE: DNA
<213> ORGANISM: Artificial Sequence
<220> FEATURE:
<223> OTHER INFORMATION: forward primer for PrxI

<400> SEQUENCE: 4
ctggaaacct ggcagtgata                                               20

<210> SEQ ID NO 5
<211> LENGTH: 22
<212> TYPE: DNA
<213> ORGANISM: Artificial Sequence
<220> FEATURE:
<223> OTHER INFORMATION: reverse primer for PrxI

<400> SEQUENCE: 5
ctgtgactga tagaagattg gt                                            22

<210> SEQ ID NO 6
<211> LENGTH: 24
<212> TYPE: DNA
<213> ORGANISM: Artificial Sequence
<220> FEATURE:
<223> OTHER INFORMATION: forward primer for PrxII

<400> SEQUENCE: 6
gatgatctcc gtggggcaaa caaa                                          24

<210> SEQ ID NO 7
<211> LENGTH: 24
<212> TYPE: DNA
<213> ORGANISM: Artificial Sequence
<220> FEATURE:
<223> OTHER INFORMATION: reverse primer for PrxII

<400> SEQUENCE: 7
atggcctccg gcaacgcgca aatc                                          24

<210> SEQ ID NO 8
<211> LENGTH: 22
<212> TYPE: DNA
<213> ORGANISM: Artificial Sequence
<220> FEATURE:
<223> OTHER INFORMATION: forward primer for Neo cassette

<400> SEQUENCE: 8
gcttgggtgg agaggctatt cg                                            22

<210> SEQ ID NO 9
<211> LENGTH: 24
<212> TYPE: DNA
<213> ORGANISM: Artificial Sequence
<220> FEATURE:
<223> OTHER INFORMATION: reverse primer for Neo cassette

<400> SEQUENCE: 9
gtaaagcacg aggaagcggt cagc                                          24
```

<210> SEQ ID NO 10
<211> LENGTH: 6
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: Xaa is any amino acid
<220> FEATURE:
<221> NAME/KEY: MISC_FEATURE
<222> LOCATION: (3)
<223> OTHER INFORMATION: Xaa is any amino acid
<220> FEATURE:
<221> NAME/KEY: MISC_FEATURE
<222> LOCATION: (5)
<223> OTHER INFORMATION: Xaa is any amino acid
<220> FEATURE:
<223> OTHER INFORMATION: consensus sequence of TNKS ARC domain

<400> SEQUENCE: 10

Arg Xaa Xaa Pro Xaa Gly
1               5

<210> SEQ ID NO 11
<211> LENGTH: 34
<212> TYPE: DNA
<213> ORGANISM: Artificial Sequence
<220> FEATURE:
<223> OTHER INFORMATION: forward primer of tankyrase-1

<400> SEQUENCE: 11
ataagaatgc ggccgcggcg gcgtcgcgtc gctc                              34

<210> SEQ ID NO 12
<211> LENGTH: 25
<212> TYPE: DNA
<213> ORGANISM: Artificial Sequence
<220> FEATURE:
<223> OTHER INFORMATION: reverse primer of tankyrase-1

<400> SEQUENCE: 12
gaagatctct aggtcttctg ctctg                                       25

<210> SEQ ID NO 13
<211> LENGTH: 34
<212> TYPE: DNA
<213> ORGANISM: Artificial Sequence
<220> FEATURE:
<223> OTHER INFORMATION: forward primer of 1-158 amino acid residue of
      tankyrase-1

<400> SEQUENCE: 13
ataagaatgc ggccgcggcg gcgtcgcgtc gctc                              34

<210> SEQ ID NO 14
<211> LENGTH: 29
<212> TYPE: DNA
<213> ORGANISM: Artificial Sequence
<220> FEATURE:
<223> OTHER INFORMATION: reverse primer of 1-158 amino acid residue of
      tankyrase-1

<400> SEQUENCE: 14
gaagatctct aggccgcctc ggggctctc                                   29

<210> SEQ ID NO 15
<211> LENGTH: 36

<212> TYPE: DNA
<213> ORGANISM: Artificial Sequence
<220> FEATURE:
<223> OTHER INFORMATION: forward primer of 158-595 amino acid residue of
      tankyrase-1

<400> SEQUENCE: 15
ataagaatgc ggccgccgga gttagcagca cagcac                                 36

<210> SEQ ID NO 16
<211> LENGTH: 31
<212> TYPE: DNA
<213> ORGANISM: Artificial Sequence
<220> FEATURE:
<223> OTHER INFORMATION: reverse primer of 158-595 amino acid residue of
      tankyrase-1

<400> SEQUENCE: 16
gaagatctct acaaagcagt ctgaccaagg g                                      31

<210> SEQ ID NO 17
<211> LENGTH: 37
<212> TYPE: DNA
<213> ORGANISM: Artificial Sequence
<220> FEATURE:
<223> OTHER INFORMATION: forward primer of 596-1022 amino acid residue
      of tankyrase-1

<400> SEQUENCE: 17
ataagaatgc ggccgcgcat agagccgccc tagcagg                                37

<210> SEQ ID NO 18
<211> LENGTH: 32
<212> TYPE: DNA
<213> ORGANISM: Artificial Sequence
<220> FEATURE:
<223> OTHER INFORMATION: reverse primer of 596-1022 amino acid residue
      of tankyrase-1

<400> SEQUENCE: 18
gaagatctct atccttcctt cctttctgtt cc                                     32

<210> SEQ ID NO 19
<211> LENGTH: 35
<212> TYPE: DNA
<213> ORGANISM: Artificial Sequence
<220> FEATURE:
<223> OTHER INFORMATION: forward primer of 1023-1327 amino acid residue
      of tankyrase-1

<400> SEQUENCE: 19
ataagaatgc ggccgcagaa gttgctggtc ttgac                                  35

<210> SEQ ID NO 20
<211> LENGTH: 25
<212> TYPE: DNA
<213> ORGANISM: Artificial Sequence
<220> FEATURE:
<223> OTHER INFORMATION: reverse primer of 1023-1327 amino acid residue
      of tankyrase-1

<400> SEQUENCE: 20
gaagatctct aggtcttctg ctctg                                             25

<210> SEQ ID NO 21
<211> LENGTH: 35
<212> TYPE: DNA

<213> ORGANISM: Artificial Sequence
<220> FEATURE:
<223> OTHER INFORMATION: sense strand for C1163S mutant of tankyrase-1

<400> SEQUENCE: 21
gttgagggag cggttctccc accgacagaa ggaag                    35

<210> SEQ ID NO 22
<211> LENGTH: 33
<212> TYPE: DNA
<213> ORGANISM: Artificial Sequence
<220> FEATURE:
<223> OTHER INFORMATION: sense strand for C1234S mutant of tankyrase-1

<400> SEQUENCE: 22
ggaggaggaa caggctcccc tacacacaag gac                      33

<210> SEQ ID NO 23
<211> LENGTH: 34
<212> TYPE: DNA
<213> ORGANISM: Artificial Sequence
<220> FEATURE:
<223> OTHER INFORMATION: sense strand for C1242S mutant of tankyrase-1

<400> SEQUENCE: 23
cacaaggaca ggtcatccta tatgtcac agac                       34

<210> SEQ ID NO 24
<211> LENGTH: 37
<212> TYPE: DNA
<213> ORGANISM: Artificial Sequence
<220> FEATURE:
<223> OTHER INFORMATION: sense strand for C1245S mutant of tankyrase-1

<400> SEQUENCE: 24
caggtcatgc tatatatctc acagacaaat gctcttc                  37

<210> SEQ ID NO 25
<211> LENGTH: 32
<212> TYPE: DNA
<213> ORGANISM: Artificial Sequence
<220> FEATURE:
<223> OTHER INFORMATION: sense strand for C1252S mutant of tankyrase-1

<400> SEQUENCE: 25
gacaaatgct cttctctaga gtgacccttg gg                       32

<210> SEQ ID NO 26
<211> LENGTH: 25
<212> TYPE: DNA
<213> ORGANISM: Artificial Sequence
<220> FEATURE:
<223> OTHER INFORMATION: sense strand for G9V mutant of PrxII

<400> SEQUENCE: 26
gcgcgcatcg taaagccagc ccctg                               25

<210> SEQ ID NO 27
<211> LENGTH: 25
<212> TYPE: DNA
<213> ORGANISM: Artificial Sequence
<220> FEATURE:
<223> OTHER INFORMATION: sense strand for G23V mutant of PrxII

<400> SEQUENCE: 27
gcggtggttg atgtcgcctt caaag                               25

```
<210> SEQ ID NO 28
<211> LENGTH: 25
<212> TYPE: DNA
<213> ORGANISM: Artificial Sequence
<220> FEATURE:
<223> OTHER INFORMATION: sense strand for G116V mutant of PrxII

<400> SEQUENCE: 28
ctgaggatta cgtcgtgctg aaaac                                    25
```